United States Patent [19]
Penney et al.

[11] Patent Number: 5,994,361
[45] Date of Patent: Nov. 30, 1999

[54] SUBSTITUTED PURINYL DERIVATIVES WITH IMMUNOMODULATING ACTIVITY

[75] Inventors: Christopher Penney, Dollard-des-Ormeaux; Boulos Zacharie, Laval-des-Rapides; Lyne Gagnon; Giorgio Attardo, both of Laval; Timothy P. Connolly; Yves St-Denis, both of Montreal; Salam Kadhim, Laval, all of Canada

[73] Assignee: Biochem Pharma, Canada

[21] Appl. No.: 08/474,073

[22] Filed: Jun. 7, 1995

Related U.S. Application Data

[63] Continuation-in-part of application No. 08/264,028, Jun. 22, 1994, abandoned.

[51] Int. Cl.$^6$ .................. A61K 31/52; C07D 473/40; C07D 473/34; C07D 473/30
[52] U.S. Cl. .................. 514/261; 514/262; 514/266; 544/264; 544/265; 544/266; 544/267; 544/268; 544/269; 544/270; 544/271; 544/272; 544/273; 544/276; 544/277
[58] Field of Search .................. 544/264, 265, 544/266, 267, 268, 269, 270, 271, 272, 273, 276, 277; 514/261, 262, 263, 264, 265, 266

[56] References Cited

U.S. PATENT DOCUMENTS

| | | | |
|---|---|---|---|
| 3,165,520 | 1/1965 | Schmidt et al. | 250/56.4 |
| 4,100,286 | 7/1978 | Regnier | 544/277 |
| 4,479,951 | 10/1984 | Klessing | 544/277 |
| 4,567,182 | 1/1986 | Ferraris | 514/262 |
| 4,602,089 | 7/1986 | Simon et al. | 544/265 |
| 4,663,326 | 5/1987 | Hamilton | 514/258 |
| 4,694,006 | 9/1987 | Bundgaard et al. | 544/262 |
| 4,853,386 | 8/1989 | Friebe | 544/277 |
| 4,968,674 | 11/1990 | Taniyama | 544/277 |
| 5,015,739 | 5/1991 | Saksena | 544/277 |
| 5,049,671 | 9/1991 | Daluge | 544/277 |
| 5,089,500 | 2/1992 | Daluge | 544/277 |
| 5,110,818 | 5/1992 | Allgeier | 544/264 |
| 5,214,048 | 5/1993 | Shimada | 544/264 |
| 5,272,151 | 12/1993 | Marzi et al. | 514/258 |
| 5,332,744 | 7/1994 | Chakravarty | 544/264 |
| 5,369,098 | 11/1994 | Slusarchyk | 544/277 |
| 5,470,857 | 11/1995 | Borcherding | 544/277 |
| 5,516,905 | 5/1996 | Brown | 544/277 |

FOREIGN PATENT DOCUMENTS

| | | | |
|---|---|---|---|
| 0077460 | 4/1983 | European Pat. Off. | |
| 099493 | 2/1984 | European Pat. Off. | |
| 108285 | 5/1984 | European Pat. Off. | 544/264 |
| 0260588 | 3/1988 | European Pat. Off. | |
| 0291229 | 11/1988 | European Pat. Off. | |
| 077 460 | 4/1989 | European Pat. Off. | |
| 420237 | 4/1991 | European Pat. Off. | 544/264 |
| 0 464 009 A2 | 1/1992 | European Pat. Off. | |
| 0464009 | 1/1992 | European Pat. Off. | |
| 0506628 | 9/1992 | European Pat. Off. | |
| 59-98099 | 6/1984 | Japan | 544/277 |
| 2134907 | 8/1984 | United Kingdom | 544/277 |
| WO 8805437 | 7/1988 | WIPO | |
| WO 89/05818 | 6/1989 | WIPO | |
| 95-09855 | 4/1995 | WIPO | |
| WO 9513277 | 5/1995 | WIPO | |

OTHER PUBLICATIONS

Beauchamp, Antiviral. Chem & Chemo. 3, 157–164 (1992).

Il Farmaco (1990) vol. 45 entitled Synthetic Biological Response Modifiers; Part 1. Synthesis and Immunomodulatory Properties of Some N–(w–(Hypoxanthin–9–YL) Alkoxycarbonyl)–L–Arginines; Authors: R. Stradi, E. Rossi, L. Perezzani, G. Migliorati, C. Riccardi, P. Cornaglia–Ferraris; pp. 39–47.

Int. J. Immunopharmac, vol. 13, No. 7 (1991) entitled "Short Communication, A New Peptide Analog (RM06) Modulates the Growth of Hematopoietic Cells"; Authors: P. Cornaglia–Ferraris, A. Biano, M.V. Corrias, R. Stradi; pp. 1005–1012.

Journal of Biological Response Modifiers (1990) vol. 9 entitled "Antiviral Activity of the Novel Immune Modulator 7–Thia–8–Oxoguanosine"; Authors: Donald F. Smee, Hassan A. Alaghamandan, Howard B. Cottam, Weldon B. Jolley, and Roland K. Robins; pp. 24–32.

(List continued on next page.)

*Primary Examiner*—Mark L. Berch
*Attorney, Agent, or Firm*—Baker & Botts LLP

[57] ABSTRACT

The present invention comprises a compound of formula I:

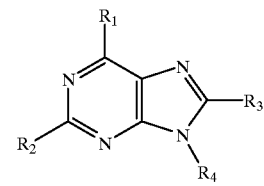

$R_1$ of Formula I is substituted amino represented by formula $NR^5R^6$ wherein $R^5$ and $R^6$ are independently selected from the group consisting of hydrogen, $C_{1-4}$ alkyl, and unsubstituted amino with the proviso that $R^5$ and $R^6$ are not both hydrogen, and further that $R^5$ and $R^6$ are not both amino. $R_2$ and $R_3$ of Formula I are independently selected from the group consisting of hydrogen; $C_{1-4}$ alkyl; amino; substituted or unsubstituted thiol; and halogen. Moreover, $R_4$ of Formula I is represented by the formula $R^{12}$-$X^{12}$ wherein $R^{12}$ is a saturated or unsaturated linear hydrocarbon chain of 5–20 carbons optionally containing one or more interruptions within the chain by a heteroatom, and optionally substituted with one or more =O, or =S. Finally, $X^{12}$ is selected from the group consisting of hydroxy, an aminoalkyl group, and a known amino acid bound by its α-amino group.

23 Claims, 7 Drawing Sheets

OTHER PUBLICATIONS

Chemistry & Chemotherapy (1991) vol. 2 entitled A Study of the Efficacy of the Immunomodulatory Compound 7–Thia–8–Oxoguanosine in Coronavirus 229E Infections in Human Volunteers; Authors: P.G. Higgins, G.I. Barrow, D.A.J. Tyrrell, N.J.C. Snell, K. Jones, W.B. Jolley; pp. 61–63.

*Antimicrobial Agents and Chemotherapy* (1991) vol. 2 entitled "Immunoenhancing Properties and Antiviral Activity of 7–Deazaguanosine in Mice"; Authors: D. Smee, H.A. Alaghamandan, J. Gilbert, R.A. Burger, A. Jin, B.S. Sharma, K. Ramasamy, G.R. Revankar, H.B. Cottam, W.B. Jolley, R.K. Robins; pp. 152–157.

*Int. J. Immunopharmic.* vol. 13 (1991) Methyl Inosine Monophosphate (MIMP), a New Purine Immunomodulator for HIV Infection; Authors: J.W. Hadden, A. Giner–Sorolla, E.M. Hadden; pp. 49–54.

*Thymus* vol. 14 "ST789: A New Synthetic Immunomodulator" pp. 51–55; Authors: C. De Simone, E. Arrigoni Martelli; (1992).

Stradi Chemical Abstracts, vol. 113, Aug. 27, 1990, No. 9, p. 19, Abstr. 70699.

Stradi Chemical Abstract, vol. 117, Aug. 17, 1992, No. 7, p. 850, Abstr. 70282.

De Simone Chemical Abstract, vol. 117, Aug. 3, 1992, No. 5, p. 3, Abstr. 39631.

Schaeffer, et al., entitled "Enzyme Inhibitors V. The Syntheses of 6–Substituted–(9–Hydroxy alkyl) purines and Their Evaluation as Inhibitors of Adenosine Deaminase" *Biochemistry.* Jan. 1965, vol. 1, pp. 71–75.

Coligan et al., "Current Protocols in Immunology," (1992), Sections 3.11, 3.12, 7.10.

SUBSTITUTED PURINYL DERIVATIVES WITH IMMUNOMODULATING ACTIVITY

This application is a continuation-in-part of application Ser. No. 08/264,028 filed on Jun. 22, 1994, abandoned.

FIELD OF THE INVENTION

The present invention covers substituted purinyl compounds. In particular, the present invention concerns 6-substituted purinyl alkoxycarbonyl amino acid compounds, more particularly arginine derivatives.

BACKGROUND OF THE INVENTION

The primary function of the immune system relates to the protection of the body from disease. The immune system protects against not only those diseases which result from an attack by bacteria, viruses, and other pathogens, but also cancer, as well as disease states which result from immune imbalance, opportunistic infections, or autoimmune disorders.

Modulation of the immune system through pharmaceutically induced stimulation or suppression offers an important approach to the control of disease. Compounds which nonspecifically stimulate the immune system are of potentially significant medicinal importance and have been the object of a lengthy research effort. Often, the research results show that immunomodulating compounds are either weak immunostimulants, and hence not very effective, or potent immunostimulants and, therefore, effective but toxic by virtue of this potent immunostimulating activity.

Among the many classes of compounds which nonspecifically stimulate the immune system are nucleosides which are well known in the art. For example, 7-thia-8-oxoguanosine has been described by D. F. Smee et al. in the Journal of Biological Response Modifiers, 9, 24–32, 1990 as an antiviral agent in mice. The activity of this compound is derived from its ability to activate NK and B cells in the immune system, and to induce interferon. However, subsequent antiviral studies in humans as reported by P. G.

Higgins et al. in Antiviral Chemistry and Chemotherapy, 2, 61–63, 1991, have disclosed few encouraging results. One problem has been the lack of oral bioavailability.

Other nucleosides have been synthesized and studied in an effort to develop an improved medication. For example, D. F. Smee et al. report in Antimicrobial Agents and Chemotherapy, 35, 152–157, 1991, that 7-deazaguanosine has significant immunostimulatory and antiviral activity after oral administration. However, these results are preliminary. With many nucleoside compounds, toxicity is an important issue which must also be closely analyzed.

A particular class of nucleoside immunostimulants has arisen from inosine and other similar hypoxanthine-containing compounds. A well know example is isoprinosine, an inosine-containing complex. Isoprinosine has been thoroughly studied as an immunomodulator and referred to as a "gold standard" by C. D. Simone et al. in Thymus, 19, 51–55, 1992. Some rationale for the activity of hypoxanthine- (inosine) containing compounds arises from the observation that a lack of adenosine deaminase, the enzyme which converts adenosine to inosine, results in severe combined immunodeficiency disease (SCID).

Although very nontoxic, isoprinosine is not an effective immunomodulator, and in order to improve its immunopharmacological properties, numerous analogues have been synthesized, as reported by J. W. Hadden et al. in International Journal of Immunopharmacology, 13, 49–54, 1991 (suppl. 1). In particular, they describe a prodrug in the form of inosine 5'-monophosphate (inosine, unless complexed, has little in vivo activity) and methyl inosine monophosphate (MIMP). However, MIMP is not a very active immunomodulator.

In an effort to retain the nontoxic properties of isoprinosine, but enhance the immunostimulatory activity, an immunomodulator was synthesized which contained both hypoxanthine and the amino acid L-arginine covalently linked by a pentamethylene bridge. The compound, ST 789 (hypoxanthine pentyloxycarbonyl L-arginine, formerly PCF 39) has been thoroughly described in a recent issue of Thymus, 19, S1-S112 (1992). L-Arginine was selected because it is known to play a role in immune activation and is present at the terminus of many immunomodulatory peptides such as tuftsin substance P, thymopentin, and splenopentin. ST 789 is further described in European Patent Application #91830284, publication #464,009, published Jan. 2, 1992. Analogues of ST 789 are also described in the European publication where oligopeptides composed of naturally occurring L-amino acids replace L-arginine. However, the purine base portion of the molecule remains hypoxanthine.

While no immunological comparison was made with isoprinosine, a similar pattern emerged. The compounds are nontoxic but, at best, moderate immunostimulants. For example, there was no indication that ST 789, or analogues thereof, could stimulate an important immune cell subset such as cytotoxic T lymphocytes (CD8$^+$ T cells). This subset plays a key role in the defense of the body from viral infections and cancer.

P. Cornaglia-Ferraris describes still another analogue of ST 789 in International Journal of Immunopharmacology, 13, 1005–1012, 1991. In the published compound, L-arginine is replaced with the bombesin carboxy terminus dipeptide L-leucyl L-methionine. The purine base remains hypoxanthine. In fact, in this class of compounds where a purine base is covalently linked by a methylene chain to an amino acid or an oligopeptide, very little data has been reported for compounds including a purine base other than hypoxanthine. Further, because of the requirement for physiologically active amino acids in mammalian systems, all the work reported to date describes amino acids of the (natural) L-configuration. One brief description of the replacement of hypoxanthine with the naturally occurring purine bases adenine and guanine is reported by R. Stradi et al. in Fl. Farmaco, 45, 39–47, 1990, but there is no indication of significant biological activity.

As noted above, adenosine deaminase, and by implication inosine, is necessary to maintain normal immune status. Therefore, in U.S. Pat. No. 5,272,151 issued Dec. 21, 1993, M. Marzi et al. reported that in ST 789 the hypoxanthine is replaced with the xanthine oxidase inhibitor allopurinol. The result is ST 689, allopurinol pentanol. This substitution is expected to increase the concentration of inosine in vivo since inosine is catabolized to xanthine, and then uric acid in mammals in the presence of xanthine oxidase enzyme. However, allopurinol was noted to be immunosuppressive and ST 689 was not significantly more immunostimulatory than ST 789 in most of the immunology assays reported in the '151 patent.

Levamisole is another immunoregulator agent used against malignant melanoma. It has now been found that levamisole induces serious thrombocytopenia after starting adjuvant levamisole therapy for malignant melanoma [Med. Pediatr. Oncol. April 1995, 24 (4), 262–4].

The prior art indicates that there is a need for compounds which have the ability to stimulate a number of immune cell subsets and thereby possess significant immunomodulating activity, but, at the same time, lack toxicity.

SUMMARY OF THE INVENTION

In accordance with the present invention, there is provided a compound which possesses significant immunostimulatory capability both in vitro and in vivo.

Specifically, there is provided a compound which possesses activity in increasing the amount of cytotoxic T cells in vitro and in vivo.

In another aspect of the invention there is provided an immunomodulatory compound which does not have significant toxicity and, in particular, does not have the toxicity which is associated with significant or potent immunostimulation.

In another aspect of the invention, there is provided an immunomodulatory compound possessing a purine derivative which is not a natural base.

In a further aspect of the invention, there is provided a compound which acts as a control against tumor growth.

The present invention includes compounds of formula (I):

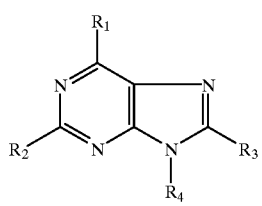

(I)

or pharmaceutically acceptable derivatives thereof, wherein $R_1$ is selected from the group consisting of hydrogen; $C_{1-16}$ alkyl; halogen; substituted or unsubstituted thiol; unsubstituted or substituted amino; and $OR^8$ wherein $R^8$ is selected from the group consisting of hydrogen, $C_{1-16}$ alkyl, $C_{1-8}$ acyl, and $C_{7-18}$ aryl;

$R_2$ and $R_3$ are independently selected from the group consisting of hydrogen; $C_{1-4}$ alkyl; amino; substituted or unsubstituted thiol; and halogen; and $R_4$ is selected from the group consisting of a linear or cyclic carbon chain of the formula $(CH_{0-2})_{0-20}$ -$X^{12}$ optionally interrupted with one or more heteroatom, and optionally substituted with one or more =O, or =S, and wherein $X^{12}$, is selected from the group consisting of hydroxy, an aminoalkyl group, an amino acid, or a peptide of 2–8 amino acids, with the proviso that, when $R_1$ is $NH_2$, and $R_4$ is pentyloxy carbonyl-L-arginine, then $R_2$ is not hydrogen, and when $R_1$ is OH, and $R_4$ is pentyloxycarbonyl-L-arginine, then $R_2$ is not $NH_2$.

The following definitions are used herein.

The term "alkyl" as employed herein includes both straight and branched chain radicals, for example methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof. The chain may be saturated or unsaturated and may contain, for example, double and triple bonds. The alkyl may be interrupted or substituted with, for example, one or more halogen, oxygen, hydroxy, silyl, amino, or other acceptable substituents.

The term "aromatic or non-aromatic ring" as used herein includes 5 and 6 membered aromatic and non-aromatic rings uninterrupted or interrupted with one or more heteroatom, for example O, S, SO, $SO_2$, and N, or the ring may be unsubstituted or substituted with, for example, halogen, alkyl, acyl, hydroxy, aryl, and amino, said heteroatom and substituent may also be substituted with, for example, alkyl, acyl, aryl, aralkyl.

The term "acyl" as used herein refers to carbonyl groups of the formula —COR wherein R may be any suitable substituent such as, for example, alkyl, amino, halogen, thiol, oxygen, hydroxy, and hydrogen.

The term "aryl" as employed herein refers to monocyclic or bicyclic aromatic groups containing from 6 to 10 carbons in the ring portion, such as phenyl, naphtyl, substituted phenyl, naphtyl, substituted phenyl or substituted naphthyl, wherein the substituent on either the phenyl or naphthyl may be for example $C_{1-4}$ alkyl, halogen, $C_{1-4}$ alkoxy, hydroxy or nitro.

The term "aralkyl" as used herein refers to alkyl groups as discussed above having an aryl substituent, such as benzyl, p-nitrobenzyl, phenethyl, diphenylmethyl, and triphenylmethyl.

The term "substituted amino" as used herein refers to an amino which may be substituted with one or more substituent, for example, $C_{1-8}$ alkyl, $C_{1-8}$ acyl, $C_{6-12}$ aryl, hydroxy, and hydrogen.

The term "amino acid" as employed herein includes and encompasses all of the naturally occurring amino acids, those amino acids in their D- and L-configurations, and the known non-native, synthetic, and modified amino acids, such as homocysteine, ornithine, norleucine and β-valine. A list of non natural amino acids may be found in "The Peptides", vol 5, 1983, Academic Press, Chapter 6 by D. C. Roberts and F. Vellaccio.

The term "linear or cyclic" when used herein includes, for example, a linear chain which may optionally be interrupted by an aromatic or non-aromatic ring. Cyclic chain includes, for example, an aromatic or non-aromatic ring which may be connected to, for example, a carbon chain which either precedes or follows the ring.

The term "pharmaceutically acceptable derivative" as employed herein, includes any pharmaceutically acceptable salt, ester, or salt of such ester, of a compound of formula I or any other compound which, upon administration to the recipient, is capable of providing (directly or indirectly) a compound of formula I or an active metabolite or residue thereof.

DESCRIPTION OF THE INVENTION

Figure 1:
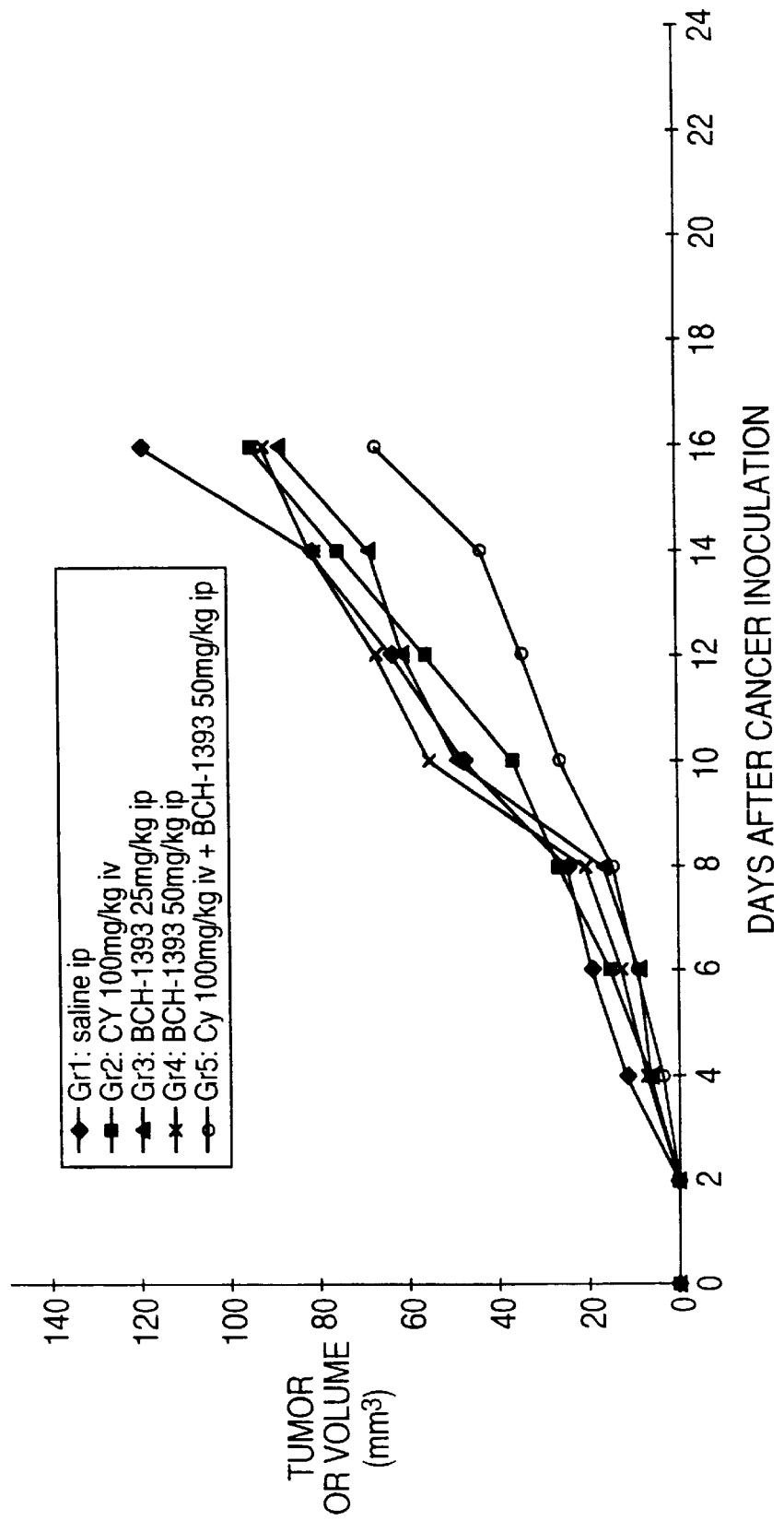
FIG. 1 illustrates the variations in tumor growth for mice treated with cyclophosphamide, or compound #1, or both.

In one aspect of the present invention, there is provided a compound of formula (I) wherein $R_4$ is $(CH_{0-2})_{1-8}$—$X^{12}$, wherein $X^{12}$ is OH.

In a further aspect of the invention, there is provided a compound of formula (I) wherein $R_4$ is $(CH_2)$—L—O—CO—$X^{12}$, wherein L is a linear or cyclic carbon chain optionally interrupted with one or more O, S, or NH.

Preferably, $X^{12}$ can be $(CH_2)_n NH_2$ wherein n is an integer between 1 and 6. More preferably, n is 2.

More preferably, $X^{12}$ can be a naturally occuring amino acid in the D- or L- configuration. Preferably, these amino acids can be selected from the group consisting of: arginine, glycine, alanine, glutamic acid, valine, ornithine, or citrulline, or conservative substitutions thereof.

Still, more preferably, the amino acid is L-arginine. Even more preferably, the amino acid is D-arginine.

In an alternative embodiment of the invention, $X^{12}$ may be a peptide of 2 to 8 amino acids.

Preferably, such a peptide can be Val-Pro-Leu, or Ile-Pro-Ile, or conservative substitutions thereof.

In another embodiment of the invention, L can be selected from: —$(CH_2)_n$—, —$(CH_2)_m$—H—$(CH_2)_m$—, and $(CH_2)_m$—C≡C—$(CH_2)_m$—, wherein H is O, S, or NH, n is an integer between 1 and 6, and m is an integer between 1 and 3.

Preferably, L can be selected from: phenyl, cyclohexyl, dioxolanyl, oxathiolanyl, and cyclopentyl.

In an further alternative of the invention, when $R_1$ is $C_{1-16}$ alkyl, $R_1$ can be an aromatic or non aromatic ring optionally interrupted with one or more heteroatom, and optionally substituted with one or more heteroatom, hydroxy, halogen, $C_{1-16}$ alkyl, $C_{1-16}$ acyl, $C_{6-12}$ aryl, nitro, or substituted or unsubstituted amino.

More preferably, $R_1$ can be OH, $OCH_3$, SH or $SCH_3$.

Alternatively, $R_1$ can be selected from the group consisting of: hydrogen, halogen, $C_{1-6}$ alkyl, unsubstituted or substitued amino, OH, and $OC_{1-6}$ alkyl, SH, or $SC_{1-6}$ alkyl.

Preferably, $R_1$ can be chloro.

Alternatively, $R_1$ can be represented by formula $NR^5R^6$ wherein $R^5$ and $R^6$ are independently selected from the group consisting of hydrogen, $C_{1-4}$ alkyl, $C_{1-4}$ alkoxy, $C_{1-4}$ acyl, substituted or unsubstituted amino, and $C_{6-10}$ aryl.

Preferably, $R_1$ can be selected from the group consisting of:

—$N(CH_3)_2$,
—$NHNH_2$,
—$NHCH_3$,
—$NH_2$,
—$N(NH_2)CH_3$,
—NH—$CH(CH_3)CH_2$—O—$(CO)CH_3$,

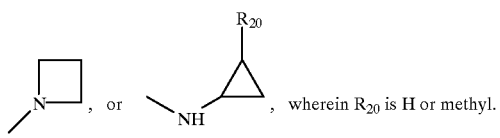, wherein $R_{20}$ is H or methyl.

Even more preferably, $R_1$ can be: —$N(CH_3)_2$. Even more preferably, $R_1$ can be: —$NHNH_2$. Even more preferably, $R_1$ can be: —$NHCH_3$, Even more preferably, $R_1$ can be: —$NH_2$, and Even more preferably, $R_1$ can be: —$N(NH_2)CH_3$.

Most preferably, $R_1$ can be —$N(CH_3)_2$.

In a further alternative embodiment of the invention, $R_2$ and $R_3$ can be independently selected from the group consisting of: Cl, Br, I, and F.

Preferably, $R_2$ and $R_3$ can be independently Cl, or Br.

More preferably, $R_2$ can be H, Cl, or $NH_2$.

More preferably, $R_3$ can be H, Br, or SH, or $SCH_3$.

Most preferably, the compound of the invention is represented by formula (I) wherein $R_1$ is $N(CH_3)_2$; $R_2$ and $R_3$ are both hydrogen; and $R_4$ is pentyloxycarbonyl-D-arginine, or pharmaceutically acceptable derivatives thereof.

Preferred compounds of the present invention are selected from:

| | |
|---|---|
| Compound #III | N-(6-Chloropurin-9-yl)-5-pentanol |
| Compound #V | N-(6-N,N-Dimethylaminopurin-9-yl)-pentanol |
| Compound #1 | N,N-Dimethylaminopurinyl Pentoxycarbonyl D-Arginine |
| Compound #2 | N,N-Dimethylaminopurinyl Pentoxycarbonyl L-Arginine |
| Compound #3 | N-Monomethylaminopurinyl Pentoxycarbonyl D-Arginine |
| Compound #3a | N-(6-N-Methyl-Aminopurin-9 -yl)-pentanol |
| Compound #4 | N-Monomethylaminopurinyl Pentoxycarbonyl L-Arginine |
| Compound #5 | Aminopurinyl Pentoxycarbonyl D-Arginine |
| Compound #5a | N-(6-Aminopurin-9-Yl) 5-Pentanol |
| Compound #6 | Aminopurinyl Pentoxycarbonyl L-Arginine |
| Compound #7 | Hydrazinopurinyl Pentoxycarbonyl D-Arginine |
| Compound #7a | N-(6-Hydrazinopurin-9-yl) 5-Pentanol |
| Compound #8 | Hydrazinopurinyl Pentoxycarbonyl L-Arginine; |
| Compound #9 | Chloropurinyl Pentoxycarbonyl D-Arginine; |
| Compound #10 | Chloropurinyl Pentoxycarbonyl L-Arginine; |
| Compound #11 | Hydroxypurinyl Pentoxycarbonyl D-Arginine; |
| Compound #12 | Mercaptopurinyl Pentoxycarbonyl D-Arginine; |
| Compound #13 | Mercaptopurinyl Pentoxycarbonyl L-Arginine; |
| Compound #14 | N,N-Dimethylaminopurinyl Pentoxycarbonyl Glycine; |
| Compound #15 | N,N-(6-Dimethylaminopurin-9-yl)-7'-ethoxy-ethoxycarbonyl-D-arginine; |
| Compound #16 | (2S,4S)-2-(N,N-dimethylaminopurin-9-yl)-4-(methyloxycarbonyl-D-arginine)-1,3-dioxolane; |
| Compound #17 | N-(6-Dimethylamino-8-bromopurinyl-Pentoxycarbonyl L-Arginine; |
| Compound #18 | N-(6-dimethylamino-8-bromopurin-9-yl) 7 -pentoxycarbonyl-D-arginine; |
| Compound #19 | N-9-purinyl-5-pentanol; |
| Compound #20 | N-9-purinyl-7-pentyloxycarbonyl-D-arginine; |
| Compound #21 | N-9-purinyl-7-pentyloxycarbonyl-L-arginine; |
| Compound #22 | N, N-Dimethylaminopurinyl Pentoxycarbonyl L-Valyl L-Prolyl L-Leucine; |
| Compound #23 | N,N-Dimethylaminopurinyl Pentoxycarbonyl L-Isoleucyl L-Prolyl L-Isoleucine; |
| Compound #24 | N-(6-Cyclopropylaminopurin-9-yl)-5-pentanol; |
| Compound #25 | N-(6-cyclopropylaminopurin-9-yl)-7-pentyloxycarbonyl-D-arginine; |
| Compound #26 | N-(6-cyclopropylaminopurin-9-yl)-7-pentyloxycarbonyl-L-arginine; |
| Compound #27 | N-(6-Azetidinepurin-9-yl)-5-pentanol; |
| Compound #28 | N-(6-Azetidinepurin-9-yl)-7-pentyloxycarbonyl-D-arginine; |
| Compound #29 | N-(6-Azetidinepurin-9-yl)-7-pentyloxycarbonyl-L-arginine; |
| Compound #30 | trans-(N-6-chloropurin-9-yl)-4-methyl-cyclohexyl-methanol; |
| Compound #31 | trans-(N-6-dimethylaminopurin-9-yl)-4-methyl-cyclohexyl-methanol; |

| | |
|---|---|
| Compound #32 | trans-(N-6-dimethylaminopurin-9-yl)-4-methyl-cyclohexyl-methyloxycarbonyl-D-arginine; |
| Compound #33 | trans-(N-6-hydroxypurin-9-yl)-4-methyl-cyclohexyl-methanol; |
| Compound #34 | trans-(N-6-methoxypurin-9-yl)-4-methyl-cyclohexyl-methanol; |
| Compound #35 | cis-(N-6-dimethylaminopurin-9-yl)-4-methyl-cyclohexyl-methanol; |
| Compound #36 | cis-(N-6-dimethylaminopurin-9-yl)-4-methyl-cyclohexyl-methyloxycarbonyl-D-arginine; |
| Compound #37 | N-(6-dimethylaminopurin-9-yl) 7-pentoxycarbonyl-D-citrulline; |
| Compound #38 | N-(6-methylaziridinepurin-9-yl)-5-pentanol; |
| Compound #39 | racemic N-(6-methylaziridine purine-9-yl)-7-pentyloxycarbonyl-D-arginine; |
| Compound #40 | N,N-(6-Dimethylaminopurinyl-9-yl)-7-thioethoxy-ethoxycarbonyl-D-arginine; |
| Compound #41 | Meta-(N-6-dimethylaminopurinyl-9-yl) methyl-benzyloxycarbonyl-D-arginine; |
| Compound #42 | 5-(N-6-Dimethylaminopurinyl-9-yl)-3-pentynyl-1-oxycarbonylD-arginine; |
| Compound #43 | Racemic N-[6-(1-methyl-2-acetoxy)-ethylaminopurin-9-yl]-5-pentanol; |
| Compound #44 | Racemic N-[6-(1-methyl-2-acetoxy) ethylaminopurin-9-yl]-7-pentyloxy-carbonyl-D-arginine; |
| Compound #45 | N-(2,6-Dichloropurin-9-yl)-5-pentanol; |
| Compound #46 | N-(2,6-Dichloropurin-9-yl)-7-pentyloxycarbonyl-D-arginine; |
| Compound #47 | N-(2,6-Dichloropurin-9-yl)-7-pentyloxycarbonyl-L-arginine; |
| Compound #48 | N-(2-Amino, 6-N, N-Dimethylaminopurin-9-yl)-5-pentanol; |
| Compound #49 | N-(6-dimethylamino-8-methylthiopurin-9-yl) 5-pentanol; |
| Compound #50 | N-(6-dimethylamino-8-methylthiopurin-9-yl) 7-pentoxycarbonyl-D-arginine; |
| Compound #51 | N-(6-methoxypurin-9-yl) 5-pentanol; |
| Compound #52 | N-(6-methoxypurin-9-yl) 7-pentoxycarbonyl-D-arginine; |
| Compound #53 | N-(2-chloro-6-methoxypurin-9-yl)-7-pentyloxycarbonyl-D-arginine; |
| Compound #54 | N-(6-dimethylaminopurin-9-yl) 7-pentoxycarbonyl-D-ornithine; |
| Compound #55 | N-(6-dimethylaminopurin-9-yl) 7-pentoxycarbonyl-L-ornithine; |
| Compound #56 | N-(6-dimethylaminopurin-9-yl) 7-pentoxycarbonyl-L-valine; |
| Compound #57 | N-(6-dimethylamino-9-yl) 7-pentoxycarbonyl-D-valine; |
| Compound #58 | N(N,N-dimethylaminopurin-9-yl)-7-pentyloxycarbonylethylamine hydrochloride; |
| Compound #59 | N-(6-Mercaptopurin-9-yl)-pentanol; |
| Compound #60 | N-(6,-N-Methylthiopurin-9-yl)-pentanol; |
| Compound #61 | N-(6-chloropurin-9-yl) 4-butanol; |
| Compound #62 | N-(6-dimethylaminopurin-9-yl) 4-butanol; |
| Compound #63 | N-(6-dimethylaminopurin-9-yl)-6-butoxycarbonyl-D-arginine; |
| Compound #64 | N-(6-dimethylaminopurin-9-yl)-6-butoxycarbonyl-L-arginine; |
| Compound #65 | N-(6-chloropurin-9-yl)-6-hexanol; |
| Compound #66 | N-(6-N,N-dimethylaminopurin-9-yl)-6-hexanol; |
| Compound #67 | N-(6-N,N-dimethylaminopurin-9-yl)-8-hexyloxycarbonyl-D-arginine; |
| Compound #68 | N(6-N,N-dimethylaminopurine-9-yl)-8-hexyloxycarbonyl-L-arginine; |
| Compound #69 | cis-(N-6-hydroxypurin-9-yl)-4-methyl-cyclohexyl-methanol; |
| Compound #70 | cis-(N-6-hydroxypurin-9-yl)-4-methyl-cyclohexyl-methyloxycarbonyl-D-arginine; |
| Compound #71 | trans-(N-6-hydroxypurin-9-yl)-4-methyl-cyclohexyl-methyloxycarbonyl-D-arginine; |
| Compound #72 | N-(6-N,N dimethylaminopurin-9-yl)-5-pentylamine hydrochloride salt; |
| Compound #73 | N-(6-methylaziridinepurinyl-9-yl)-7-pentyloxycarbonyl-L-arginine; |
| Compound #74 | (2S,4S)-2-(N,N-Dimethylaminopurin-9-yl)-4-hydroxymethyl-1,3-dioxolane; |
| Compound #75 | (1S,3R) and (1R,3S)-1-(N-6-Dimethylaminopurin-9-yl)methyl-3-cyclopentane methanol; |
| Compound #76 | (1S,3R) and (1R,3S)-1-(N-6-Dimethylaminopurin-9-yl)methyl-3-(methyloxycarbonyl-D-arginine) cyclopentane; |
| Compound #77 | N,N-(6-Dimethylaminopurin-9-yl)-7-ethylaminoethanol; |
| Compound #78 | N,N-(6-Dimethylaminopurin-9-yl)-7-ethylaminoethoxycarbonyl-D-arginine; |
| Compound #79 | N,N-(6-Dimethylaminopurin-9-yl)-7-ethylaminoethoxycarbonyl-L-arginine; |
| Compound #80 | 5-(N-6-Dimethylaminopurin-9-yl)-3-pentyn-1-ol; |
| Compound #81 | 5-(N-6-Dimethylaminopurin-9-yl)-3-pentynyl-1-oxycarbonyl-L-arginine; |
| Compound #82 | N,N-(6-Dimethylaminopurin-9-yl)-7-thioethoxy-ethanol; |
| Compound #83 | N,N-(6-Dimethylaminopurin-9-yl)-7-thioethoxy-ethoxycarbonyl-L-arginine; |
| Compound #84 | (2S,4S) and (2R,4R)-2-(N,N-Dimethylaminopurin-9-yl)-4-(methoxycarbonyl-D-arginine)-1,3-oxathiolane; |
| Compound #85 | N,N-(6-Dimethylaminopurin-9-yl)-7-ethoxy-ethoxyethanol; |
| Compound #86 | N,N-(6-Dimethylaminopurin-9-yl)-7-ethoxy-ethoxycarbonyl-D-arginine; |
| Compound #87 | N,N-(6-Dimethylaminopurin-9-yl)-7-ethoxy-ethoxycarbonyl-L-arginine; and |
| Compound #88 | N-(6-Dimethylamino-8-bromopurin-9-yl)-5-pentanol. |

More preferably, the compound of the present invention is selected from:

| | |
|---|---|
| Compound #III | N-(6-Chloropurin-9-yl)-5-pentanol |
| Compound #V | N-(6-N,N-Dimethylaminopurin-9-yl)-pentanol |
| Compound #1 | N, N-Dimethylaminopurinyl Pentoxycarbonyl D-Arginine |
| Compound #2 | N,N-Dimethylaminopurinyl Pentoxycarbonyl L-Arginine |
| Compound #3 | N-Monomethylaminopurinyl Pentoxycarbonyl D-Arginine |
| Compound #3a | N-(6-N-Methyl-Aminopurin-9-yl)-pentanol |
| Compound#5 | Aminopurinyl Pentoxycarbonyl D-Arginine |
| Compound #5a | N-(6-Aminopurin-9-Yl) 5-Pentanol |
| Compound #6 | Aminopurinyl Pentoxycarbonyl L-Arginine |
| Compound #7 | Hydrazinopurinyl Pentoxycarbonyl D-Arginine |
| Compound #7a | N-(6-Hydrazinopurin-9-yl) 5-Pentanol |
| Compound #8 | Hydrazinopurinyl Pentoxycarbonyl L-Arginine; |
| Compound #11 | Hydroxypurinyl Pentoxycarbonyl D-Arginine; |
| Compound #19 | N-9-purinyl-5-pentanol; |
| Compound #20 | N-9-purinyl-7-pentyloxycarbonyl-D-arginine; |
| Compound #51 | N-(6-methoxypurin-9-yl) 5-pentanol; |
| Compound #59 | N-(6-Mercaptopurin-9-yl)-pentanol; and |
| Compound #60 | N-(6,-N-Methylthiopurin-9-yl)-pentanol. |

Most preferably, the compound of the present invention is N,N-(6-dimethylaminopurin-9-yl)-7-pentoxycarbonyl-D-arginine.

The following abbreviations and definitions are used herein:

PHA—phytohemagglutinin
ConA—concanavalin A
CY—cyclophosphamide

PWM—pokeweed mitogen
LPS—lipopolysaccharide
DEAD—diethylazodicarboxylate
PBS—phosphate buffered saline
TBDPSCl—tert-butyldiphenylsilyl chloride
CTX—Cytoxan The term "conservative substitution" as employed herein refers to modifications and substitutions of amino acids which are conservative ones, i.e. those having a minimal influence on the secondary structure and hydropathic nature of the amino acid or peptide. These include substitutions such as those described by Dayhoff in the Atlas of Protein Sequence and Structure 5, 1978, and by Argos in EMBO J., 8, 779–785, 1989. For example, amino acids belonging to the following groups represent conservative changes: ala, pro, gly, glu, asp, gln, asn, ser, thr; cys, ser, tyr, thr; val, ile, leu, met, ala, phe; lys, arg, his; and phe, tyr, trp, his. The preferred substitutions also include substitutions of D-isomers for the corresponding L-amino acids.

It has been surprisingly discovered that contrary to the well-established prior art, hypoxanthine or other naturally occurring purine bases such as adenine or guanine need not be used in the design of an immunostimulant of the type similar to ST 789. In fact replacement of hypoxanthine with a 6-substituted purine base that does not occur in biological systems can provide an equal or even greater degree of immunostimulation. Further, it has been surprisingly discovered that the amino acid need not be of the (natural) L-configuration.

It will be recognized that the designation of a naturally occurring amino acid does not preclude the use of racemic mixtures or D-enantiomers and in one aspect of the invention, it is especially preferred to use amino acids in the D-configuration.

It has surprisingly been discovered that the compounds of the invention possess in vitro and in vivo activity to increase the number of cytotoxic T lymphocytes in the mammal being treated.

It has further been discovered that the compounds of the present invention are surprisingly active against tumor growth. The compounds of this invention represents a non-toxic substitute to levamisole in the treatment of malignant melanoma.

When tested in mice against a control group, the compounds of the present invention significantly inhibit tumor growth when used in combination with cyclophosphamide or 5-fluorouracil, particularly against mammary and colon carcinoma respectively.

The compounds of the present invention may be prepared by the use of synthetic methods well known in the art. Thus, for example, it is possible to follow the synthetic procedure described by R. Stradi et al. in Il Farmaco, 45, 39–47, 1990, with the provision that the chlorine atom from the chloropurine intermediate must be displaced by an appropriate substituent other than hydroxyl. However, it is preferred to carry out a modification of this synthetic procedure, as outlined in the following examples, wherein the purine ring is already constructed by use of 6-chloropurine as a starting material. This avoids the need to build the purine ring and thereby provides a more efficient and higher yield preparation of the desired immunostimulant. This preferred synthetic pathway is outlined in Scheme 1.

In Scheme 1, $R_4'$ which is $(CH_{0-2})_{1-8}$—O—CO—$X^{12}$ as defined above, is reacted with a protecting group in the presence of a base such as NaH/THF to produce compound V. L represents a leaving group well known to those skilled in the art. Any suitable leaving group can be used. Pg is a protecting group well known in the art. Any suitable protecting group can be used.

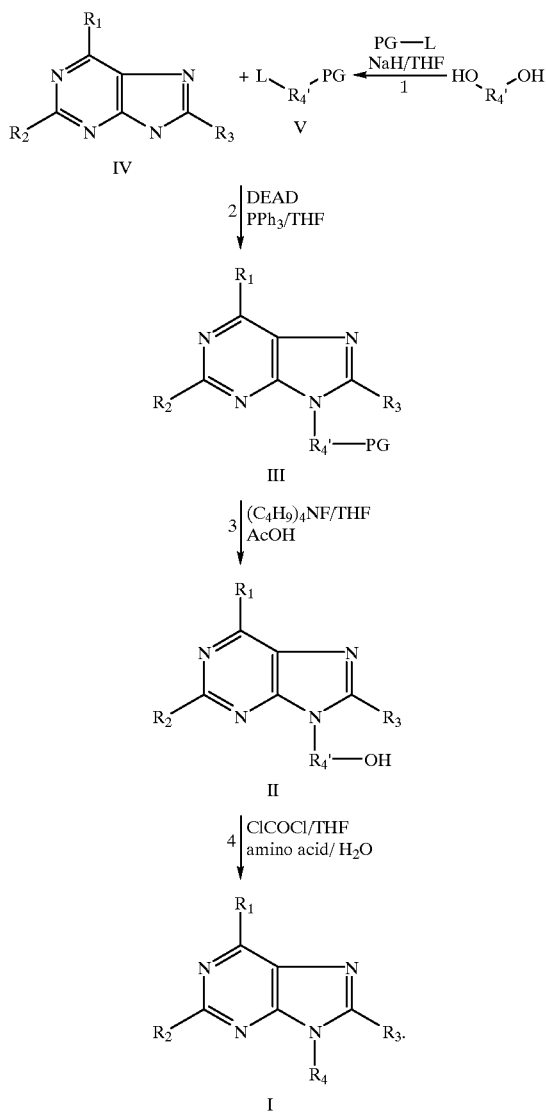

Compound V is coupled with compound IV, for example, in the presence of DEAD and PPh$_3$/THF to yield compound III. Compound IV can be prepared using known techniques in the art. As well, $R_1$ can be added before this step or at a later step using techniques well known in the art.

Compound III is deprotected by using methodology well known to those skilled in the art, for example, with $(C_4H_9)_4$NF/THF and AcOH for a OTBDPS protecting group, to yield compound II. This compound is further optionally reacted with an amino acid or a peptide group of 1–8 amino acids in length, for example, in the presence of ClCOCl/THF and H$_2$O. The resultant compound is a compound of formula I.

Those skilled in the art will appreciate that compounds of formula 1 wherein $R_4$ is not an amino acid or peptide chain can be synthesized by utilizing steps 1 to 3 without the addition step 4.

It will be appreciated by those skilled in the art that the compounds of the present invention include all pharmaceutically acceptable derivatives and analogues thereof, as well as all isomers and enantiomers.

Another aspect of the invention is the use of the compounds of formula I or pharmaceutical preparations for the manufacture of a medicament.

Another aspect of the invention is the method of treatment of a mammal, preferably a human, comprising the step of administering a compound of formula I, a pharmaceutical composition, or a pharmaceutically acceptable derivative thereof for the treatment of immune deficiency or control of tumor growth.

It will be appreciated by those skilled in the art that the reference herein to treatment extends to prophylaxis as well as treatment of established infections or symptoms and therefore includes control of tumor outgrowth.

It will be further appreciated that the amount of a compound of the invention required for use in treatment will vary not only with the particular compound selected but also with the route of administration, the nature of the condition being treated and the age and condition of the patient and will be ultimately at the discretion of the attendant physician or veterinarian.

In general, however, a suitable dose will be in the range from about 0.1 to about 250 mg/kg of body weight per day. Preferably, doses will range from about 1 to about 100 mg/kg/day. More preferably between about 2 to about 20 mg/kg. Most preferably about 2.5 mg/kg. Still, most preferably about 450 mg/m$^2$.

The desired dose may conveniently be presented in a single dose or as divided doses administered at appropriate intervals, for example as two, three, four or more subdoses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound. This may be achieved, for example, by the intravenous injection of a solution of the active ingredient, optionally in saline, or administered as a bolus. Desirable blood levels may be maintained by a continuous infusion or by intermittent infusions.

While it is possible that, for use in therapy, a compound of the invention may be administered as the raw chemical, it is preferable to present the active ingredient as a pharmaceutical formulation.

The invention thus further provides a pharmaceutical formulation comprising a compound of formula (I) or a pharmaceutically acceptable derivative thereof together with one or more pharmaceutically acceptable carriers thereof and, optionally, other therapeutic ingredients. The carrier(s) must be "acceptable" in the sense of being compatible with the other ingredients of the formulation and not deleterious to the recipient thereof.

Pharmaceutical formulations include those suitable for topical, oral, rectal, nasal, or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

For topical administration to the epidermis, the compounds according to the invention may be formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Pharmaceutical formulations suitable for oral administration may conveniently be presented as discrete units such as capsules, cachets, or tablets. Each pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

When desired, the above described formulations adapted to give sustained release of the active ingredient may be employed.

The compounds of the invention may also be used in combination with other therapeutic agents, for example, other immuomodulators or tumor control agents.

The invention thus provides, in a further aspect, a combination comprising a compound of formula (I) or a physiologically acceptable derivative thereof together with another therapeutically active agent.

Such therapeutically active agents include cytotoxic agents used to treat tumors. Such cytotoxic agents include cyclophosphamide, or 5-fluorouracil (5-FU).

Preferably, cyclophosphamide doses used in the treatment of tumors range from about 10 to 1000 mg/m$^2$. Morepreferably, from about 100 to about 500 mg/m$^2$. Most preferably, about 350 mg/m$^2$/day.

Also preferably, 5-fluorouracil doses used in the treatment of tumors ranges from about 0.1 to about 250 mg/kg. Preferably, between about 1 to about 50 mg/kg. More preferably, between about 5 to about 20 mg/kg. Most preferably, at about 12 mg/kg (500 mg/m$^2$).

As will be recognized by people skilled in the art of cancer therapy, such doses will vary with the type of malignancy being treated, the stage of the disease, the responsiveness of the, tumor, etc.

The combinations referred to above may conveniently be presented for use in the form of a pharmaceutical composition and thus pharmaceutical composition comprising a combination as defined above together with a pharmaceutically acceptable carrier thereof comprise a further aspect of the invention.

The individual components of such combinations may be administered either sequentially or simultaneously in separate or combined pharmaceutical formulations.

When the compound of formula (I) or a pharmaceutically acceptable derivative thereof is used in combination with a second therapeutic agent, the dose of each compound may be either the same or differ from that when the compound is used alone. Appropriate doses will be readily appreciated by those skilled in the art.

In a further embodiment of the invention, there is provided a method of treatment of immune deficiencies or for the control of tumor growth comprising the step of administering a pharmaceutically acceptable amount of a compound of the invention.

Preferably, such tumors include malignant melanoma, mammary and colon carcinoma.

More preferably, there is provided a method for the treatment of mammary carcinoma comprising the step of administering a pharmaceutically acceptable amount of a compound of the invention, in combination with cyclophosphamide.

Most preferably, there is provided a method for the treatment of colon carcinoma comprising the step of administering a pharmaceutically acceptable amount of a compound of the invention, in combination with 5-fluorouracil.

The invention will be further described by the following examples which are not intended to limit the invention in any way. All temperatures are in degrees Celsius.

EXAMPLES

The compounds of formula I were synthesized and tested for immunological activity using the procedures outlined below.

Example 1a Synthesis of N,N-Dimethylaminopurinyl Pentoxycarbonyl D-Arginine

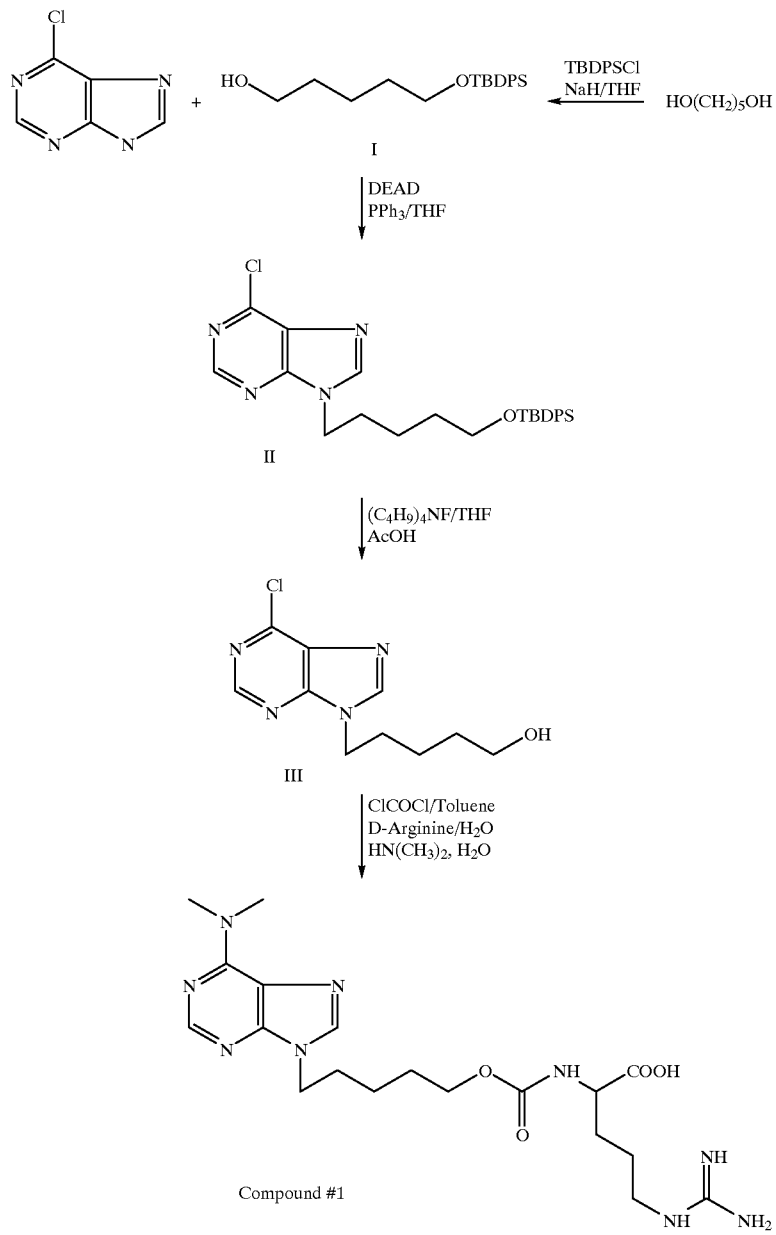

Step 1
a) Synthesis of protected 1,5-pentanediol 4.0 g., 36.3 mmole of pentanediol was dissolved in 75 ml dry tetrahydrofuran and stirred under argon flow. Sodium hydride (1.4 g., 57.8 mmole) was added and the suspension was stirred for 30 minutes, and then tert-butyldiphenylsilyl chloride (8.0 ml, 30.8 mmole) dissolved in 25 ml dry tetrahydrofuran was added dropwise to the diol solution. The reaction was stirred at ambient temperature and under argon overnight. The suspension was then poured onto 100 ml ether. The etheral suspension was washed with 10% potassium carbonate (100 ml), brine (100 ml) and dried with magnesium sulfate. Removal of the solvent in vacuo gave 10.3 g., 30.1 mmole of product in 98% yield which was used without further purification.

b) Coupling of Compound I with 6-chloropurine

To a stirred solution of triphenylphosphine (4.7 g., 17.9 mmole), and 6-chloropurine (2.3 g., 15.1 mmole) in 100 ml dry tetrahydrofuran, under argon flow, was added diethylazodicarboxylate (DEAD, 2.8 ml, 17.9 mmole). After 10 minutes, compound I (4.7 g., 13.7 mmole) dissolved in 20 ml dry tetrahydrofuran was added dropwise to the reaction, which was then stirred at ambient temperature and under argon overnight. The solvent was removed in vacuo, and the crude product was purified by flash silica gel chromatography using 30% ethyl acetate-hexane as eluent (R=0.30). The product, compound II, 3,7 g., 7.6 mmole, was obtained in 55% yield as a colorless oil.

Step 2
Removal of silyl protecting group 2.3 g, 4.4 mmole of compound II was dissolved in 40 ml dry tetrahydrofuran and stirred under argon flow. Tetrabutylammonium fluoride (5.3 ml, 5.1 mmole) was added and the reaction was stirred at ambient temperature and under argon overnight. To the solution was added glacial acetic acid (90.31 ml. 5.3 mmole) and the solvent was removed in vacuo. The crude product was purified by flash silica gel chromatography using 10% methanol-ethyl acetate as eluent (Rf=0.20). The product was taken up in minimal methylene chloride and filtered through celite to remove silica. The solvent was removed in vacuo, and the product dried, giving compound III, 1.0 g. 4.2 mmole, in 95% yield.

Step 3
Coupling of compound III with D-arginine 1.0 g., 4.2 mmole of 6-chloropurinyl pentanol, compound III, was dissolved in 75 ml dry tetrahydrofuran and stirred under argon flow. Toluenic phosgene (4.4 ml., 8.3 mmole) was added and the reaction was monitored by TLC (developed in methanol) and continued until the intermediate chloroformate was the predominant product (6–10 hours). The solvent was removed in vacuo, and the residue was taken up in 50 ml. dry tetrahydrofuran. D-arginine (0.94 g., 5.4 mmole), dissolved in 5 ml. water, was added to the chloroformate suspension. Another 5 ml. aliquot of water was used to rinse the beaker which contained the arginine solution, and then added to the reaction. The reaction was stirred overnight at ambient temperature, and then extracted with toluene (60 ml.). The toluene was back extracted with water (60 ml.) and the combined aqueous portions were brought to slightly alkaline pH by the addition of 5% sodium bicarbonate. Water was removed in vacuo and the residue was dissolved in methanol (10 ml.). After filtration, the methanolic solution was added dropwise to 500 ml vigorously stirred acetone. The precipitate was collected by filtration and washed several times with acetone. The filtrate contained unreacted III. The precipitate was dried, and then dissolved in water (50 ml.). to the aqueous solution was added dimethylamine (40% aqueous solution, 5.0 ml, 40 mmole) and the reaction was stirred for 3 hours at ambient temperature. The solvent was removed in vacuo and the crude product was purified by flash silica gel chromatography, using methanol as eluent (Rf=0.25). The combined product fractions were reduced in volume (approximately 5 ml) and stored at 4° C. for 2 hours. The solution was centrifuged for 10 minutes (375×g) to remove silica, and the supernatant was added dropwise to 500 ml vigorously stirred ether. The precipitate was collected by filtration and dried to give N,N-dimethylaminopurinyl pentoxycarbonyl D-arginine, compound #1, 0.79 g., 1.8 mmole in 43% yield.

mp (softens 119° C.)=123°–125° C. Rf silica (methanol)= 0.30; $^1$HNMR (DMSO-$d_6$, 300 Mhz, δ in ppm); 9.40 (1H, br, s, COOH); 8.20 (1H, s, purine); 8.15 (1H, s, purine); 8.0–7.3 (4H, b, guanidine); 6.33 (1H, d, N$\underline{H}$); 4.13 (2H, t, N—C$\underline{H}_2$); 3.86 (2H,t, O—C$\underline{H}_2$); 3.63 (1H, m, C$^\alpha \underline{H}$); 3.36 (6H, S, b, N—(C$\underline{H}_3)_2$); 3.02 (2H, b, C$^\delta$H); 1.8–1.2 (10H, m, C$^\beta \underline{H}$, C$^\gamma \underline{H}$,—(C$\underline{H}_2)_3$—). MS (high-resolution FAB, glycerol) m/e, 450.25780; calculated for M+H$^+$, ($C_{19}H_{32}O_4N_9$), 450.25773.

Example 1b
Alternative Synthesis of N,N-Dimethylaminopurinyl Pentoxycarbonyl D-Arginine—Compound #1

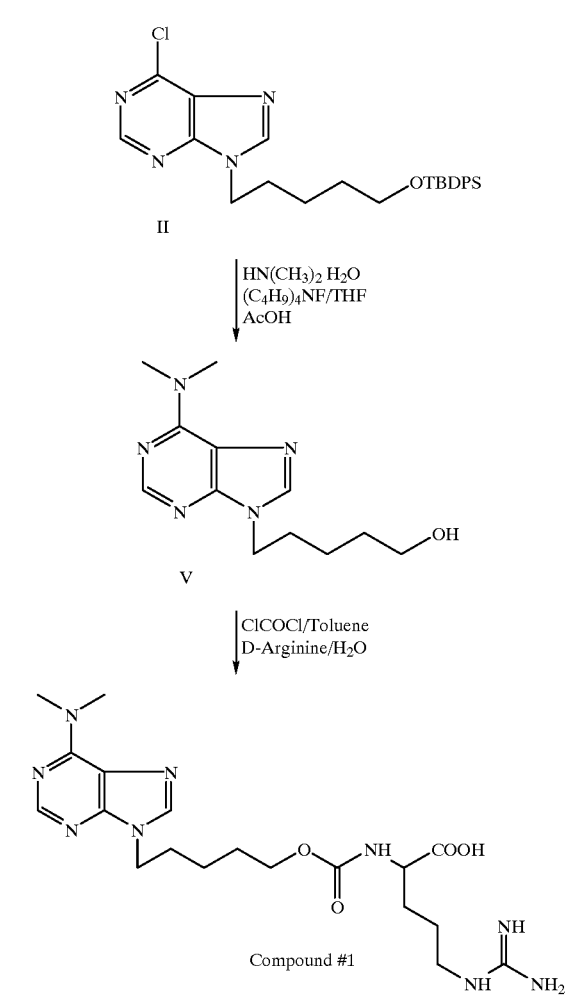

Compound #1

Step 1
A modified synthesis of compound #1 was undertaken by reaction of protected 6-chloropurinyl pentanol, compound II (prepared as described in example 1a) with aqueous dimethylamine, followed by deprotection to yield compound V, and coupling with D-arginine (the coupling reaction is as described in example 1a) to give the product. The spectral and chromatographic properties were identical to the product obtained from the synthesis described in example 1a.

A typical example of the reaction of protected 6-chloropurinyl pentanol, compound II, with dimethylamine is as follows; to 0.13 g., 0.26 mmole of compound II dissolved in 20 ml tetrahydrofuran was added dimethylamine (40% aqueous solution, 0.5 ml, 10.0 mmole). The reaction was stirred for 18 hours at ambient temperature, and the solvent was removed in vacuo. the crude product was purified by flash silica gel chromatography, using 50% ethyl acetate-hexane as eluent (Rf=0.27). The product compound V, 0.12 g. 0.30 mmole, was obtained in 94% yield.

Example 2
Synthesis of N,N-Dimethylaminopurinyl Pentoxycarbonyl L-Arginine—Compound #2

The L-enantiomer of compound #1, compound #2, was synthesized as described above in example 1b to give 50 mg. of product as a white solid.

mp (softens 118° C.)=123°–125° C. Spectral properties were identical with compound #1.

Example 3
Synthesis of N-Monomethylaminopurinyl Pentoxycarbonyl D-Arginine—Compound #3

Compound #3 was synthesized as described above in example 1b, except that dimethylamine was replaced with methylamine (40% aqueous solution) to give 6-methylaminopurinyl pentanol compound #3a. This was then coupled with D-arginine, as described in example 1a to give 32 mg. of product.

mp (softens at 127° C.)=133° C. Rf silica (methanol)=0.20; $^1$HNMR (DMSO-$d_6$, 300 Mhz, δ in ppm); 9.30 (1H, b, COO$\underline{H}$), 8.21 (1H, s, purine); 8.13 (1H, s, purine); 7.8–7.2 (4H, b, guanidine); 6.29 (1H, d, N$\underline{H}$); 4.13 (2H, t, N—C$\underline{H_2}$); 3.86 (2H, t, O—C$\underline{H_2}$); 3.61 (1H, m, C$^\alpha\underline{H}$); 3.17 (1H, m, CH$_3$—N—$\underline{H}$); 3.02 (3H, b, HN—C$\underline{H_3}$); 2.97 (2H, b, C$^\delta\underline{H}$); 1.9–1.2 (10H, m, C$^\beta\underline{H}$, C$^\gamma\underline{H}$, —(C$\underline{H_2}$)$_3$—).

Example 4
Synthesis of N-Monomethylaminopurinyl Pentoxycarbonyl L-Arginine—Compound #4

The L-enantiomer of compound #3 and compound #4, was synthesized as described above in example 3 to give 44 mg. of product as a white solid.

mp (softens at 123° C.)=132°–134° C. Rf silica (methanol)=0.20. Spectral properties were identical with compound #3.

Example 5
Synthesis of Aminopurinyl Pentoxycarbonyl D-Arginine—Compound #5

Compound #5 was synthesized as described above in example 1b except that protected 6-chloropurinyl pentanol, compound II, was reacted with ammonia gas instead of dimethylamine. The 6-aminopurinyl (adenine) product was thus deprotected to give the alcohol compound #5a. This was then coupled with D-arginine to give 260 mg. of product as a white solid. A typical example of the reaction of compound II with ammonia is as follows; 0.42 g, 0.88 mmole of compound II was dissolved in 75 ml absolute ethanol, and the solution was placed on an ice bath. Ammonia gas was bubbled through the chilled solution for 10 minutes, and the saturated solution was transferred to a bomb (150 ml cylinder). Ammonia gas was bubbled through the solution for another minute, the bomb sealed, and the bomb was heated overnight in a 120° C. oil bath. Solvent was removed in vacuo, yielding 0.40 g., 0.88 mmole of product in 95% yield. This product was used without further purification. Characteristics of compound #5;

mp(softens 143° C.)=150° C. Rf silica (methanol)=0.20; $^1$HNMR (DMSO-$d_6$, 300 Mhz, δ in ppm); 9.40 (1H, b, COO $\underline{H}$); 8.14 (1H, s, purine); 8.13 (1H, s, purine); 8.0–7.0 (6H, m, guanidine, —N$\underline{H_2}$); 6.36 (1H, b, N$\underline{H}$); 4.13 (2H, t, N—C$\underline{H_2}$); 3.87 (2H, t, O—C$\underline{H_2}$); 3.65 (1H, m, C$^\alpha\underline{H}$); 3.03 (2H, b, C$^\delta\underline{H}$); 1.9–1.2 (10H, m, C$^\beta\underline{H}$, C$^\gamma\underline{H}$, —(CH$_2$)$_3$—).

Example 6
Synthesis of Aminopurinyl Pentoxycarbonyl L-Arginine—Compound #6

The L-enantiomer of compound #5, compound #6, was synthesized as described above in example 5 to give 93 mg of product as a white solid.

mp (softens at 143° C.=153°–155° C. Rf silica (methanol)=0.22; Spectral properties were identical with compound #5.

Example 7
Synthesis of Hydrazinopurinyl Pentoxycarbonyl D-Arginine—Compound #7

Compound #7 was synthesized as described above in example 1a, except that dimethylamine was replaced with hydrazine from the corresponding alcohol compound #7a. Thus, in a typical example, 50 mg, 0.11 mmole of 6-chloropurinyl pentoxycarbonyl D-arginine, dissolved in 5 ml 95% ethanol, was reacted with hydrazine hydrate (12 μl, 0.40 mmole) at ambient temperature overnight. The reaction was then slowly cooled to 0° C. for 3 hours, and the resulting crystals were collected by filtration, and washed with cold ethanol. The white solid product, 32 mg., 0.07 mmole, was obtained in 65% yield.

mp(softens 130° C.)=134° C. Rf silica (methanol)=0.27; $^1$HNMR (DMSO-$d_6$, 300 Mhz, δ in ppm); 9.20 (1H, b, COO $\underline{H}$); 8.23 (1H, s, purine); 8.14 (1H, s, purine); 7.4 (3H, b, guanidine); 6.6 (2H, b, N$\underline{H_2}$); 6.43 (1H, d, N$\underline{H}$); 4.14 (2H, t, N—C$\underline{H_2}$); 3.87 (2H, t, O—C$\underline{H_2}$); 3.64 (1H, m, C$^\alpha\underline{H}$); 3.04 (2H, b, C$^\delta\underline{H}$); 1.8–1.3 (10H, m, C$^\beta\underline{H}$, C$^\gamma\underline{H}$, —(C$\underline{H_2}$)$_3$—).

Example 8
Synthesis of Hydrazinopurinyl Pentoxycarbonyl L-Arginine—Compound #8

The L-enantiomer of compound #7, compound #8, was synthesized as described in example 7 to give 40 mg of product as a white solid.

mp (softens at 130° C.=134° C. Rf silica (methanol)=0.27; Spectral properties were identical with compound #7.

Example 9
Synthesis of Chloropurinyl Pentoxycarbonyl D-Arginine—Compound #9

Compound #9 was synthesized by the coupling reaction of 6-chloropurinyl pentanol, compound III , with D-arginine, as described in example 1a (with omission of the addition of dimethylamiuje after the coupling reaction). This gave 622 mg of product as a white solid.

mp(softens 137° C.)=145°–148° C. Rf silica (methanol)=0.35; $^1$HNMR (DMSO-$d_6$, 300 Mhz, δ in ppm); 9.15 (1H, b, COO$\underline{H}$); 8.78 (1H, s, purine); 8.74 (1H, s, purine); 7.8–7.2 (4H, b, guanidine); 6.33 (1H, d, N$\underline{H}$); 4.29 (2H, t, N—C$\underline{H_2}$); 3.88 (2H, t, O—C$\underline{H_2}$); 3.64 (1H, m, C$^\alpha\underline{H}$); 3.04 (2H, b, C$^\delta\underline{H}$); 1.95–1.20 (10H, m, C$^\beta\underline{H}$, C$^\gamma\underline{H}$, —(C$\underline{H_2}$)$_3$—).

Example 10
Synthesis of Chloropurinyl Pentoxycarbonyl L-Arginine—Compound #10

The L-enantiomer of compound #9, compound #10, was synthesized as described above in example 9 to give 65 mg of product as a white solid.

mp (softens at 137° C.)=143–146° C. Rf silica (methanol)=0.26; Spectral properties were identical with compound #9.

Example 11
Synthesis of Hydroxypurinyl Pentoxycarbonyl D-Arginine—Compound #11

Compound #11 was synthesized as described in example 9 above except that the 6-chloropurinyl pentanol intermediate, compound III, was first subjected to base catalyzed hydrolysis to yield 6-hydroxypurinyl (hypoxanthine) pentanol compound #11a prior to coupling with D-arginine. Thus, in a typical example, 398 mg, 1.7 mmole of compound III was dissolved in 25 ml of water. Sodium hydroxide (1.0 m, 3.4 ml) was added, and the reaction was refluxed for 90 minutes. Upon cooling, the reaction was acidified (5% hydrochloric acid), the solvent removed in vacuo, and the crude product purified by flash silica gel chromatography using 30% methanol-ethyl acetate as eluent (Rf=0.32). The product, compound #11a, 290 mg, 1.3 mmole, was obtained in 79% yield as a white solid. Subsequent coupling with D-arginine gave 148 mg of compound #11 as a white solid.

mp(softens 163° C.)=182° C. Rf silica (methanol)=0.22; $^1$HNMR (DMSO-d6, 300 Mhz, δ in ppm); 9.28 (1H, b, COO$\underline{H}$); 8.10 (1H, s, purine); 8.04 (1H, s, purine); 7.8–7.2 (4H, b, guanidine); 6.38 (1H, d, N$\underline{H}$); 4.32 (1H, b, O$\underline{H}$); 4.13 (2H, t, N—C$\underline{H}_2$); 3.87 (2H, t, O—C$\underline{H}_2$); 3.61 (1H, m, C$^\alpha\underline{H}$); 3.04 (2H, b, C$^\delta\underline{H}$); 1.8–1.1 (10H, m, C$^\beta$H, C$^\gamma\underline{H}$, —(CH$_2$)$_3$—).

Example 12
Synthesis of Mercaptopurinyl Pentoxycarbonyl D-Arginine—Compound #12

Compound #12 was synthesized as described in example 1a, except that dimethylamine was replaced with thiourea. Thus, in a typical example, 80 mg, 0.18 mmole of 6-chloropurinyl pentoxycarbonyl D-arginine, dissolved in 5 ml absolute ethanol was reacted with thiourea, 16 mg, 0.21 mmole, under reflux for 5 hours. The reaction was then stored at 0° C. overnight and the resulting crystals were filtered and washed with cold absolute ethanol. The product was recrystallized from absolute ethanol to give a white solid, 48 mg, 0.11 mmole in 61% yield.

mp(softens 180° C.)=200° C. Rf silica (methanol)=0.50; $^1$HNMR (DMSO-d6, 300 Mhz, δ in ppm); 9.15 (1H, b, COO$\underline{H}$); 8.29 (1H, s, purine); 8.18 (1H, s, purine); 7.5–7.3 (4H, b, guanidine); 6.39 (1H, d, N$\underline{H}$); 4.13 (2H, t, N—C$\underline{H}_2$); 3.87 (2H, t, O—C$\underline{H}_2$); 3.65 (1H, m, C$^\alpha\underline{H}$); 3.04 (2H, b, C$^\delta\underline{H}$); 1.90–1.23 (10H, m, C$^\beta\underline{H}$, C$^\gamma\underline{H}$, —(CH$_2$)$_3$—).

Example 13
Synthesis of Mercaptopurinyl Pentoxycarbonyl L-Arginine—Compound #13

The L-enantiomer of compound #12, compound #13, was synthesized as described in example 12 to give 42 mg of product as a white solid.

mp (softens at 180° C.=200° C. Rf silica (methanol)=0.50; Spectral properties were identical with compound #12.

Example 14
Synthesis of N,N-Dimethylaminopurinyl Pentoxycarbonyl Glycine—Compound #14

Compound #14 was synthesized as described above in example 1b except that the coupling reaction was undertaken on smaller scale, with glycine, 68 mg, 0.91 mmole, instead of arginine and the free base of glycine was generated in situ by the addition of 3 equivalents of sodium carbonate (relative to the alcohol). The crude product was purified by flash silica gel chromatography, using 50% methanol-ethyl acetate as eluent (Rf=0.35). Silica was removed by dissolving the product in methylene chloride, followed by filtration. Removal of solvent in vacuo gave 30 mg of product as a white solid.

mp(softens 100° C.)=126° C. Rf silica (1:1 methanol-ethyl acetate)=0.35; $^1$HNMR (DMSO-d6, 300 Mhz, δ in ppm); 8.20 (s, 1H, purine); 8.16 (s, 1H, purine); 6.05 (1H, t, N$\underline{H}$); 4.14 (2H, t, N—C$\underline{H}_2$); 3.86 (2H, t, O—C$\underline{H}_2$); 3.33 (6H, s, b, N—(C$\underline{H}_3$)$_2$—); 3.18 (2H, d, C$^\alpha\underline{H}$); 1.80 (2H, m, C$\underline{H}_2$); 1.55 (2H, m, C$\underline{H}_2$); 1.26 (2H, m, C$\underline{H}_2$);

Example 15
N,N-(6-Dimethylaminopurin-9-yl)-7'-ethoxy-ethoxycarbonyl-D-arginine—Compound #15

Step 1
N,N-(6-Dimethylaminopurin-9-yl)-5-ethoxyethoxy-t-butyldiphenylsilane To a solution of alcohol (0.201 g, 1 eq) in anh. THF (2.9 ml), at room temperature, under argon, were added successively 6-chloropurine (90 mg, 0.58 mmol), Ph$_3$P (0.199 g, 1.3 eq) and DEAD (0.12 ml, 1.3 eq). The yellow solution was stirred at room temperature for 15 hours. The THF was evaporated and the residue was chromatographed (6:4, Hexanes/EtOAc) to give a mixture of (EtO$_2$CNH)$_2$ and the coupled purine. To a solution of this mixture in THF (6 ml), at room temperature, was added 40% Me$_2$NH/H$_2$O (0.70 ml, 10 eq). The solution was stirred at room temperature for 45 minutes and was then poured in sat. aq. NaHCO$_3$/CH$_2$Cl$_2$. The phases were separated and the aqueous phase was extracted with CH$_2$Cl$_2$(2×). The combined organic extracts were dried over MgSO$_4$, the solids filtered and the solvents evaporated. The residue was purified by flash chromatography (silica gel, 2:8 Hex/AcOEt) to give 0.16 g (55%) of the coupled dimethyl amino purine.

Step 2
N,N-(6-Dimethylaminopurin-9-yl)-5-ethoxyethanol—compound #85

To a solution of the silane (0.16 g, 0.32 mmol) in anh. THF (3.2 ml), at room temperature, under argon, was added nBu$_4$NF 1.0 M/THF (0.32 ml, 1.1 eq). The solution was stirred at room temperature for 3 hours and the solvent was evaporated in vacuo. The residue was immediately purified by flash chromatography (silica gel, 4:1 AcOEt/MeOH) to give 72 mg (89%) of the alcohol compound #85 as a clear oil.

$^1$HNMR (CDCl$_3$): δ 8.29 (s, 1H, purine), 7.80 (s, 1H, purine), 4.33 (t, 2H, C$\underline{H}_2$), 3.82 (t, 2H, C$\underline{H}_2$), 3.68 (t, 2H, C$\underline{H}_2$), 3.55 (t, 2H, C$\underline{H}_2$), 3.50 (m, 6H, N(C$\underline{H}_3$)$_2$).

Step 3
N,N-(6-Dimethylaminopurin-9-yl)-7-ethoxyethoxycarbonyl-D-arginine—Compound #15

To a solution of the alcohol, compound #85 (72 mg, 0.29 mmol) in anh. THF (4.8 ml), at room temperature, under argon, was added COCl$_2$/Toluene 1.93 M (0.30 ml, 2 eq) and the solution was stirred at room temperature for 5 hours. The THF was evaporated in vacuo and the residue was redissolved in THF (3.6 ml). To this solution was added a solution of D-arginine in water (65 mg, 1.3 eq/0.5 ml H₂O). The flask containing the D-arginine solution was rinsed with 0.5 ml H₂O and the reaction mixture was stirred at room temperature for 15 hours. It was then extracted with toluene and the toluene phase was back-extracted with H₂O. The combined aqueous layers were brought to pH 7.5–8.0 (NaHCO₃ 5%) and the water was evaporated. The residue was purified by flash chromatography (silica gel, 100% MeOH). The fractions containing the compound were evaporated and the residue was dissolved in a minimum quantity of MeOH. Et₂O was then added and the solvents were decanted to give a white gum that was dried under high vacuum. The compound was obtained as a white solid (42 mg, 33%).

$^1$H NMR (DMSO-d$_6$): δ 8.25 (s, 1H, H-2-purine), 8.14 (s, 1H, H-8-purine), 6.5 (bd, 1H, N$\underline{H}$), 4.37 (t, 2H, C$\underline{H}_2$ linker), 4.03 (m, 2H, C$\underline{H}_2$ linker), 3.81 (m, 2H, C$\underline{H}_2$ linker), 3.72 (m, 1H, C$^\alpha\underline{H}$), 3.60 (m, 2H, CH₂ linker), 3.55–3.89 (m, 6H, N(C$\underline{H}_3$)₂), 3.05 (m, 2H, C$^\alpha\underline{H}_2$), 1.78–1.39 (m, 4H, C$^\beta\underline{H}_2$, C$^\gamma\underline{H}_2$).

Example 16
(2S,4S)-2-(N,N-dimethylaminopurin-9-yl)-4-(methyloxycarbonyl-D-arginine)-1,3-dioxolane—Compound #16

Step 1
(4S)-2,2-dimethyl-1,3-dioxolane-4-t-butyldiphenylsilylmethanol

To a solution of (4s)-2,2-dimethyl-1,3-dioxolane-4-methanol (1 g, 7.57 mmols) in anh. CH₂Cl₂ (76 ml), at room temperature, under argon, were added successively imidazole (1.03 g., 2 eq) and t-BuPh₂SiCl (1.95 ml, 1.1 eq). A white precipate formed immediately. This suspension was stirred at room temperature for 1 hour and then poured in sat. aq. NaHCO₃. The phases were separated and the aqueous layer was extracted with CH₂Cl₂ (2x). The combined organic extracts were dried over MgSO₄, the solids were filtered and the solvents evaporated to give 2.80 g (100%) of the silane as a clear oil.

Step 2
(2S)-3-t-Butyldiphenylsilylpropanetriol

To a solution of the silane (1.01 g, 2.73 mmols) in a 4:1 mixture of THF/H₂O (15 ml), at room temperature, was added TFAA (0.5 ml, 2.4 eq) and the solution was heated at 50° C. for 5 hours. It was then poured in sat. aq. NaHCO₃/CH₂Cl₂ and the phases were separated. The aqueous layer was extracted with CH₂Cl₂ (2x) and the combined organic extracts were dried over MgSO₄. The solvents were evaporated and the residue was purified by flash chromatography (silica gel, 1:1 Hex/EtOAc) to give 0.62 g. (70%) of the diol as a clear oil.

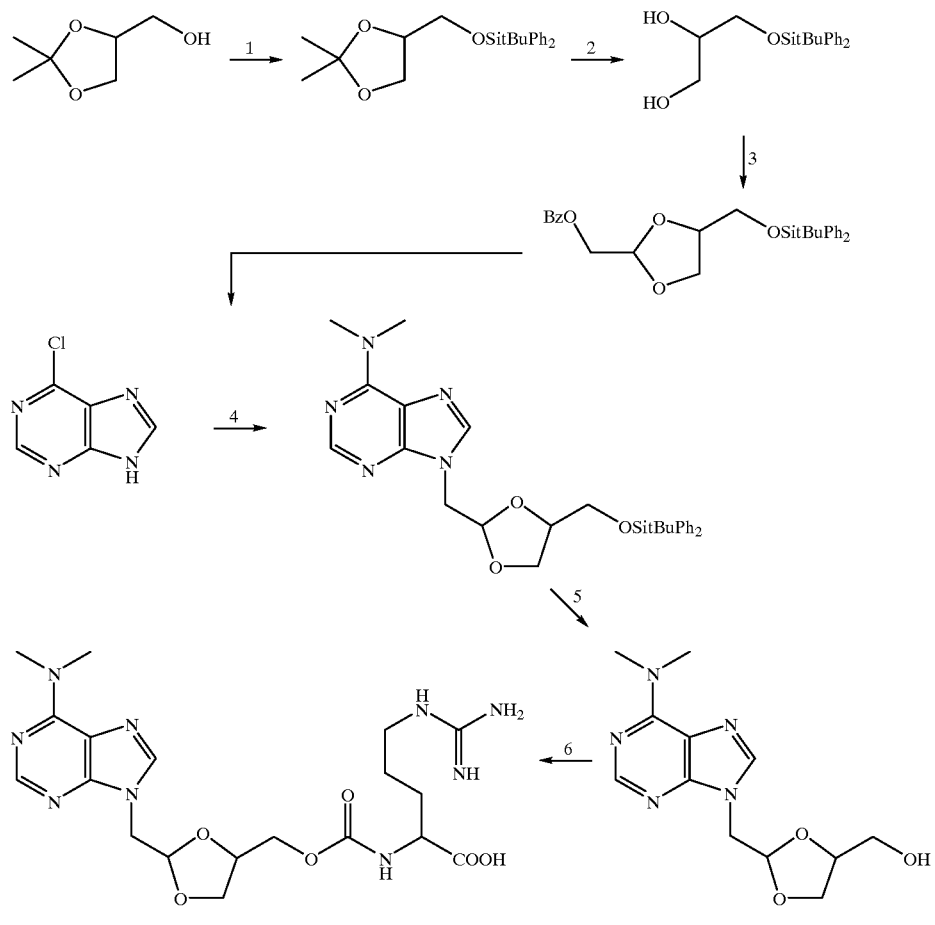

Compound #16

Step 3

(2S,4S)-2-benzoyloxymethyl-4-t-Butyldiphenylsilyloxymethyl-1,3-dioxolane

To a solution of the diol (0.62 g, 1.89 mmol) and of the aldehyde (0.31 g, 1eq) in anh. toluene (19 ml), at room temperature, under argon, was added a cat. amount of PPTS. The solution was refluxed for 18 hours, after which it was poured in sat. aq. NaHCO$_3$/CH$_2$Cl$_2$. The phases were separated and the aqueous layer was extracted with CH$_2$Cl$_2$ (2×). The combined organic extracts were dried over MgSO$_4$ and the solvents were evaporated. The residue was purified by flash chromatography (silica gel, 9:1 Hex/EtOAc) to give 0.49 g (55%) of a 5:1 (cis/trans) mixture of the dioxolanes.

Step 4

(2S,4S)-2-Hydroxymethyl-4-t-butyldiphenylsilyloxymethyl-1,3-dioxolane

To a solution of the benzoate (0.49 g, 1.03 mmol) in anh. MeOH (10.3 ml), at room temperature, under argon, was added MeONa/MeOH 4.37 M (24 μl, 0.1 eq). The solution was stirred for 18 hours after which it was poured in sat. aq. NH$_4$Cl/CH$_2$Cl$_2$. The phases were separated and the aqueous phase was extracted with CH$_2$Cl$_2$ (2×). The combined organic extracts were dried over MgSO$_4$, the solids were filtered and the solvents were evaporated. The residue was purified by flash chromatography (silica gel, 3:1 Hex/EtOAc) to give the cis-alcohol (0.26 g, 67%) as a clear oil.

Step 5

(2S,4S)-2-(N,N-dimethylaminopurin-9-yl)-4-t-butyldiphenylsilyloxymethyl-1,3-dioxolane The compound was prepared using a similar method as in Example 15, step 1.

Step 6

(2S,4R)-2-(N,N-dimethylaminopurin-9-yl)-4-hydroxymethyl-1,3-dioxolane

The compound was prepared using a similar method as in Example 15, step 2.

Purification: 10% MeoH/EtoAc $^1$HNMR (CDCl$_3$): δ 8.32 (s, 1H, purine), 7.75 (s, 1H, purine), 5.33 (dd, 1H, J=2.0, 6.6, H-2-dioxolane, 5.33 (bs, 1H, OH), 4.45 (dd, 1H, J=6.6, 14.3, C$\underline{H}_2$-purine), 4.20 (dd, 1H, J=2.0, 14.3, C$\underline{H}_2$-purine), 4.20 (m, 1H, H-4-dioxolane), 4.05 (d, 2H, J-7.2, H-5), 3.78 (d, 1H, J=13.0, C$\underline{H}_2$—OH) 3.53 (bs, 6H, (C$\underline{H}_3$)$_2$N), 3.40 (d, 1H, J-13.0, C$\underline{H}_2$—OH).

Step 7

(2S,4S)-2-(N,N-dimethylaminopurin-9-yl)-4-(methyloxycarbonyl-D-arginine)-1,3-dioxolane—Compound #16

The compound #16 was prepared using a similar method as in Example 15, step 3.

Purification: MeoH 100%

$^1$HNMR (DMSO-d$_6$): δ 8.43 (s, 1H, purine), 8.11 (s, 1H, purine), 6.6 (m, 1H, N$\underline{H}$), 5.28, (m, 1H, H-2-dioxolane), 4.39 (m, 2H, C$\underline{H}_2$-purine), 4.26 (m, 1H, H-4-dioxolane), 3.97–3.81 (m, 3H, C$^\alpha\underline{H}$, C$\underline{H}_2$—OCO-D-arginine), 3.71 (m, 2H, H-5-dioxolane), 3.39 (bs, 6H, (C$\underline{H}_3$)$_2$N), 3.07 (m, 2H, C$^\alpha\underline{H}_2$), 1.70–1.45 (m, 4H, C$^\beta\underline{H}_2$, C$^\gamma\underline{H}_2$).

Example 17

Synthesis of N-(6-Dimethylamino-8-bromopurinyl-Pentoxycarbonyl L-Arginine

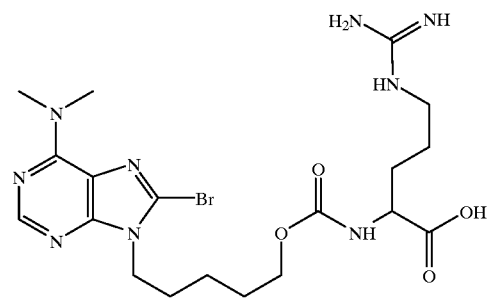

$^1$H NMR (DMSO-d$_6$, 400 Mhz, δ in ppm): 9.5 (1H, s, b, COO$\underline{H}$), 8.19 (1H, s, purine), 8.1–7.2 (4H, b, guanidine), 6.30 (1H, d, N$\underline{H}$), 4.11 (2H, t, N—C$\underline{H}_2$), 3.87 (2H, t, C$\underline{H}_2$—O), 3.64 (1H, m, C$^\alpha\underline{H}$), 3.39 (6H, s, b, N—(C$\underline{H}_3$)$_2$), 3.02 (2H, m, C$^\delta\underline{H}$), 1.8–1.2 (10H, m, C$^\beta\underline{H}$, C$^\gamma\underline{H}$, —(C$\underline{H}_2$)$_3$—).

m.p. (softens 115–118°)=124–127° C. R$_f$ silica (70% methanol-ethyl acetate)=0.25

Example 18

Synthesis of N-(6-dimethylamino-8-bromopurin-9-yl) 7-pentoxycarbonyl-D-arginine—Compound #18

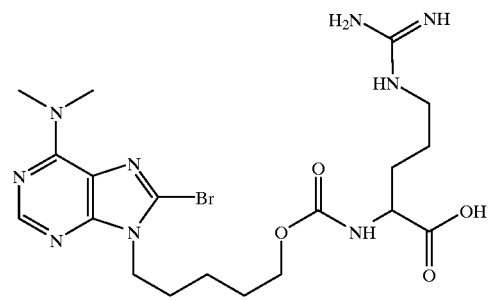

$^1$H NMR (DMSO-d$_6$, 400 MHz, δ in ppm); 9.08 (1H, br s, COO$\underline{H}$); 8.18 (1H, s, purine); 7.9–7.3 (4H, br s, guanidine); 6.34 (1H, d, N$\underline{H}$); 4.10 (2H, t, N—C$\underline{H}_2$); 3.86 (2H, m, O—C$\underline{H}_2$); 3.55 (1H, m, C$^\alpha\underline{H}$); 3.35 (br s, N—(C$\underline{H}_3$)$_2$); 3.03 (2H, m, C$^\delta\underline{H}_2$); 1.9–1.2 (10H, m, (C$\underline{H}_2$)$_3$, C$^\gamma\underline{H}_2$, C$^\beta\underline{H}_2$). m.p. (softens 116° C.)=122–125° C. R$_f$ silica (70% methanol-ethyl acetate)=0.25

Example 19

N-9-purinyl-5-pentanol—Compound #19

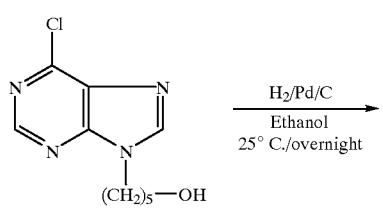

-continued

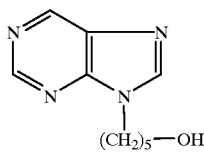

¹H NMR δ (CDCl₃ in ppm): 9.12 (s, 1H, purine), 8.96 (s, 1H, purine), 8.10 (s, 1H, purine), 4.30 (t, 2H, CH₂—O), 3.63 (t, 2H, CH₂—N), 1.97 (m, 3H, CH₂ and OH), 1.62 (m, 2H, CH₂), 1.47 (m, 2H, CH₂). ¹³C NMR (δ CDCl₃ in ppm): 153.09, 151.96, 149.15, 145.80, 134.60, 62.78, 44.38, 32.47, 30.27, 23.57. Purification 5% MeOH/AcOEt; R_f (silica) 0.29 (5% MeOH/AcOEt).

Example 20
N-9-purinyl-7-pentyloxycarbonyl-D-arginine

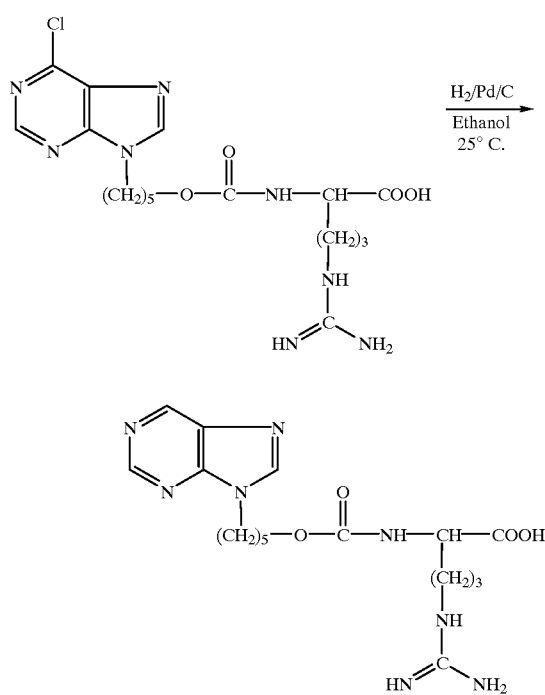

¹H NMR δ (DMSO in ppm): 9.10 (s, 1H, purine), 8.93 (s, 1H, purine), 8.64 (s, 1H, purine), 7.77 (bs, 4H, guanidine), 6.25 (bs, 1H, NH), 4.28 (t, 2H, CH₂—O—), 3.87 (t, 2H, CH₂—N), 3.58 (m, 1H, C^αH), 3.09 (m, 2H, CH₂—N), 1.20–1.90 (m, 10H, 5xCH₂). Purification: methanol; R_f (silica)=0.23 (methanol)

Example 21
N-9-purinyl-7-pentyloxycarbonyl-L-arginine—

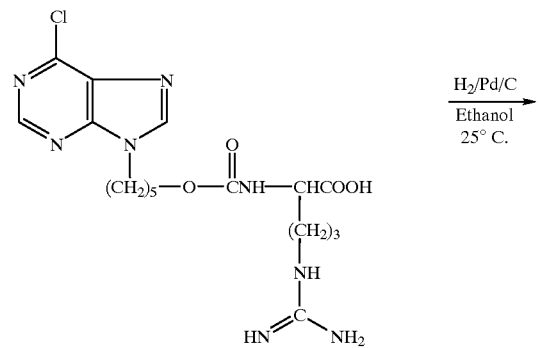

¹H NMR δ (DMSO in ppm): 9.13 (s, 1H, purine), 8.94 (s, 1H, purine), 8.66 (s, 1H, purine), 8.25 (bs, 1H, NH), 7.44 (bs, 3H, guanidine), 6.82 (bs, 1H, NH), 4.28 (t, 2H, CH₂—O), 3.88 (t, 2H, CH₂—N), 3.72 (m, 1H, C^αH), 3.07 (m, 2H, CH₂—N), 1.19–1.95 (m, 10H, 5xCH₂). ¹³C NMR (δ CD₃OD in ppm): 179.47, 159.21, 158.95, 153.79, 153.41, 140.07, 135.42, 66.06, 57.37, 45.38, 42.66, 31.88, 30.93, 30.11, 26.67, 24.65. Purification: methanol; R_f (silica)=0.23 (methanol)

Example 22
Synthesis of N,N-Dimethylaminopurinyl Pentoxycarbonyl L-Valyl L-Prolyl L-Leucine—

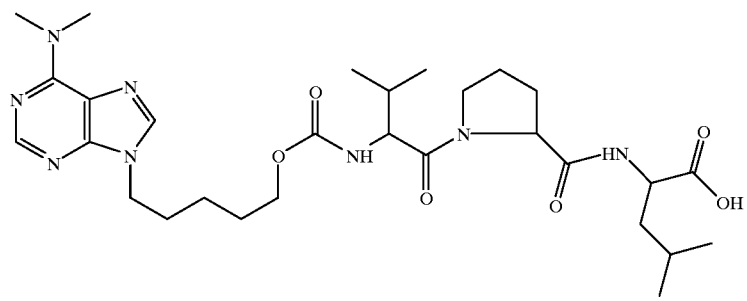

¹HNMR (CD₃OD, 400 MHz, δ in ppm) 8.22 (1H, S, purine); 8.05 (1H, s, purine); 4.60 (1H, t, C$^\alpha$H); 4.3–3.6 (8H, n, N—CH₂, C$^\delta$H₂, CH₂—O, 2 x C$^\alpha$H); 3.51 (6H, s, b, N—(CH₃)₂); 2.2–1.2 (14H, m, —(CH₂)₃—, 2 x C$^\beta$H₂, C$^\beta$H, C$^\gamma$H₂, C$^\gamma$H); 1.0–0.8 (12H, m, 2 x C$^\beta$-CH₃, 2 x C$^\gamma$-CH₃. m.p.=168° C. R$_f$ silica (40% methanol-ethyl acetate)=0.40

Example 23
Synthesis of N,N-Dimethylaminopurinyl Pentoxycarbonyl L-Isoleucyl L-Prolyl L-Isoleucine—Compound #23

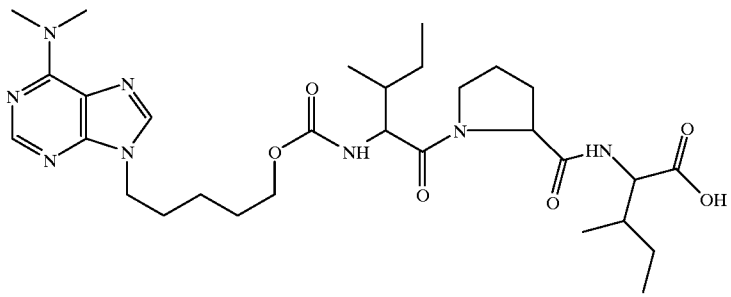

¹HNMR (CD₃OD, 400 MHz, δ in ppm); 8.21 (1H, s, purine); 8.03 (1H, s, purine); 4.62 (1 H, t, C$^\alpha$H); 4.22 (4H, m); 4.03 (2H, m); 3.89 (1H, m, C$^\alpha$H); 3.67 (1H, d, C$^\alpha$H); 3.50 (6H, s, b, N—(CH₃)₂); 2.1–1.0 (16H, m, —(CH₂)₃—, C$^\beta$H₂, 2 x C$^\beta$H, 3 x C$^\gamma$H₂); 0.95 (6H, d, 2 x C$^\beta$CH₃); 0.87 (6 H, t, 2 x C$^\gamma$-CH₃). m.p. (softens 83–86° C.)=93° C. R$_f$ silica (40% methanol-ethyl acetate)=0.35

Example 24
Synthesis of N-(6-Cyclopropylaminopurin-9-yl)-5-pentanol—Compound #24

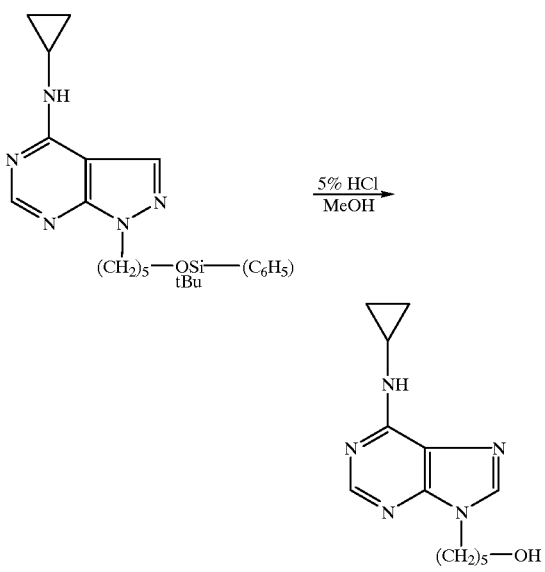

¹H NMR (δ CDCl₃ in ppm): 8.46 (s, 1H, purine), 7.77 (s, 1H, purine), 6.42 (bs, 1H, NH), 4.22 (t, 2H, CH₂), 3.09 (bs, 1H, OH), 1.94 (m, 2H, CH₂), 1.63 (m, 2H, CH₂), 1.45 (m, 2H, CH₂), 0.94 (m, 2H, CH₂), 0.69 (m, 2H, CH₂). Colorless oily material; R$_f$=0.3 10% methanol/ethyl acetate; Mass spectrum: H⁺=262 (HRMS)

Example 25
Synthesis of N-(6-cyclopropylaminopurin-9-yl)-7-pentyloxycarbonyl-D-arginine—Compound #25

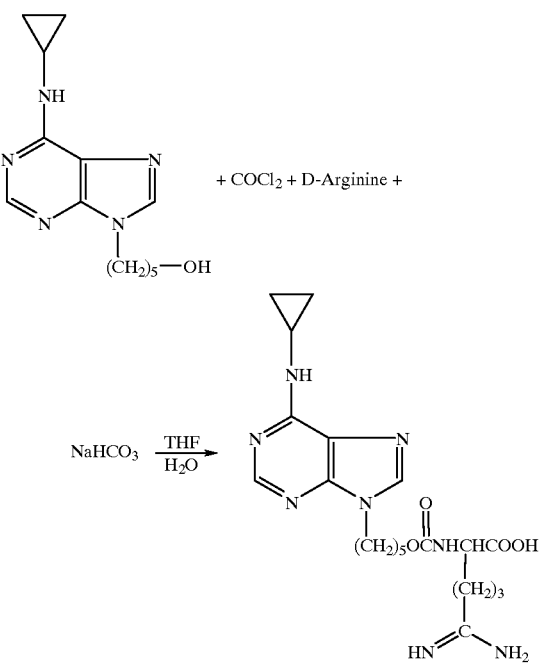

¹H NMR (δ DMSO in ppm): 8.22 (s, 1H, purine), 8.14 (s, 1H, purine), (bs, 4H, guanidine), 6.28 (d, 1H, NH), 4.13 (t, 2H, CH₂), 3.87 (m, 2H, CH₂), 3.62 (m, 1H, C$^\alpha$H), 3.02 (m, 2H, CH₂), 1.2–1.8 (m, 11H, 5xCH₂ and CH), 0.69 (m, 2H, CH₂), 0.67 (m, 2H, CH₂). ¹³C NMR (δ, DMSO in ppm): 175.53, 158.20, 157.63, 155.79, 152.62, 150.91, 141.03, 119.92, 63.69, 55.38, 43.12, 41.14, 30.10, 29.44, 28.49, 25.49, 24.38, 22.91, 6.78. m.p. softens 147° C. melts 151° C. R$_f$=0.34 (MeOH); Mass spectrum: H⁺=462 (HRMS)

Example 26
Synthesis of N-(6-cyclopropylaminopurin-9-yl)-7-pentyloxycarbonyl-L-arginine—Compound #26

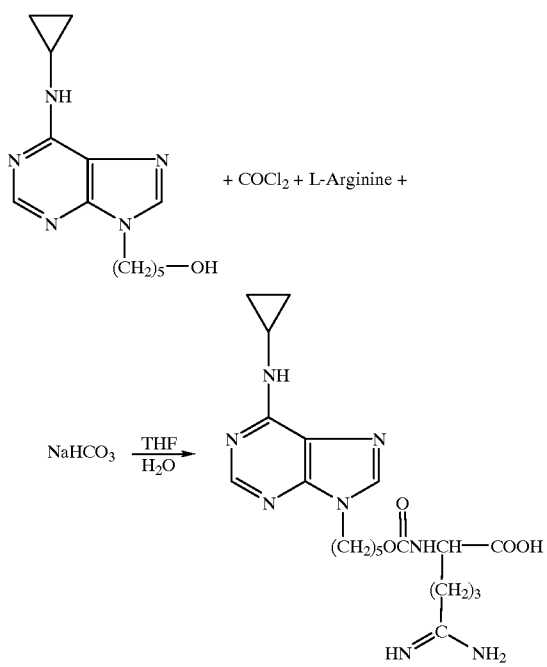

+ COCl$_2$ + L-Arginine +

NaHCO$_3$ $\xrightarrow{\text{THF}}$ H$_2$O

¹H NMR (δ DMSO in ppm): 8.23 (s, 1H, purine), 8.14 (s, 1H, purine), 7.51 (bs, 4H, guanidine), 6.31 (d, 1H, NH), 4.16 (t, 2H, CH$_2$), 3.87 (t, 2H, CH$_2$), 3.62 (m, 1H, C$^\alpha$H), 3.02 (m, 2H, CH$_2$), 1.2–1.85 (m, 11H, 5xCH$_2$ and CH), 0.72 (m, 2H, CH$_2$), 0.68 (m, 2H, CH$_2$). ¹³C NMR (δ, CD$_3$OD in ppm): 179.41, 159.19, 158.95, 157.66, 154.09, 151.00, 143.00, 121.10, 66.12, 57.34, 45.33, 42.67, 31.90, 31.25, 30.14, 26.63, 25.11, 24.61, 8.14. m.p. 144–146° C. R$_f$=0.35 (MeOH); Mass spectrum: M$^+$=462 (HRMS).

Example 27
Synthesis of N-(6-Azetidinepurin-9-yl)-5-pentanol—Compound #27

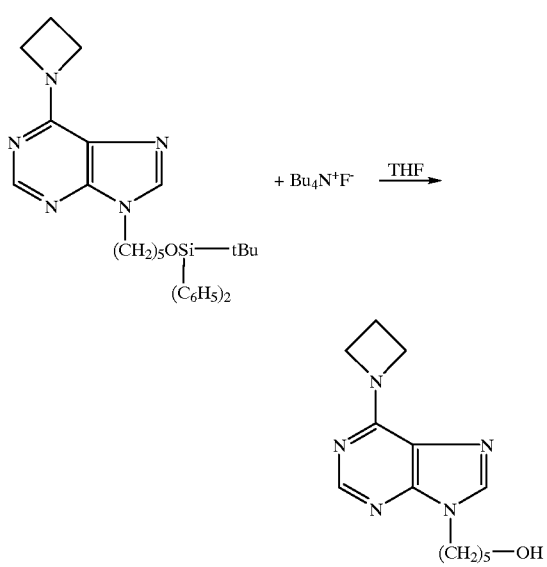

+ Bu$_4$N$^+$F$^-$ $\xrightarrow{\text{THF}}$

¹H NMR (δ, CDCl$_3$ in ppm): 8.25 (s, 1H, purine), 7.66 (s, 1H, purine), 4.44 (m, 4H, CH$_2$), 4.10 (t, 2H, CH$_2$), 3.55 (t, 2H, CH$_2$), 3.21 (bs, 1H, OH), 2.48 (m, 2H, CH$_2$), 1.84 (m, 2H, CH$_2$), 1.54 (m, 2H, CH$_2$), 1.38 (m, 2H, CH$_2$). ¹³C NMR (δ, CDCl$_3$ in ppm): 155.11, 153.42, 150.39, 140.37, 120.38, 62.79, 44.05, 32.57, 30.45, 30.22, 23.45, 18.23, 18.12. m.p.: 104–106° C. R$_f$=0.33 (10% MeOH/AcOEt); Mass spectrum: M$^+$=262 (HRMS).

Example 28

Synthesis of N-(6-Azetidinepurin-9-yl)-7-pentyloxycarbonyl-D-arginine—Compound #28

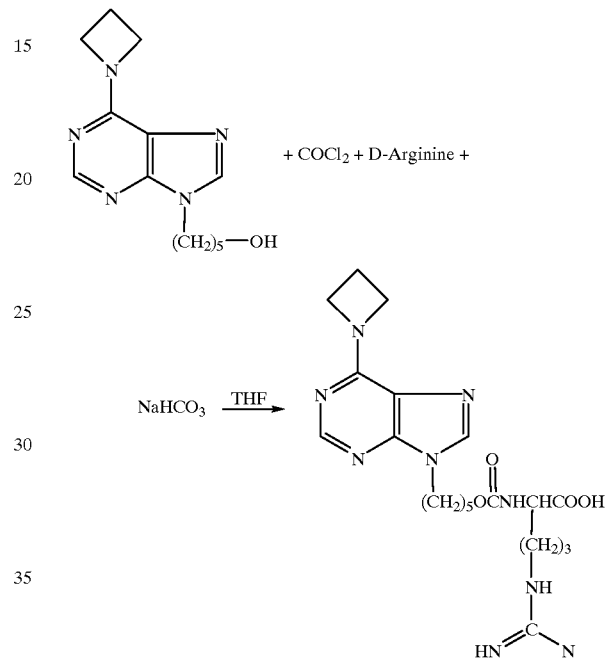

+ COCl$_2$ + D-Arginine +

NaHCO$_3$ $\xrightarrow{\text{THF}}$

¹H NMR (δ, CD$_3$OD in ppm): 7.96 (s, 1H, purine), 7.89 (s, 1H, purine), 4.27 (m, 4H, 2xCH$_2$), 4.02 (t, 2H, CH$_2$), 3.79 (m, 3H, CH$_2$ and C$^\alpha$H), 2.99 (m, 2H, CH$_2$), 2.32 (m, 2H, CH$_2$), 1.17–1.71 (m, 10H, 5xCH$_2$). ¹³C NMR (δ, CD$_3$OD in ppm): 181.56, 159.38, 159.14, 156.16, 153.89, 151.22, 143.21, 120.92, 66.30, 57.15, 48.71 45.24, 42.66, 31.51, 31.26, 30.15, 26.96, 24.64, 18.87. m.p.: 190–192° C. R$_f$: 0.25 (methanol); Mass spectrum: M$^+$=462 (HRMS)

Example 29

Synthesis of N-(6-Azetidinepurin-9-yl)-7-pentyloxycarbonyl-L-arginine—Compound #29

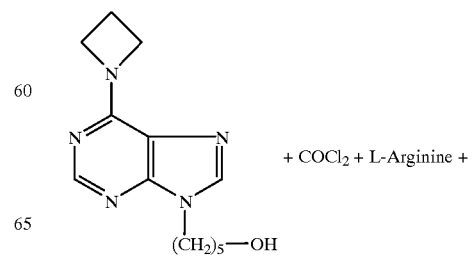

+ COCl$_2$ + L-Arginine +

-continued

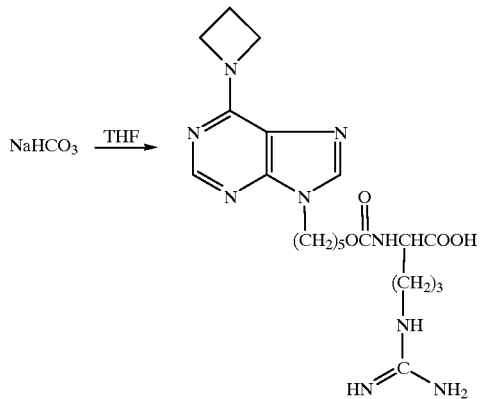

NaHCO₃ THF→

¹H NMR (δ, CD₃OD in ppm): 7.93 (s, 1H, purine), 7.88 (s, 1H, purine), 4.27 (m, 4H, 2xCH₂), 4.01 (t, 2H, CH₂), 3.79 (m, 3H, CH₂ and C^αH), 2.97 (m, 2H, CH₂), 2.32 (m, 2H, CH₂), 1.15–1.74 (m, 10H, 5xCH₂). ¹³C NMR (δ, CD₃OD in ppm): 179.44, 159.18, 158.95, 156.16, 153.89, 151.21, 143.20, 120.93, 66.12, 57.33, 48.69, 45.26, 42.65, 31.88, 31.33, 31.23, 30.16, 26.63, 24.61, 18.50. m.p.: (softens at 175° C.) melts at 187° C. R$_f$=0.27 (methanol); Mass spectrum: M⁺=462 (HRMS)

Example 30
Synthesis of trans-(N-6-chloropurin-9-yl)-4-methyl-cyclohexyl-methanol—Compound #30

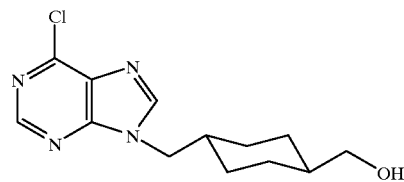

¹H NMR (CDCl₃, 400 MHz, δ in ppm); 8.73 (1H, s, purine); 8.05 (1H, s, purine); 4.12 (2H, d, N—CH₂); 3.43 (2H, d, O—CH₂); 1.89 (1H, m, CH); 1.84–1.64 (4H, m, C H₂-cyclohexane); 1.56 (1H, br s, OH); 1.45 (1H, m, CH); 1.14–0.85 (4H, m, CH₂-cyclohexane). m.p. (softens 176° C.)=178° C. R$_f$=0.4 (ethyl acetate)

Example 31
Synthesis of trans-(N-6-dimethylaminopurin-9-yl)-4-methyl-cyclohexyl-methanol—Compound #31

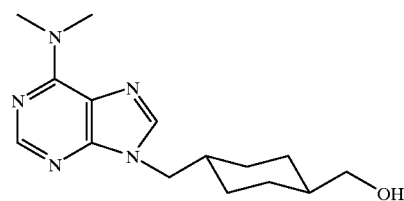

¹H NMR (CDCl₃, 300 MHz, δ in ppm); ; 8.29 (1H, s, purine); 7.63 (1H, s, purine); 3.97 (2H, d, N—CH₂); 3.49 ( 6H , br s, N—(CH₃)₂); 3.38 (2H, d, O—CH₂); 2.46 (1H, br s, OH); 1.84 (1H, br m, CH-cyclohexane); 1.71 (4H, m, 2 x CH₂-cyclohexane); 1.40 (1H, m, CH-cyclohexane); 0.90 (4H, m, CH₂-cyclohexane). ¹³C NMR (CDCl₃, 400 MHz, δ in ppm); 154.9, 152.3, 150.6, 138.7, 120.1, 68.2, 49.7, 40.2, 38.5, 38.2, 29.9, 28.6. m.p.=151–153° C. R$_f$=0.44 (10% methanol-ethyl acetate)

Example 32
Synthesis of trans-(N-6-dimethylaminopurin-9-yl)-4-methyl-cyclohexyl-methyloxycarbonyl-D-arginine—Compound #32

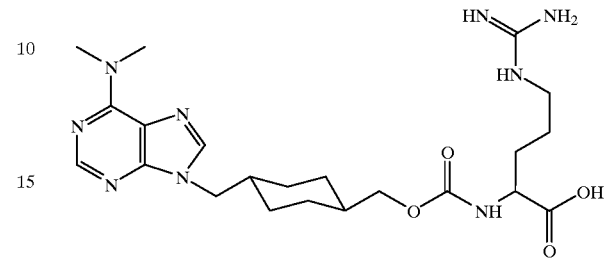

¹H NMR (DMSO-d₆, 400 MHz, δ in ppm); 9.4 (1H, br s, COOH); 8.19 (1H, s, purine); 8.11 (1H, s, purine); 8.0–7.2 (4H, br, guanidine); 6.28 (1H, d, NH); 3.98 (2H, d, N—C H₂); 3.69 (2H, d, O—CH₂); 3.61 (1H, m, C^αH); 3.43 (6H, br s, N—CH₃)₂); 3.00 (2H, br, C^δH₂); 1.9–0.8 (14H, m, C^β H₂, C^γH₂, 2 x CH-cyclohexane, 4 x CH₂-cyclohexane). ¹³C NMR (DMSO-d₆, 400 MHz, δ in ppm); 174.8, 156.8, 155.0, 153.8, 151.2, 150.0, 139.6, 118.7, 78.7, 67.9, 54.6, 48.2, 48.1, 37.1, 36.5, 29.3, 28.8, 27.8, 24.6. m.p. (softens 157° C.)=164–166° C. R$_f$=0.35 (methanol)

Example 33
Synthesis of trans-(N-6-hydroxypurin-9-yl)-4-methyl-cyclohexyl-methanol—Compound #33

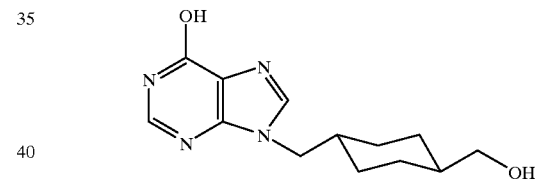

¹H NMR (CD₃OD, 400 MHz, δ in ppm); 8.05 (2H, s, purine); 4.10 (2H, d, N—CH₂); 3.35 (2H, d, O—CH₂); 2.0–0.9 (10 H, m, 2 x CH-cyclohexane, 4 x C H₂-cyclohexane) ¹³C NMR (CD₃OD, 400 MHz, δ in ppm); 156.7, 148.1, 144.1, 140.2, 122.7, 66.1, 48.7, 39.2, 37.5, 28.7, 27.6. m.p. >200° C. R$_f$=0.35 (20% methanol-ethyl acetate)

Example 34
Synthesis of trans-(N-6-methoxypurin-9-yl)-4-methyl-cyclohexyl-methanol—Compound #34

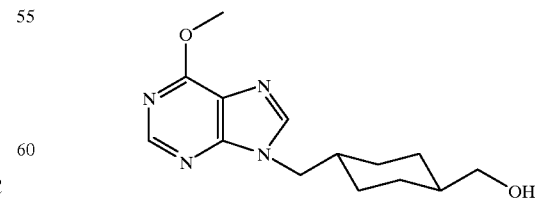

¹H NMR (CDCl₃, 300 MHz, δ in ppm); 8.52 (1H, s, purine); 7.84 (1H, s, purine); 4.17 (3H, s, O—CH₃); 4.12 (2H, d, N—CH₂); 3.43 (2H, d, O—CH₂); 1.89 (1H, m, CH); 1.84–1.64 (4H, m, CH₂-cyclohexane); 1.56 (1H, br s, OH);

1.45 (1H, m, CH); 1.14–0.85 (4H, m, CH$_2$-cyclohexane). m.p. (softens 159° C.)=162° C. R$_f$=0.25 (ethyl acetate)

Example 35

Synthesis of cis-(N-6-dimethylaminopurin-9-yl)-4-methyl-cyclohexyl-methanol—Compound#35

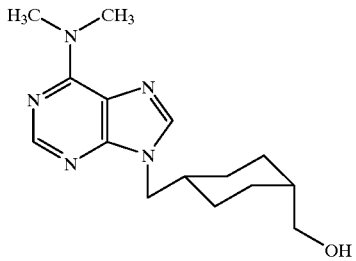

$^1$H NMR (CDCl$_3$, 300 MHz, δ in ppm); ; 8.31 (1H, s, purine); 7.66 (1H, s, purine); 4.08 (2H, d, N—CH$_2$); 3.55 (2H, d, O—CH$_2$); 3.50 (6H , br s, N—(CH$_3$)$_2$); 3.28 (1H, br s, OH); 2.12 (1H, m, CH); 1.67 (1H, m, CH); 1.5–1.3 (8H, m, CH$_2$-cyclohexane). $^{13}$C NMR (CDCl$_3$, 300 MHz, δ in ppm); 155.4, 152.7, 151.1, 139.1, 120.5, 65.9, 47.7, 39.1, 38.3, 36.3, 26.6, 25.4. m.p. 153–156° C. R$_f$=0.3 (10% methanol-ethyl acetate)

Example 36

Synthesis of cis-(N-6-dimethylaminopurin-9-yl)-4-methyl-cyclohexyl-methyloxycarbonyl-D-arginine—Compound #36

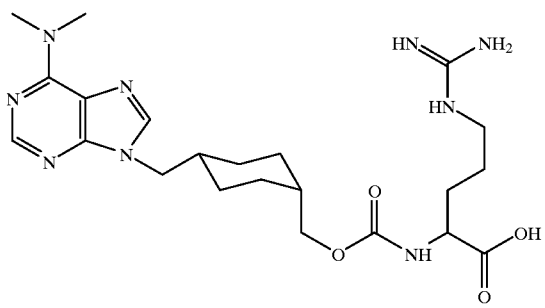

$^1$H NMR (DMSO-d$_6$, 400 MHz, δ in ppm); 9.28 (1H, br s, COOH); 8.19 (1H, s, purine); 8.13 (1h, s, purine); 8.0–7.2 (4H, br, guanidine); 6.34 (1H, d, NH); 4.10 (2H, d, N—CH$_2$); 3.85 (2H, d, O—CH$_2$); 3.65 (1H, m, C$^α$H); 3.44 (6H, br S, N—(CH$_3$)$_2$); 3.02 (2H, m, C$^δ$H$_2$); 2.09 (1H, m, CH); 1.8–1.2 (14H, m, C$^β$H$_2$, C$^γ$H$_2$, 2 x CH-cyclohexane, 4 x C H$_2$-cyclohexane). $^{13}$C NMR (DMSO-d$_6$, 400 MHz, δ in ppm); 175.2, 157.7, 155.2, 154.1, 151.8, 150.2, 139.9, 119.3, 66.4, 55.3, 46.1, 48.0, 34.9, 34.7, 29.9, 25.5, 25.1, 24.4. m.p. (softens 153° C.)=168–170° C. R$_f$=0.35 (methanol)

Example 37

Synthesis of N-(6-dimethylaminopurin-9-yl) 7-pentoxycarbonyl-D-citrulline—Compound #37

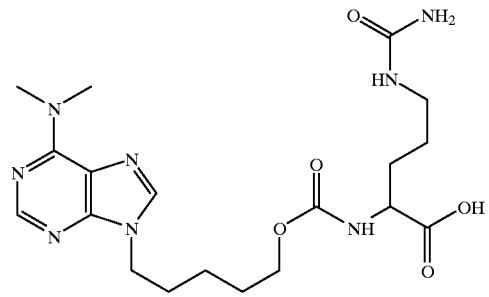

$^1$H NMR (DMSO-d$_6$, 400 MHz, δ in ppm); 8.19 (1H, s, purine); 8.15 (1H, s, purine); 6.21 (1H, d, NH); 6.11 (1H, s, NCO—NH); 5.42 (2H, s, NH$_2$) 4.14 (2H, t, N—CH$_2$); 3.86 (2H, m, O—CH$_2$); 3.56 (1H, m, C$^α$H); 3.35 (6H, br s, N—(C H$_3$)$_2$); 2.87 (2H, m, C$^δ$H$_2$); 1.9–1.2 (10H, m, (CH$_2$)$_3$, C$^γ$H$_2$, C$^β$H$_2$). $^{13}$C NMR (CD$_3$OD, 400 MHz, δ in ppm); 173.6, 158.4, 155.0, 153.8, 151.2, 149.7, 139.3, 118.7, 62.8, 54.8, 42.3, 37.4, 29.8, 28.5, 27.6, 25.7, 22.0. m.p. (softens 172–176° C.)=178–181° C. R$_f$=0.20 (40% methanol-ethyl acetate)

Example 38

Synthesis of N-(6-methylaziridinepurin-9-yl)-5-pentanol—Compound #38

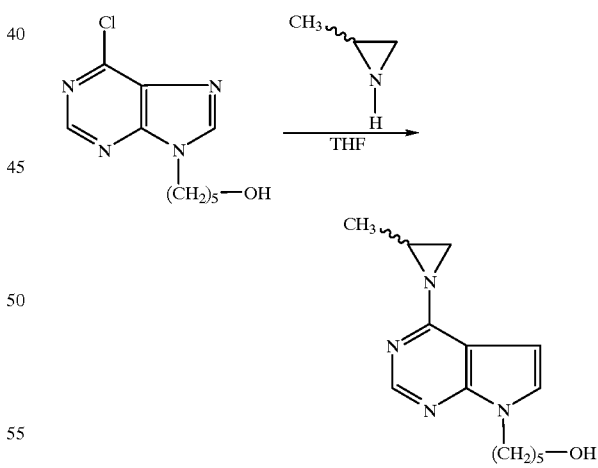

$^1$H NMR (δ, CDCl$_3$ in ppm): 8.54 (s, 1H, purine), 7.90 (s, 1H, purine), 4.22 (t, 2H, CH$_2$), 3.61 (t, 2H, CH$_2$), 2.78 (m, 1H, CH), 2.65 (d, 1H, CH$_2$), 2.40 (d, 1H, CH$_2$), 2.39 (bs, 1H, OH), 1.94 (m, 2H, CH$_2$), 1.59 (m, 2H, CH$_2$), 1.50 (d, 3H, CH$_3$), 1.40 (m, 2H, CH$_2$). $^{13}$C NMR (δ, CDCl$_3$ in ppm): 163.30, 152.99, 151.99, 142.80, 126.11, 62.81, 44.48, 35.97, 34.89, 32.51, 30.38, 23.50, 18.48. Low melting point. R$_f$=0.4 (20% MeOH/AcOEt); Mass spectrum: M$^+$=262

Example 39

Synthesis of racemic N-(6-methylaziridine purine-9-yl)-7-pentyloxycarbonyl-D-arginine—Compound #39

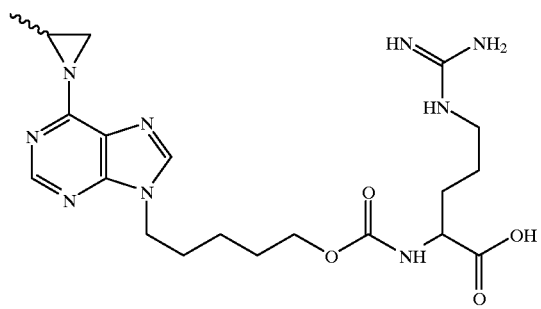

$^1$H NMR (CD$_3$OD in ppm): 8.29 (s, 1H, purine), 8.14 (s, 1H, purine), 4.10 (t, 2H, CH$_2$), 3.79 (m, 3H, 1xCH$_2$ and C$^\alpha$H), 2.97 (m, 2H, CH$_2$), 2.62 (m, 1H, CH), 2.45 (d, 1H, CH$_2$), 2.19 (d, 1H, CH$_2$), 1.2–1.76 (m, 13H, 5xCH$_2$ and 1xCH$_3$). m.p.: (softens at 190° C.) melts at 200° C. R$_f$: 0.4 (methanol); Mass spectrum: M$^+$=462

Example 40

N,N-(6-Dimethylaminopurinyl-9-yl)-7-thioethoxy-ethoxycarbonyl-D-arginine—Compound #40

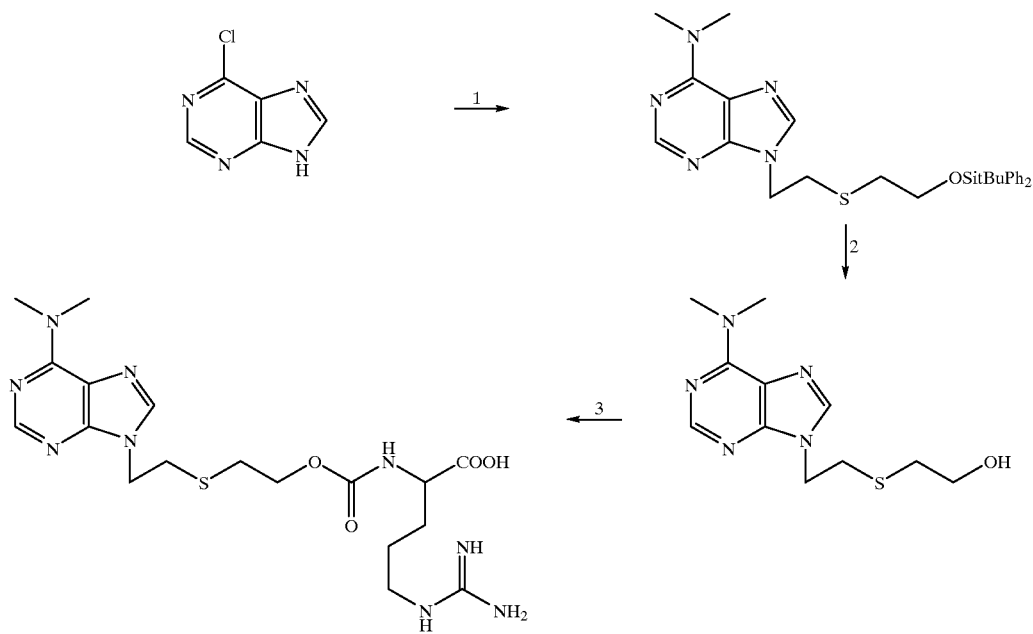

Example 41

Meta-(N-6-dimethylaminopurinyl-9-yl) methyl-benzyloxycarbonyl-D-arginine—Compound #41

Compound #41

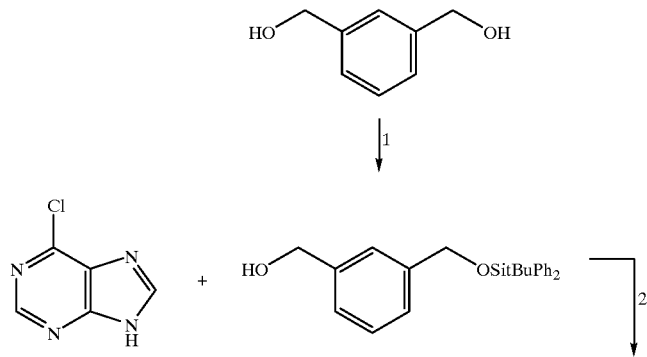

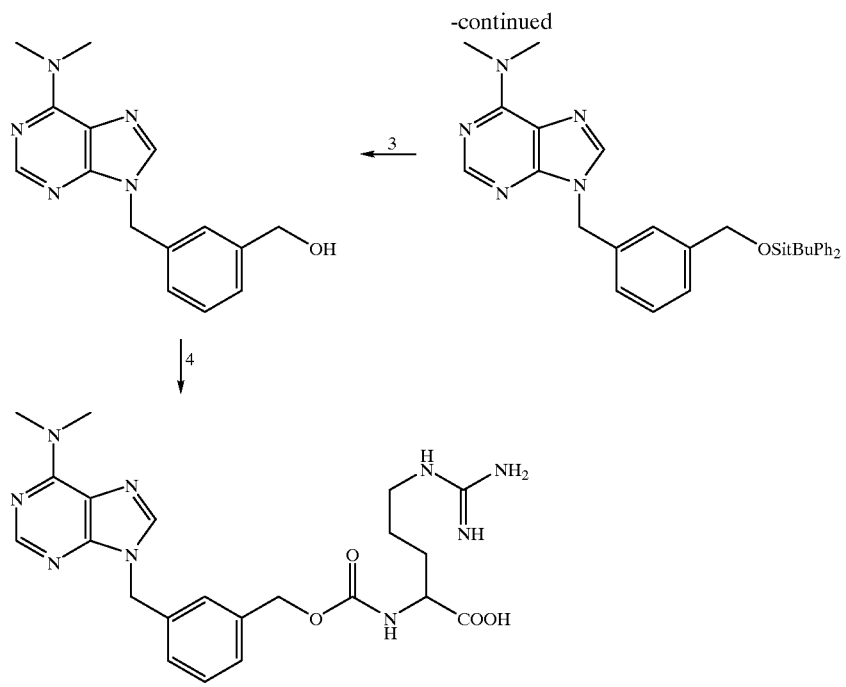
Example 42
5-(N-6-Dimethylaminopurinyl-9-yl)-3-pentynyl-1-oxycarbonyl-D-arginine—Compound #40
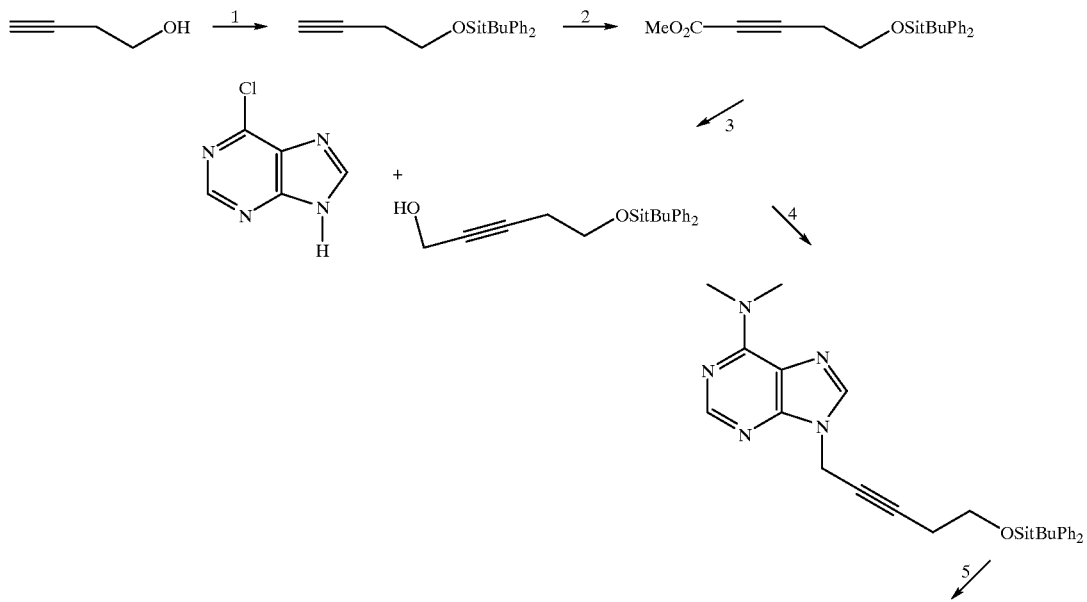

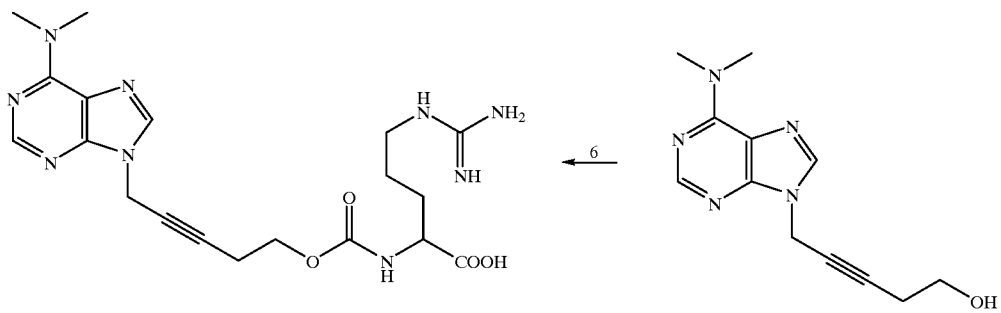

Example 43

Synthesis of Racemic N-[6-(1-methy-2-acetoxy)-ethylaminopurin-9-yl]-5-pentanol—Compound #43

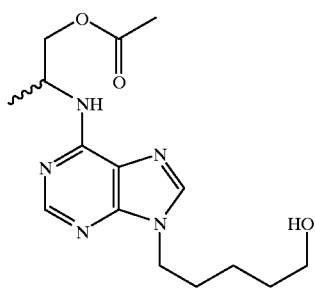

$^1$H NMR (δ, CDCl$_3$ in ppm): 8.36 (s, 1H, purine), 7.76 (s, 1H, purine), 6.58 (bs, 1H, NH), 5.18 (m, 1H, OH), 4.22 (t, 2H, CH$_2$), 3.92 (bs, 1H, CH), 3.63 (t, 2H, CH$_2$), 2.05 (s, 3H, CH$_3$), 1.3–1.9 (m, 4xCH$_2$, 1xCH$_3$). 173.04, 156,6, 155.8, 154.2, 142.8, 120.5, 71.66, 68.61, 63.10, 45.43, 33.54, 31.42, 24.54, 21.69, 18.25. Low melting point; R$_f$=0. 5 15% MeOH/AcOEt; Mass spectrum: M$^+$=322

Example 44

Synthesis of Racemic N-[6-(1-methyl-2-acetoxy), ethylaminopurin-9-yl]-7-pentyloxy-carbonyl-D-arginine—Compound #44

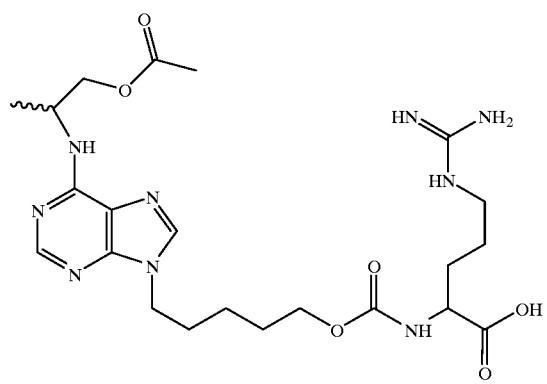

$^1$H NMR (δ, OD$_3$OD in ppm): mixture of isomers, 8.05 (s, 1H, purine), 7.89 (s, 1H, purine), 4.92 (m, 1H, CH), 4.03 (t, 2H, CH$_2$), 3.78 (m, 3H, CH$_2$ and c$^α$H), 3.46 (d, 2H, CH$_2$), 2.99 (m, 2H, CH$_2$), 1.8 (s, 3H, CH$_3$), 1.1–1.79 (m, 13H, 5xCH$_2$ and 1xCH$_3$). $^{13}$C NMR (δ, CD$_3$OD in ppm): mixture of isomers, 179.50, 159.19, 158.97, 156.88, 154.21, 154.14, 142.85, 142.75, 120.95, 68.13, 66.91, 66.11, 57.36, 45.32, 42.65, 31.89, 31.73, 31.25, 30.15, 30.04, 26.67, 24.61, 21.56, 18.09. m.p.: (softens at 177° C.) melts at 185° C. R$_f$: 0.35 (methanol); Mass spectrum: M$^+$=522.

Example 45

Synthesis of N-(2,6-Dichloropurin-9-yl)-5-pentanol—Compound #45

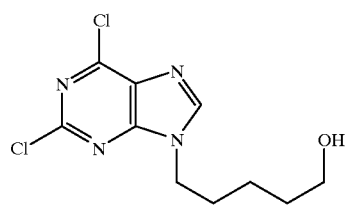

$^1$H NMR (δ, CDCl$_3$ in ppm): 8.11 (s, 1H, purine), 4.29 (t, 2H, CH$_2$), 3.66 (t, 2H, CH$_2$), 2.00 (m, 2H, CH$_2$), 1.64 (m, 2H, CH$_2$), 1.48 (m, 2H, CH$_2$), 1.3 (t, 1H, OH). $^{13}$C NMR (δ, CDCl$_3$ in ppm): 163.3, 150.2 149.3, 148.01, 128.00, 63.20, 44.80, 29.70, 26.00, 22.4. m.p.: 133–135° C. R$_f$: 0.4 5% methanol/ethyl acetate; Mass spectrum: M$^+$=260 (HRMS).

Example 46

Synthesis of N-(2,6-Dichloropurin-9-yl)-7-pentyloxycarbonyl-D-arginine—Compound #46

$^1$H NMR (δ, DMSO in ppm): 9.33 (s, 1H, COOH), 8.75 (s, 1H, purine), 7.3–7.8 (bs, 4H, guanidine), 6.28 (d, 1H, NH), 4.23 (t, 2H, CH$_2$), 3.86 (t, 2H, CH$_2$), 3.61 (m, 1H, C$^α$H), 3.015 (m, 2H, CH$_2$), 1.2–1.9 (m, 10H, 5xCH$_2$). m.p.: Softens at 136° C. melts at 147° C. R$_f$: 0.46 methanol; Mass spectrum: M$^+$=476

Example 47
Synthesis of N-(2,6-Dichloropurin-9-yl)-7-pentyloxycarbonyl-L-arginine—Compound #47

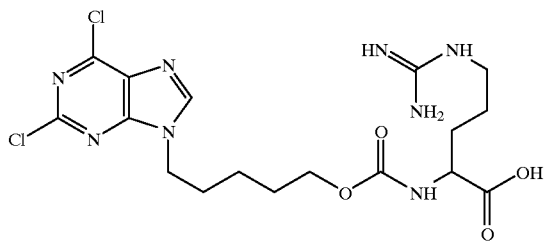

$^1$H NMR (δ, CD$_3$OD in ppm): 8.38 (s, 1H, purine), 4.12 (t, 2H, CH$_2$), 3.80 (m, 3H, CH$_2$ and C$^α$H), 2.97 (m, 2H, CH$_2$), 1.2–1.8 (m, 10H, 5xCH$_2$). m.p.: Softens at 137° C., melts at 147° C. R$_f$: 0.45 (methanol); Mass spectrum: M$^+$=476

Example 48
N-(2-Amino, 6—N,N-Dimethylaminopurin-9-yl)-5-pentanol—Compound #48

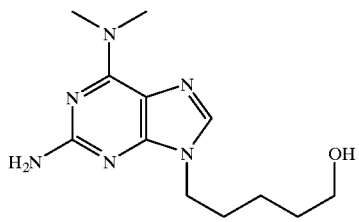

$^1$HNMR (δ in CDCl3 ppm): 7.46 (s, 1H, purine), 4.70 (bs, 2H, NH$_2$), 4.04 (t, 2H, CH$_2$), 3.65 (t, 2H, CH$_2$), 3.46 (bs, 6H, 2 x CH$_3$), 1.95 (m, 2H, CH$_2$), 1.65 (m, 2H, CH$_2$), 1.42 (m, 2H, CH$_2$) $^{13}$CNMR (δ in CD$_3$OD ppm): 158.27, 154.08, 150.74, 136.12, 112.96, 60.28, 41.97, 36.50, 30.71, 28.38, 21.64. m.p.: 139–141° C. R$_f$: 0.55 (15% Methanol/Ethyl acetate); Mass spectrum: M$^+$=265.

Example 49
Synthesis of N-(6-dimethylamino-8-methylthiopurin-9-yl) 5-pentanol Compound #49

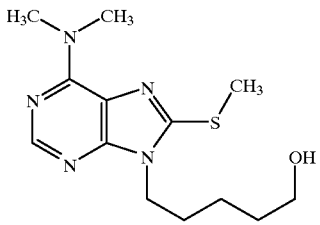

$^1$H NMR (CDCl$_3$, 400 MHz, δ in ppm); 8.24 (1H, s, purine); 4.08 (2H, t, N—CH$_2$); 3.61(2H, t, O—CH$_2$); 3.49 (6H, br s, N—(CH$_3$)$_2$); 2.70 (3H, s, S—CH$_3$); 1.81 (2H, p, CH$_2$); 1.67 (1H, br s, OH); 1.59 (2H, p, CH$_2$); 1.39 (2H, p, CH$_2$). $^{13}$C NMR (CDCl$_3$, 400 MHz, δ in ppm); 152.30, 151.69, 150.29, 146.47, 119.39, 61.58, 41.77, 37.45, 31.28, 28.08, 21.81, 13.43.

Example 50
Synthesis of N-(6-dimethylamino-8-methylthiopurin-9-yl) 7-pentoxycarbonyl-D-arginine—Compound #50

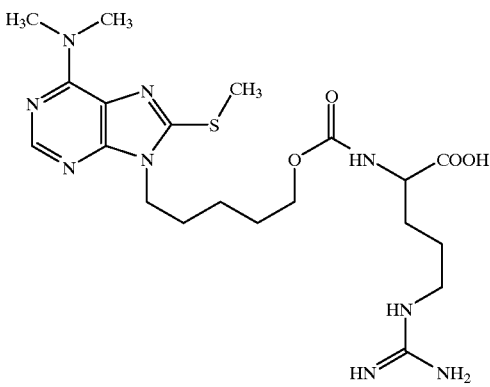

$^1$H NMR (DMSO-d$_6$, 400 MHz, δ in ppm); 8.13 (1H, s, purine); 8.0–7–2 (4H, br, guanidine); 6.32 (1H, d, NH); 4.01 (2H, t, N—CH$_2$); 3.86 (2H, t, O—CH$_2$); 3.65 (1H, m, C$^α$H); 3.41 (6H, br s, N—(CH$_3$)$_2$); 3.02 (2H, br, C$^δ$H$_2$); 1.8–1.2 (10H, m, C$^β$H$_2$, C$^γ$H$_2$, —(CH$_2$)—). $^{13}$C NMR (CDCl$_3$, 400 MHz, δ in ppm); 175.09, 156.83, 155.01, 152.01, 151.87, 150.46, 146.70, 118.84, 62.82, 54.61, 41.66, 39.91, 37.32, 29.26, 27.80, 27.69, 24.62, 22.05, 13.38.

Example 51
Synthesis of N-(6-methoxypurin-9-yl) 5-pentanol—Compound #51

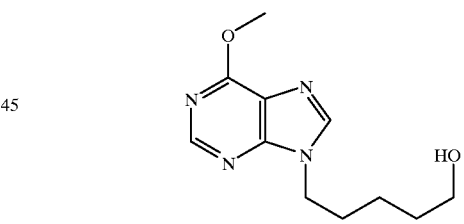

$^1$H NMR (CDCl$_3$, 400 MHz, δ in ppm); 8.43 (1H, s, purine); 7.86 (1H, s, purine); 4.18 (2H, t, N—CH$_2$); 4.09 (3H, s, O—CH$_3$); 3.55 (2H, t, O—CH$_2$); 3.09 (1H, br s, OH); 1.86 (2H, m, CH$_2$); 1.53 (2H, m, CH$_2$); 1.37 (2H, m, CH$_2$). $^{13}$C NMR (CDCl$_3$, 400 MHz, δ in ppm); 160.0, 150.9, 141.2, 120.4, 60.9, 53.2, 43.1, 30.9, 28.8, 22.0. m.p.=150° C. R$_f$=0.30 (15% methanol-ethyl acetate)

Example 52

Synthesis of N-(6-methoxypurin-9-yl) 7-pentoxycarbonyl-D-arginine—Compound #52

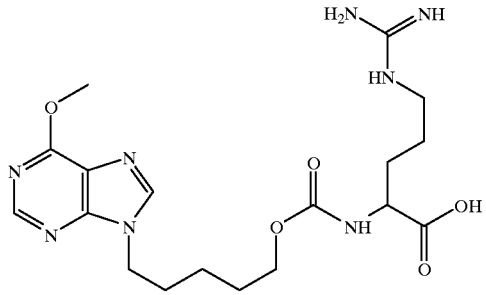

¹H NMR (DMSO-d₆, 300 MHz, δ in ppm); 8.51 (1H, s, purine); 8.39 (1H, s, purine); 8.0–7.3 (4H, br, guanidine); 6.29 (1H, d, N$\underline{H}$); 4.22 (2H, t, N—C$\underline{H}_2$); 4.08 (3H, s, O—C$\underline{H}_3$); 3.86 (2H, t, O—C$\underline{H}_2$); 3.62 (1H, m, C$^\alpha\underline{H}$); 3.02 (2H, br, C$^\delta\underline{H}_2$); 1.8–1.2 (10H, m, C$^\beta\underline{H}_2$, C$^\gamma\underline{H}_2$, (C$\underline{H}_2$)₃). ¹³C NMR (CDCl₃, 400 MHz, δ in ppm); 205.9, 175.8, 160.6, 157.7, 155.8, 152.4, 151.8, 120.9, 63.7, 55.4, 54.2, 43.6, 39.1, 30.1, 29.3, 28.5, 25.5, 22.9. m.p. (softens 132° C.)=148° C. R$_f$=0.35 (40% methanol-ethyl acetate)

Example 53

Synthesis of N-(2-chloro-6-methoxypurin-9-yl)-7-pentyloxycarbonyl-D-arginine—Compound #53

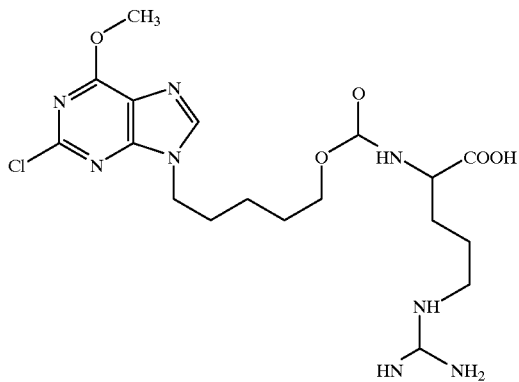

¹HNMR (δ, DMSO in ppm) 9.41 (bs, 1H, COOH), 8.42 (s, 1H, purine), 7.3–7.8 (bd, 4H, guanidine), 6.28 (d, 1H, NH), 4.08 (s, 3H, CH₃), 3.87 (t, 2H, CH₂), 4.18 (t, 2H, CH₂), 4.08 (s, 3H, CH₃), 3.87 (t, 2H, CH₂), 4.08 (s, 3H, CH₃), 3.87 (t, 2H, CH₂), 3.61 (m, 1H, C$^\alpha$H), 3.04 (m, 2H, CH₂), 1.22–1.87 (m, 10H, 5 X CH₂). m.p.: Softens at 128° C., melts at 141° C. R$_f$: 0.45 (Methanol); Mass spectrum: M⁺=471.

Example 54

Synthesis of N-(6-dimethylaminopurin-9-yl) 7-pentoxycarbonyl-D-ornithine—Compound #54

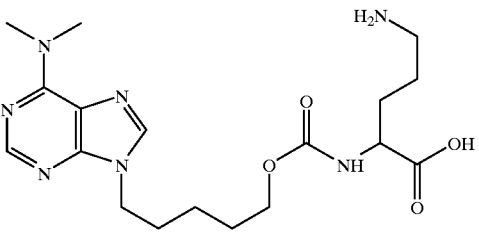

¹H NMR (DMSO-d₆, 400 MHz, δ in ppm); 8.20 (1H, s, purine); 8.12 (1H, s, purine); 6.21 (1H, d, N$\underline{H}$); 4.10 (2H, t, N—C$\underline{H}_2$); 3.87 (2H, t, O—C$\underline{H}_2$); 3.59 (1H, m, C$^\alpha\underline{H}$); 3.4 (br, N—(C$\underline{H}_3$)₂, N$\underline{H}_2$), 2.70 (2H, m, C$^\delta\underline{H}_2$); 1.9–1.2 (10H, m, (C$\underline{H}_2$)₃, C$^\beta\underline{H}_2$, C$^\gamma\underline{H}_2$). ¹³C NMR (CD₃OD, 400 MHz, δ in ppm); 176.3, 156.2, 153.8, 150.7, 148.8, 138.9, 118.5, 63.5, 54.2, 42.5, 38.0, 37.0, 28.6, 28.3, 27.2, 22.4, 21.7. m.p. (softens 185° C.)=189–190° C. R$_f$=0.20 (methanol)

Example 55

Synthesis of N-(6-dimethylaminopurin-9-yl) 7-pentoxycarbonyl-L-ornithine—Compound #55

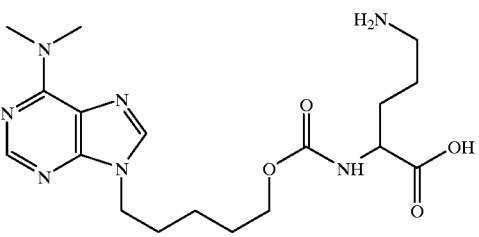

Spectral properties were identical with compound #54.

Example 56

Synthesis of N-(6-dimethylaminopurin-9-yl) 7-pentoxycarbonyl-L-valine—Compound 56

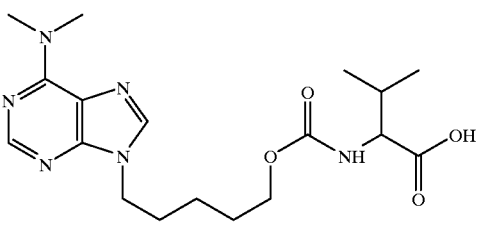

¹H NMR (DMSO-d₆, 400 MHz, δ in ppm); 8.19 (1H, s, purine); 8.16 (1H, s, purine); 6.30 (1H, d, N$\underline{H}$); 4.13 (2H, t, N—C$\underline{H}_2$); 3.87 (2H, m, O—C$\underline{H}$2); 3.64 (1H, m, C$^\alpha\underline{H}$); 3.4 (br s, N—(C$\underline{H}_3$)₂); 1.80 (2H, p, C$\underline{H}_2$,); 1.25 (2H, p, C$\underline{H}_2$,); 0.79 (3H, d, C$^\gamma\underline{H}_3$); 0.75 (3H, d, C$^\gamma\underline{H}_3$). ¹³C NMR (CD₃OD, 400 MHz, δ in ppm); 174.6, 156.7, 153.7, 150.5, 148.9, 138.6, 118.6, 63.4, 59.2, 42.3, 36.729.6, 28.3, 27.3, 21.7, 17.5, 15.9. m.p. (softens 140° C.)=172–176° C. R$_f$=0.20 (30% methanol-ethyl acetate)

Example 57

Synthesis of N-(6-dimethylamino-9-yl) 7-pentoxycarbonyl-D-valine—Compound #57

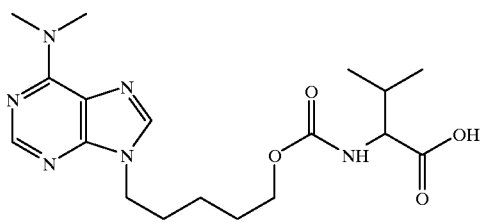

Spectral properties were identical with compound #56.

Example 58

Synthesis of N(N,N-dimethylaminopurin-9-yl)-7-pentyloxycarbonylethylamine hydrochloride—Compound #58

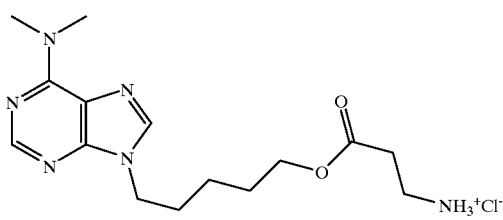

$^1$HNMR (δ in DMSO ppm): 8.40 (s, 1H, purine), 8.43 (s, 1H, purine), 8.04 (bs, 3H, NH$_3$), 4.24 (t, 2H, CH$_2$), 4.02 (t, 2H, CH$_2$), 2.99 (m, 2H, CH$_2$), 2.67 (t, 2H, CH$_2$), 1.83 (m, 2H, CH$_2$), 1.62 (m, 2H, CH$_2$), 1.28 (m, 2H, CH$_2$). R$_f$: 0.3 10% Methanol/Ethylacetate; Mass spectrum: M$^+$=321

Example 59

Synthesis N-(6-Mercaptopurin-9-yl)-pentanol—Compound #59

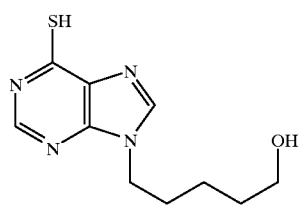

$^1$HNMR (δ DHSO in ppm): 8.30 (s, 1H, C$_8$-purine), 8.18 (s, 1H, C$_2$-purine), 4.34 (t, 1H, OH), 4.15 (t, 2H, CH$_2$—O), 3.34 (t, 2H, CH$_2$—N), 1.82 (m, 2H, CH$_2$), 1.42 (m, 2H, CH$_2$), 1.24 (m, 2H, CH$_2$). R$_f$: 0.57 30% Methanol/Ethylacetate; Mass spectrum: M$^+$=239

Example 60

Synthesis of N-(6,-N-Methylthiopurin-9-yl)-pentanol—Compound #60

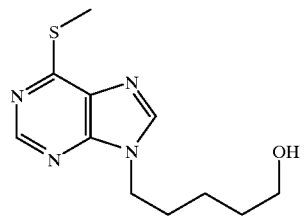

$^1$HNMR (δ CDCl$_3$ in ppm): 8.74 (s, 1H, C$_8$-purine), 7.95 (s, 1H, C$_2$-purine), 4.27 (t, 2H, CH$_2$—N), 3.65 (t, 2H, CH$_2$—O), 2.74 (s, 3H, SCH$_3$), 1.94 (m, 2H, CH$_2$), 1.60 (m, 2H, CH$_2$), 1.43 (m, 2H, CH$_2$).

$^{13}$CNMR (δ CD$_3$OD in ppm): 163.23, 153.42, 149.96, 145.89, 132.48, 63.08, 45.60, 33.62, 31.24, 24.54, 12.29. m.p.: 95–97° C. R$_f$: 0.22 (Ethylacetate); Mass spectrum: M$^+$=253

Example 61

Synthesis of N-(6-chloropurin-9-yl) 4-butanol—Compound #61

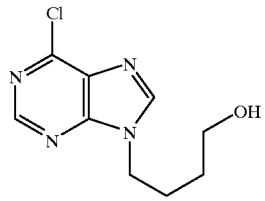

$^1$H NMR (CDCl$_3$, 400 Mhz, δ in ppm): 8.66 (1H, s, purine), 8.16 (1H, s, purine), 4.33 (2H, t, N—CH$_2$), 3.67 (2H, t, O—CH$_2$), 3.04 (1H, br s, OH), 2.01 (2H, p, CH$_2$), 1.55 (2H, p, CH$_2$) m.p.=97° C.

Example 62

Synthesis of N-(6-dimethylaminopurin-9-yl) 4-butanol—Compound #62

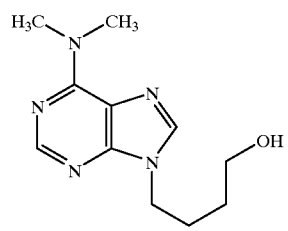

$^1$H NMR (CDCl$_3$, 400 Mhz, δ in ppm): 8.24 (1H, s, purine), 7.68 (1H, s, purine), 4.33 (2H, t, N—CH$_2$), 3.89 (1H, br s OH), 3.64 (2H, t, O—CH$_2$), 3.46 (6H, br, N—(CH$_3$)$_2$), 1.92 (2H, p, CH$_2$), 1.53 (2H, p, CH$_2$) m.p.=78° C.

Example 63
Synthesis of N-(6-dimethylaminopurin-9-yl)-6-butoxycarbonyl-D-arginine—Compound #63

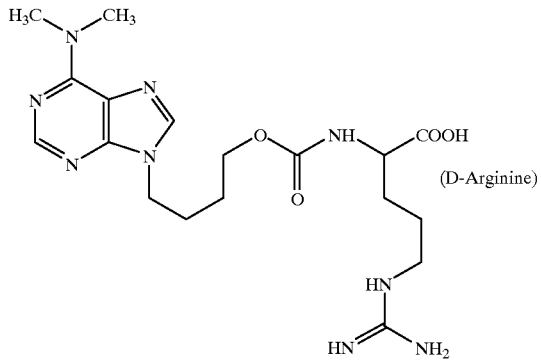
(D-Arginine)

$^1$H NMR (DMSO-$d_6$, 400 Mhz, δ in ppm); 8.20 (1H, s, purine), 8.16 (1H, s, purine), 8.1–7.3 (4H, br, guanidine), 6.40 (1H, d, NH), 4.16 (2H, t, N—CH$_2$), 3.91 (2H, t, O—CH$_2$), 3.65 (1H, M, C$^\delta$H), 3.4 (6H, br, N—(CH$_3$)$_2$), 3.02 (2H, m, C$^\delta$H), 1.9–1.3 (8H, m, C$^\beta$H, C$^\gamma$H, —(CH$_2$)$_2$—). m.p. (softens 85° C.)=140–142° C.

Example 64
Synthesis of N-(6-dimethylaminopurin-9-yl)-6-butoxycarbonyl-L-arginine—Compound #64

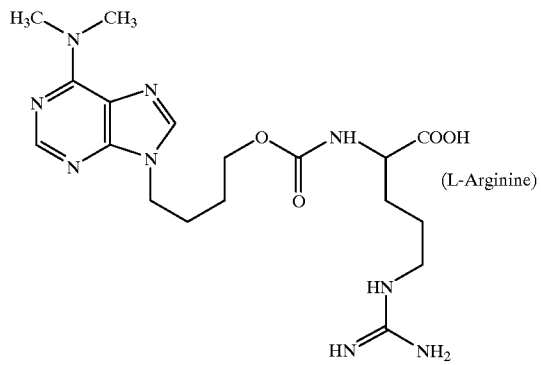
(L-Arginine)

Spectral properties were identical with compound #63. m.p. (softens 85° C.)=139–142° C.

Example 65
Synthesis of N-(6-chloropurin-9-yl)-6-hexanol—Compound #65

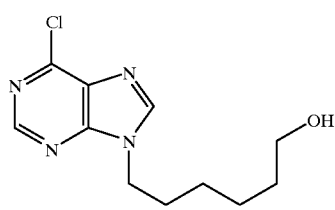

$^1$H NMR (δ, CDCl$_3$ in ppm): 8.69 (s, 1H, purine), 8.11 (s, 1H, purine), 4.27 (t, 2H, CH$_2$), 3.58 (t, 2H, CH$_2$), 2.21 (bs, 1H, OH), 1.91 (m, 2H, CH$_2$), 1.43 (m, 2H, CH$_2$), 1.35 (m, 4H, 2xCH$_2$) $^{13}$C NMR (δ, CDCl$_3$ in ppm): 152.45, 151.60, 145.69, 132.16, 112.00, 63.00, 44.96, 32.86, 30.39, 26.87, 25.67. m.p.=84–86° C. R$_f$=0.5 10% (methanol/ethyl acetate); Mass spectrum: M$^+$=255

Example 66
Synthesis of N-(6—N,N-dimethylaminopurin-9-yl)-6-hexanol—Compound #66

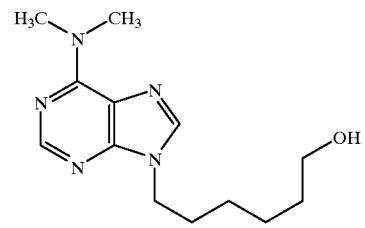

$^1$H NMR (δ, CDCl$_3$ in ppm): 8.35 (s, 1H, purine), 7.71 (s, 1H, purine), 4.17 (t, 2H, CH$_2$), 3.61 (t, 2H, CH$_2$), 3.53 (bs, 6H, 2xCH$_3$), 1.89 (m, 2H, CH$_2$), 1.71 (bs, 1H, OH), 1.55 (m, 2H, CH$_2$), 1.45 (m, 4H, 2xCH$_2$). $^{13}$C NMR (δ, CDCl$_3$ in ppm): 154.44, 152.90, 150.95, 138.72, 120.53, 63.04, 44.08, 39.28, 32.95, 30.61, 26.80, 25.64. m.p. 75–77° C. R$_f$=0.48 10% methanol/ethyl acetate; Mass spectrum: M$^+$=264

Example 67
Synthesis of N-(6—N,N-dimethylaminopurin-9-yl)-8-hexyloxycarbonyl-D-arginine—Compound #67

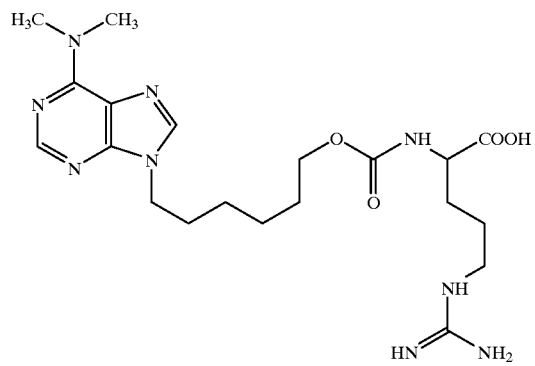

$^1$H NMR (δ, CD$_3$OD in ppm): 7.98 (s, 1H, purine), 7.81 (s, 1H, purine), 3.98 (t, 2H, CH$_2$), 3.78 (m, 3H, CH$_2$ and C$^\alpha$H), 3.27 (bs, 6H, 2xCH$_3$), 2.96 (t, 2H, CH$_2$), 1.1–1.78 (m, 12H, 6xCH$_2$).

Example 68
Synthesis of N(6—N,N-dimethylaminopurine-9-yl)-8-hexyloxycarbonyl-L-arginine—Compound #68

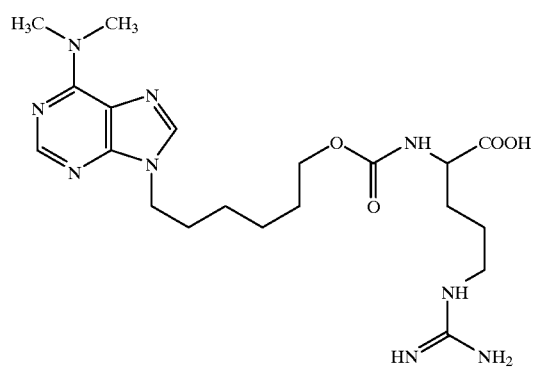

$^1$H NMR (δ, CD$_3$OD in ppm): 8.00 (s, 1H, purine), 7.82 (s, 1H, purine), 4.00 (t, 2H, CH$_2$), 3.80 (m, 3H, CH$_2$ and C$^α$H), 3.29 (bs, 6H, 2xCH$_3$), 2.97 (t, 2H, CH$_2$), 1.13–1.72 (m, 12H, 6xCH$_2$).

Example 69
Synthesis of cis-(N-6-hydroxypurin-9-yl)-4-ethyl-cyclohexyl-methanol—Compound #69

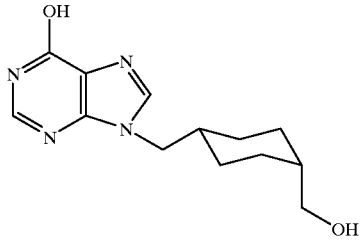

$^1$H NMR (CD$_3$OD, 400 Mhz, δ in ppm): 8.08 (1H, s, purine), 8.07 (1H, s, purine), 4.21 (2H, d, N—CH$_2$), 3.49 (2H, d, O—CH$_2$), 2.16 (1H, m, CH), 1.7–1.2 (9H, m, CH$_2$-cyclohexane, CH). m.p. >200° C. R$_f$=0.3 (20% methanol-ethyl acetate)

Example 70
Synthesis of cis-(N-6-hydroxypurin-9-yl)-4-methyl-cyclohexyl-methyloxycarbonyl-D-arginine—Compound #70

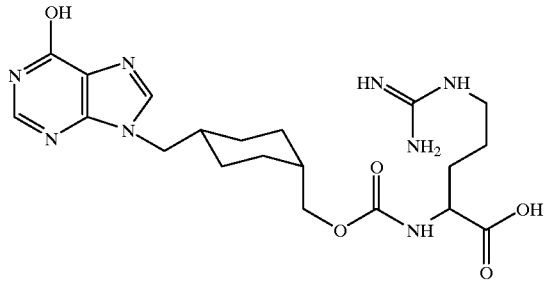

$^1$H NMR (CD$_3$OD, 400 Mhz, δ in ppm): 8.10 (1H, s, purine), 8.09 (1H, s, purine), 4.24 (2H, d, N—CH$_2$), 3.65 (1H, m, C$^α$H), 3.52 (2H, d, O—CH$_2$), 2.95 (2H, m, C$^δ$H$_2$), 2.2–1.2 (14H, m, 2xCH-cyclohexane, 4xCH$_2$-cyclohexane, C$^β$H$_2$, C$^γ$HH$_2$).

Example 71
Synthesis of trans-(N-6-hydroxypurin-9-yl)-4-methyl-cyclohexyl-methyloxycarbonyl-D-arginine—Compound #71

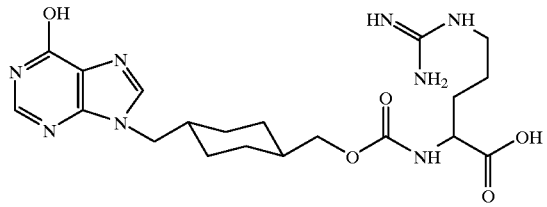

$^1$H NMR (CD$_3$OD, 300 Mhz, δ in ppm): 8.09 (2H, s, purine), 4.12 (2H, d, N—CH$_2$), 3.68 (1H, m, C$^α$H), 3.36 (2H, d, O—CH$_2$), 3.01 (2H, m, C$^δ$H$_2$), 2.0–0.9 (14H, m, 2xCH-cyclohexane, 4xCH$_2$-cyclohexane, C$^β$H$_2$, C$^γ$H$_2$). m.p. >200° C. R$_f$=0.2 (methanol)

Example 72
Synthesis of N-(6—N,N dimethylaminopurin-9-yl)-5-pentylamine hydrochloride salt—Compound #72

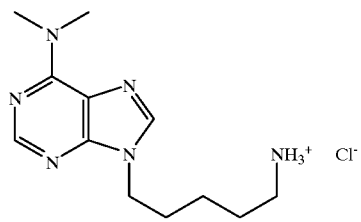

$^1$H NMR (δ, DMSO in ppm): 8.20 (s, 1H, purine), 8.16 (s, 1H, purine), 7.84 (bs, 3H, NH$_3$), 4.14 (t, 2H, CH$_2$), 3.44 (bs, 6H, 2xCH$_3$), 2.73 (t, 2H, CH$_2$), 1.81 (m, 2H, CH$_2$), 1.56 (m, 2H, CH$_2$), 1.25 (m, 2H, CH$_2$).

Example 73
Synthesis of N-(6-methylaziridinepurin-9-yl)-7-pentyloxycarbonyl-L-arginine—Compound #73

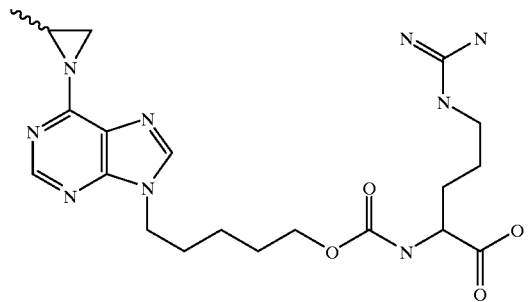

Spectral data of compound #73 was comparable to that reported for compound #39.

Example 74
(2S,4S)-2-(N,N-Dimethylaminopurin-9-yl)-4-hydroxymethyl-1,3-dioxolane—Compound #74

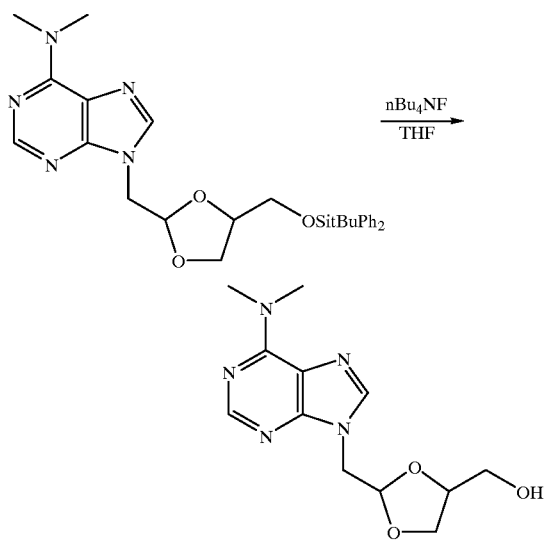

$^1$H NMR (CDCl$_3$): δ 8.32 (s, 1H, H-2-purine), 7.75 (s, 1H, H-8-purine), 5.33 (dd, 1H, J=2.0, 6.6, H-2-dioxolane), 5.33 (bs, 1H, OH), 4.45 (dd, 1H, J=6.6, 14.3, CH$_2$-purine), 4.20

(dd, 1H, J=2.0, 14.3, CH₂-purine), 4.20 (m, 1H, H-4-dioxolane), 4.05 (d, 2H, J=7.2, H-5), 3.78 (d, 1H, J=13.0, CH₂—OH), 3.53 (bs, 6H, (CH₃)₂N), 3.40 (d, 1H, J=13.0, CH₂—OH).

Example 75

(1S,3R) and (IR,3S)-1-(N-6-Dimethylaminopurin-9-yl)methyl-3-cyclopentane methanol—Compound #75

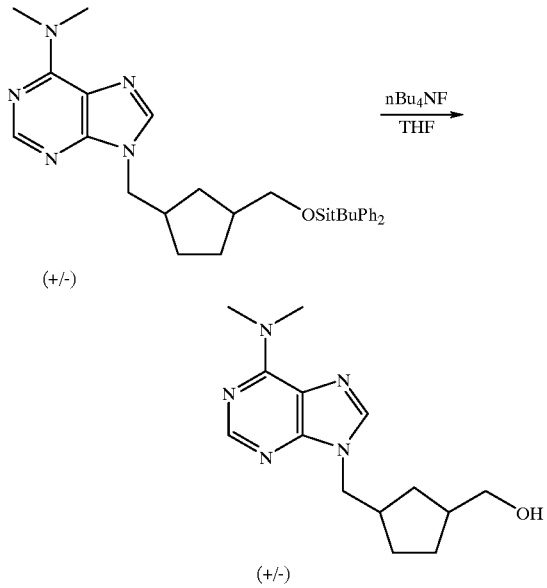

¹H NMR (CDCl₃, 300 MHz.): δ 8.32 (s, 1H, H-2-purine), 7.71 (s, 1H, H-8-purine), 4.18 (dd, 1H, J=8.6, 13.7), 4.06 (dd, 1H, J=6.7, 13.7), 3.61–3.53 (m, 8H), 3.00 (bs, 1H, OH), 2.48 (m, 1H), 2.17 (m, 1H), 1.88–1.68 (m, 3H), 1.53 (m, 1H), 1.43 (m, 1H), 1.08 (m, 1H).

Example 76

(1S,3R) and (1R,3S)-1-(N-6-Dimethylaminopurin-9-yl)methyl-3-(methyloxycarbonyl-D-arginine)cyclopentane—Compound #76

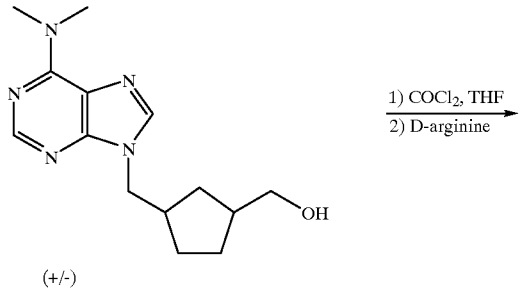

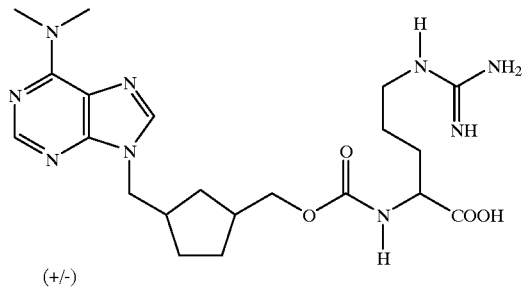

Example 77

N,N-(6-Dimethylaminopurin-9-yl)-7-ethylaminoethanol—Compound #77

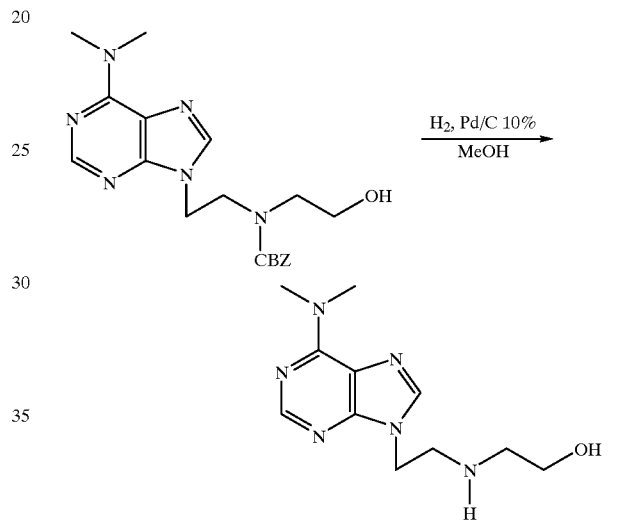

¹H NMR (CDCl₃, 400 MHz): δ 8.34 (s, 1H, H-2-purine), 7.79 (s, 1H, H-8-purine), 4.29 (t, 2H, J=5.8, —CH₂—), 3.62 (m, 2H, —CH₂—), 3.54 (bs, 6H, (CH₃)₂N), 3.11 (t, 2H, J=5.8, —CH₂—), 2.81 (t, 2H, J=5.2, —CH₂—), 2.05 (bs, 2H, NH and OH).

Example 78

N,N-(6-Dimethylaminopurin-9-yl)-7-ethylaminoethoxycarbonyl-D-arginine

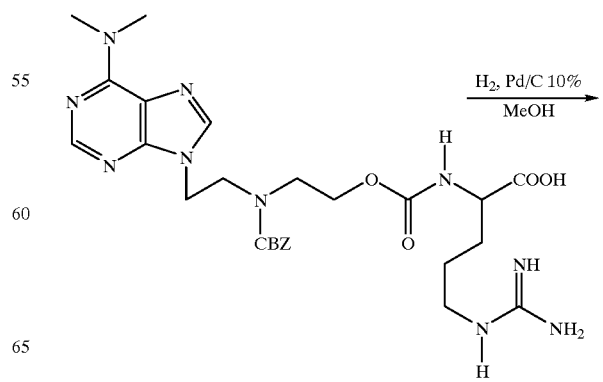

-continued

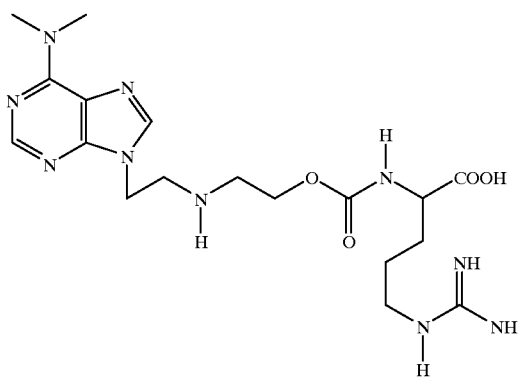

¹H NMR (CDCl₃, 300 MHz) δ 9.36 (m, 1H), 8.19 (s, 1H, H-2-purine), 8.11 (s, 1H, H-8-purine), 6.38 (d, 1H, J=7.0, NH carbamate), 4.17 (t, 2H, J=6.1, —CH₂—), 3.91–3.87 (m, 2H, —CH₂—), 3.65 (m, 1H, C$\underline{H}$—COOH), 3.43 (bs, 6H, (CH₃)₂N), 3.03–3.01 (m, 2H, C$\underline{H_2}$—NHC(NH)NH₂), 2.90 (t, 2H, J=6.1, —CH₂—), 2.68 (t, 2H, J=5.6, —CH₂—), 1.64–1.44 (m, 4H, C$\underline{H_2}$—C$\underline{H_2}$—CH₂NHC(NH)NH₂).

Example 79

N,N-(6-Dimethylaminopurin-9-yl)-7-ethylaminoethoxycarbonyl-L-arginine

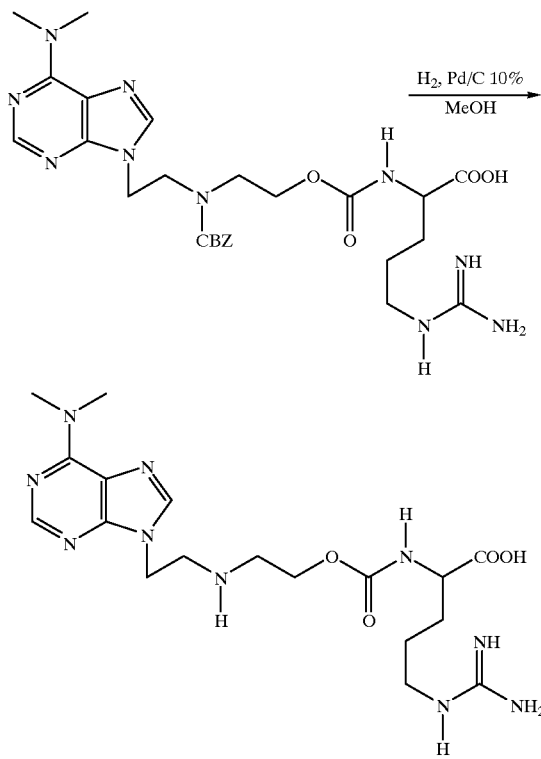

Spectral properties were identical with compound #78.

Example 80

5-(N-6-Dimethylaminopurin-9-yl)-3-pentyn-1-ol— Compound #80

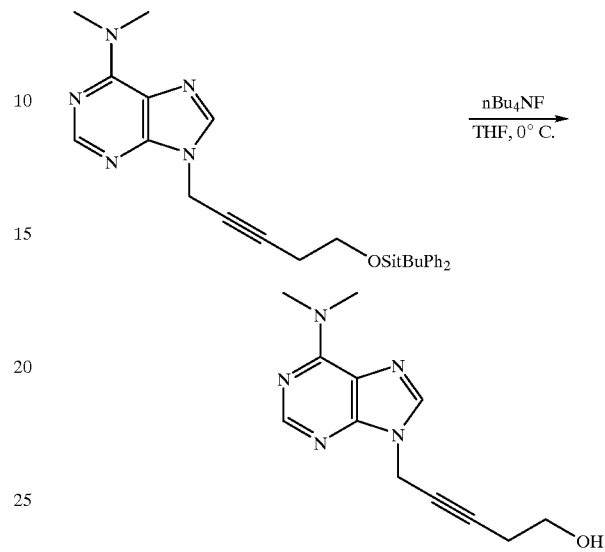

¹H NMR (CDCl₃): δ 8.34 (s, 1H, H-2 purine), 7.89 (s, 1H, H-8 purine), 4.91 (m, 2H, C$\underline{H_2}$—N), 3.74 (t, 2H, J=6.2, C$\underline{H_2}$—OH), 3.52 (bs, 6H, (C$\underline{H_3}$)₂N), 2.87 (bs, 1H, OH), 2.50 (m, 2H, C$\underline{H_2}$—CH₂$_{OH}$).

Example 81

5-(N-6-Dimethylaminopurin-9-yl)-3-pentynyl-1-oxycarbonyl-L-arginine—Compound #81

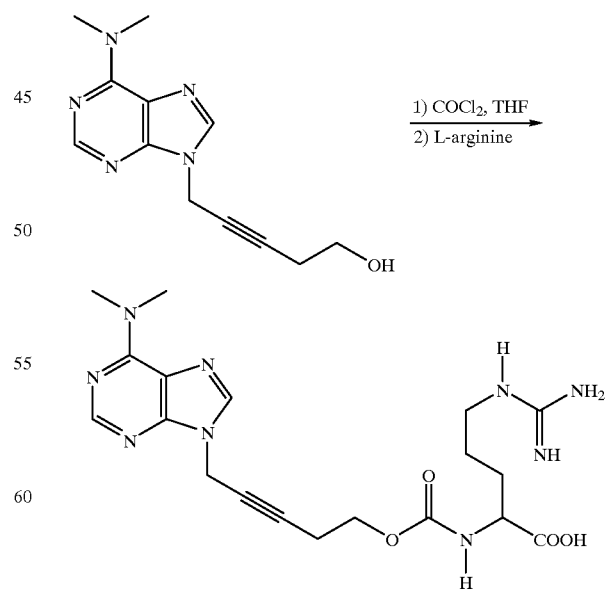

Spectral properties were identical with compound #40.

Example 82

N,N-(6-Dimethylaminopurin-9-yl)-7-thioethoxy-ethanol—Compound #82

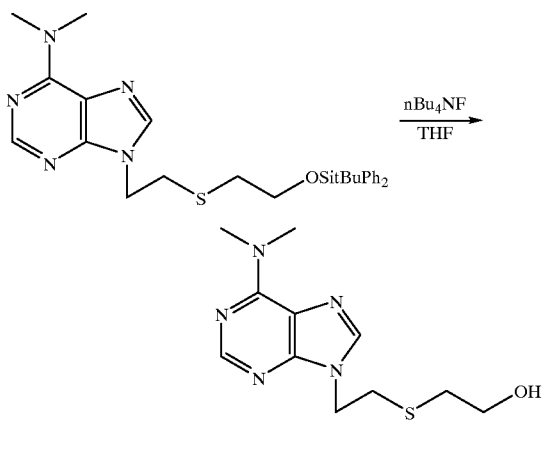

¹H NMR (CDCl₃): δ 8.30 (s, 1H, H-2-purine), 7.75 (s, 1H, H-8-purine), 4.41 (t, 2H, J=6.5, C$\underline{H}_2$ linker), 4.11 (bs, 1H, OH), 3.73 (t, 2H, J=6.5, C$\underline{H}_2$ linker), 3.51 (bs, 6H, (C$\underline{H}_3$)₂N), 2.99 (t, 2H, J=6.5, C$\underline{H}$2 linker), 2.68 (t, 2H, J=6.5, C$\underline{H}$2 linker).

Example 83

N,N-(6-Dimethylaminopurin-9-yl)-7-thioethoxy-ethoxycarbonyl-L-arginine—Compound #83

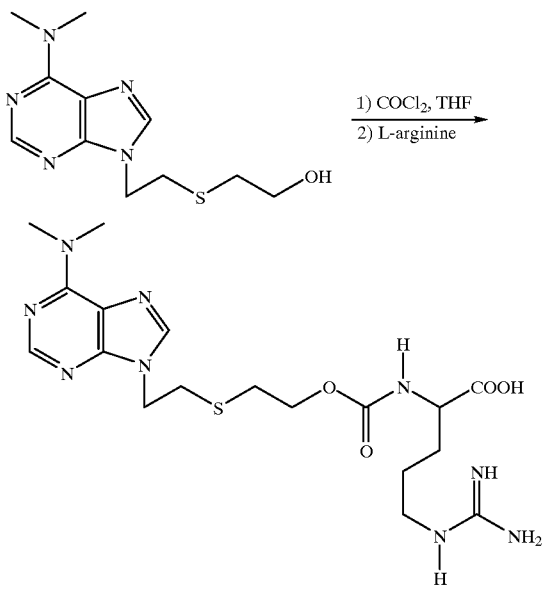

Spectral properties were identical with compound #40.

Example 84

(2S,4S) and (2R,4R)-2-(N,N-Dimethylaminopurin-9-yl)-4-(methoxycarbonyl-D-arginine)-1,3-oxathiolane—Compound #84

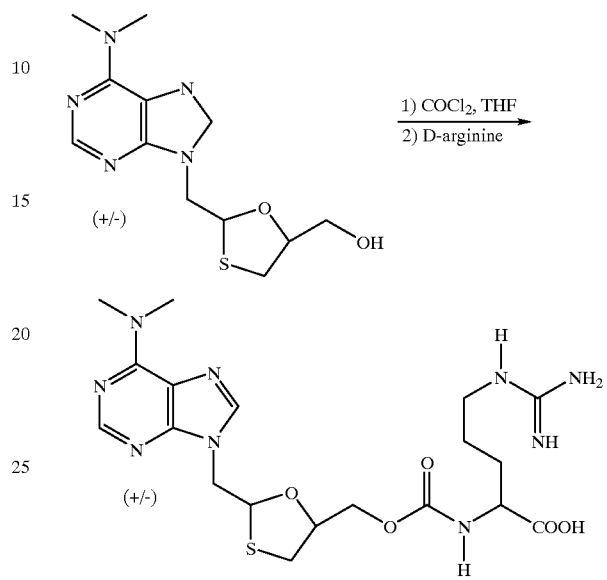

¹H NMR (CDCl₃, 300 MHz): δ 8.49 (s, 1H, H-2-purine), 8.47 (s, 1H, H-8-purine), 6.60 (bs, 1H, NH carbamate), 6.22 (m, 1H, H-2-oxathiolane), 4.26–4.03 (m, 3H), 3.63–3.00 (m, 11H), 2.78–2.69 (m, 2H, H-5-oxathiolane), 1.53–1.40 (m, 4H, C$\underline{H}_2$—C$\underline{H}_2$—CH₂NH—C(NH)NH₂).

Example 85

N,N-(6-Dimethylaminopurin-9-yl)-7-ethoxy-ethoxyethanol—Compound #85

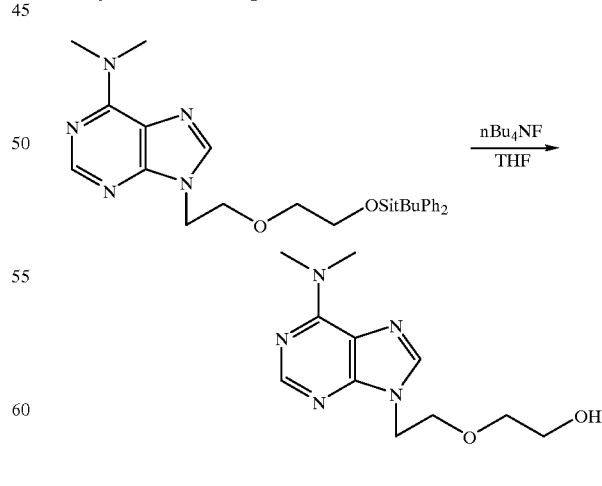

¹H NMR (CDCl₃): δ 8.29 (s, 1H, H-2-purine), 7.80 (s, 1H, H-8-purine), 4.33 (t, 2H, C$\underline{H}_2$), 3.82 (t, 2H, C$\underline{H}_2$), 3.68 (t, 2H, C$\underline{H}_2$), 3.55 (t, 2H, C$\underline{H}_2$), 3.50 (m, 6H, N(C$\underline{H}_3$)₂).

Example 86

N,N-(6-Dimethylaminopurin-9-yl)-7-ethoxy-ethoxycarbonyl-D-arginine—Compound #86

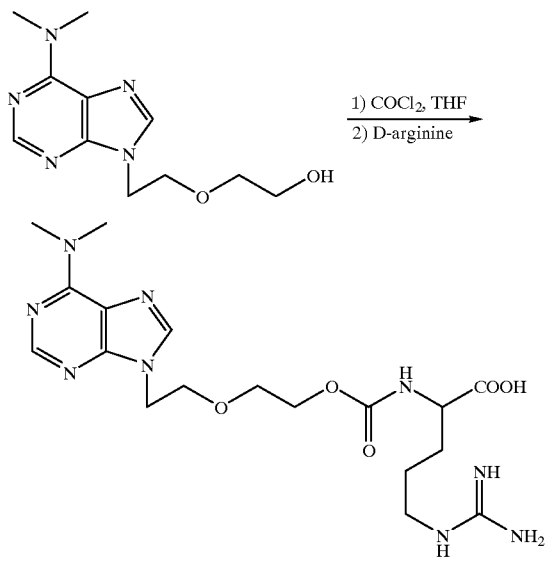

$^1$H NMR (DMSO-$d_6$): δ 8.25 (s, 1H, H-2-purine), 8.14 (s, 1H, H-8-purine), 6.5 (bd, 1H, NH carbamate), 4.37 (t, 2H, CH$_2$ linker), 4.03 (m, 2H, CH$_2$ linker), 3.81 (m, 2H, CH$_2$ linker), 3.72 (m, 1H, CH—COOH), 3.60 (m, 2H, CH$_2$ linker), 3.55–3.89 (m, 6H, N(CH$_3$)$_2$), 3.05 (m, 2H, CH$_2$—NH—C(NH)NH$_2$), 1.78–1.39 (m, 4H, CH$_2$—CH$_2$—CH$_2$NH—C(NH)NH$_2$).

Example 87

N,N-(6-Dimethylaminopurin-9-yl)-7-ethoxy-ethoxycarbonyl-L-arginine—Compound #87

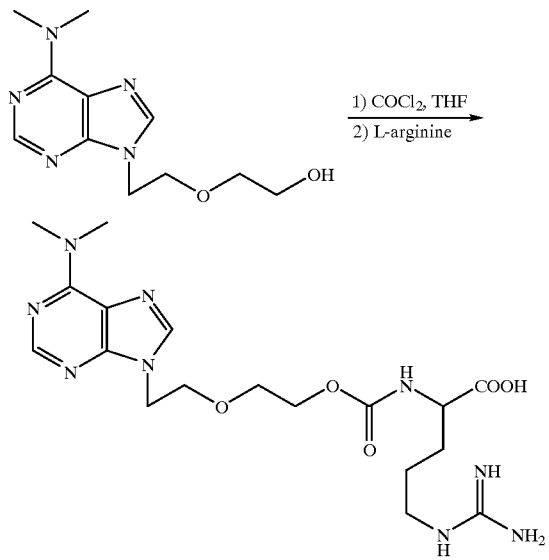

Spectral properties were identical with compound #86.

Example 88

N-(6-Dimethylamino-8-bromopurin-9-yl)5-pentanol—Compound #88

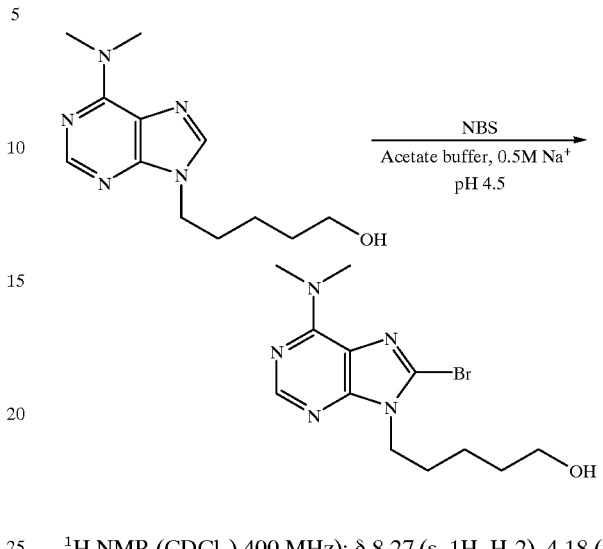

$^1$H NMR (CDCl$_3$) 400 MHz): δ 8.27 (s, 1H, H-2), 4.18 (t, 2H, J=7.2, CH$_2$), 3.64 (t, 2H, J=6.3, CH$_2$), 3.48 (bs, 6H, N(CH$_3$)$_2$), 2.02 (bs, 1H, OH), 1.85 (quint, 2H, J=7.2, CH$_2$), 1.63 (quint, 2H, J=6.3, CH$_2$), 1.46 (m, 2H, CH$_2$).

BIOLOGICAL DATA

IN VITRO SCREENING:

Example 89

Mitogenic Proliferation on Spleen Cell Suspension

Mitogenic lectin (mitogen) is a protein which binds and cross-links specific cells surface carbohydrate determinants, and will polyclonally stimulate lymphoid cells. Lymphocyte activation by either antigens or mitogens results in intracellular changes and the subsequent development into a lymphoblast. Mitogenic stimulation of lymphocytes in vitro is believed to mimic the series of events which occur in vivo following their stimulation by specific antigens. PHA, ConA, and PWM, LPS mitogens can be used as a measurement of T cell and B cell activity, respectively.

Briefly, spleen mononuclear leukocytes from C57BL-6 mice were incubated in the presence or absence of mitogens with or without tested drugs. After 72 hours or 5 days, $^3$H thymidine incorporation was recorded as an indication of cell transformation and proliferation.

100 μl of a suspension of 2×10$^6$ cells/ml (2×10$^5$ cells/well) were incubated in presence of PHA or ConA or PWM or LPS at the following concentrations:

PHA=0.01% final concentration–0.001%
ConA=2 μg/ml–1 μg/ml
PWM=0.2x–0.02x
LPS=5 μg/ml–2 μg/ml Cells were incubated in presence or absence of drugs for 72 hours. 0.5 or 1 μCi of tritiated thymidine ($^3$H) was added per well the last 18 or 6 hours of incubation respectively. Cells were harvested and counted on a Beta counter.

TABLE 1

(Mitogenic Proliferation)

| Compound No. | T (ConA) (M) | B (LPS) (M) |
|---|---|---|
| ST-789 | 0 | $1.5 - 3 \times (10^{-8} - 10^{-5})$ |
| #1 | $2 - 4 \times (10^{-8} - 10^{-5})$ | $2 \times (10^{-6})$ |
| #2 | $2 - 4 \times (10^{-8} - 10^{-5})$ | 0 |
| #3 | $2 - 6 \times 10^{-12} - 10^{-6})$ | $2 - 2.5 \times (10^{-8} - 10^{-6})$ |
| #7 | $2 - 6 \times (10^{-12} - 10^{-8})$ | 0 |
| #9 | $2 - 3.5 \times (10^{-12} - 10^{-6})$ | |

Example 90
Cytotoxic T Lymphocytes (CTL) and Mixed Lymphocyte Reaction (MLR) Assays Mixed lymphocyte reaction is an in vitro counterpart of the allograft rejection. Briefly, T cell response was obtained when cells taken from two inbred strains from two outbred individuals of any species were mixed in vitro in culture. To have a unidirectional response, the proliferation of either cell type may be blocked with X-irradiation or mitomycin C treatment.

After 4 days incubation, $^3H$ thymidine uptake and cytotoxicity assay (CTL) were performed.

3 C57B1/6 mice and 3 DBA/2 mice wre killed and lymphocytes prepared using lympholyte M. The cell concentration was adjusted to $10 \times 10^6$ cell/ml for each lysis. DBA/2 cells were irradiated with 3000 Rads. 1 ml of the C57 cells+1 ml of the DBA/2 cells+1 ml of the drug at 3 different concentrations were incubated together for 5 days. Positive control was IL-2 at 15 ng/ml final. After 5 days, the CTL and MLR tests were carried out.

MLR

The cells were resuspended and 100 μl of cell suspension were deposited in each of the 96 wells in the plate, 50 μl of Thymidine at 20 μCi/ml was added for 6 hrs. The cells were then collected and counted using a beta counter.

CTL

P815 target cells were labelled with $Cr^{51}$. After labelling, the cells were resuspended to $5 \times 10^4$ cells/ml. Effector cells were adjusted to $2.5 \times 10^6$ cells/ml, and then diluted 1:2 and 1:4 to obtain the necessary effector to target ratios:

50:1 ($2.5 \times 10^6$ cells/ml: $5 \times 10^4$ cell/ml)

25:1 ($1.25 \times 10^6$ cells/ml: $5 \times 10^4$ cells/ml)

12.5:1 ($0.625 \times 10^6$ cells/ml: $5 \times 10^4$ cells/ml)

100 μl of target cells+100 μl Of T cells were incubated for 4 hrs and then 100 μl of supernatant was counted using a gamma counter.

TABLE 2

(CTL and MLR Assays)

| Compound No. | CTL (M) | MLR (M) |
|---|---|---|
| ST 689 | ++++ $(10^{-7} M)^P$ | $1.6 \times (10^{-5} M)^P$ |
| ST 789 | ++ $(10^{-7})$ | $2 - 3 \times (10^{-9} - 10^{-5})$ |
| #III | +++ $(10^{-7} M)$ | $1.5 - 2.5 \times (10^{-9} - 10^{-5} M)$ |
| #V | +++ $(10^{-7} M)$ | $1.5 - 2 \times (10^7 - 10^5 M)$ |
| #1 | ++++ $(10^{-9})$ | $1.5 - 4 \times (10^{-9} - 10^{-5})$ |
| #2 | 0 | $1.5 - 2 \times (10^{-7} - 10^{-5})$ |
| #3 | + $(10^{-5})$ | $1.5 \times (10^{-9} - 10^{-5})$ |
| #3a | +++ $(10^{-9} - 10^{-7} M)$ | $1.5 - 2.9 \times (10^{-9} - 10^{-5} M)$ |
| #5 | + $(10^{-7})$ | $1.5 - 2 \times (10^{-7} - 10^{-5})$ |
| #5a | ++ $(10^{-7} - 10^{-5} M)$ | $1.5 - 2 \times (10^{-9} - 10^{-6} M)$ |
| #6 | +++ $(10^{-9})$ | $1.5 - 3 \times (10^{-9} - 10^{-5})$ |

TABLE 2-continued (CTL and MLR Assays)

| Compound No. | CTL (M) | MLR (M) |
|---|---|---|
| #7 | +++ $(10^{-9})$ | $1.5 - 2 \times (10^{-9} - 10^{-6})$ |
| #7a | ++++ $(10^{-9} M)^P$ | $2 \times (10^{-9} - 10^{-5} M)^P$ |
| #8 | ++++ $(10^{-9})$ | $1.5 - 2 \times (10^{-9} - 10^{-5})$ |
| #11 | ++ $(10^{-7})$ | $2 - 2.5 \times (10^{-7} - 10^{-5})$ |
| #19 | ++ $(10^{-7} M)^P$ | $0^P$ |
| #20 | ++ $(10^{-5})$ | |
| #51 | ++ $(10^{-7} M)$ | $1.5 - 2 \times (10^{-9} - 10^{-6} M)$ |
| #59 | ++ $(10^{-9} M)$ | $2 - 2.4 \times (10^{-9} - 10^{-5} M)$ |
| #60 | + $(10^{-7} M)$ | $1.7 - 2 \times (10^{-9} - 10^{-5} M)$ |

For CTL Activity, the data expressed is as a % increase compared to IL-2. IL-2 is 100%. 0 represents less than 20%, + represents 20–40%, ++ represents 40–60%, and +++ represent 60–80%, and ++++ represents 80+. P = Preliminary result

IN VIVO/EX VIVO SCREENING

Example 91

Immunophenotyping

After in vivo drugs analysis, the drugs were evaluated on whole blood for drug stability and toxicity. Furthermore, in vivo/ex vivo analysis was performed on normal and cyclophosphamide immunosuppressed animals plus 5Fu-treated animals. Cell immunophenotyping was performed on mouse-treated blood and spleen. The following cell surface antigens were analyzed:

CD3 (all T cells), CD4 (T helper/inducer, binds class II-restricted T cells), CD8a (cytotoxic T cells, CTL adhesion), CD11a (T, B, NK, some stem cells, CTL adhesion anti LFA-1α), MAC-1 (monocyte/macrophage), NK (natural killer cells), Ly5 (B cells), CD45 (all leukocytes, protein tyrosine phosphates), and TCR (T cell receptor).

C57/BLJ6 mice (6–8 weeks old) were injected daily for 4 consecutive days, sacrificed at day 5 and immunophenotyping was performed on blood and spleen cells.

The cells were washed twice in PBS, resuspended in 1 ml of RPMI 2% FBS, and incubated for 45 min. on ice with monoclonal antibody. The cells were washed once, fixed with 1% paraformaldehyde, then analyzed using XL Coulter® counter. Results are presented in Table 3a and 3b.

TABLE 3a

Immunophenotyping On Blood Cells Of Compound #1 Treated-Mice (N = 10)

| Cell marker | | Control | 25 mg/kg | 50 mg/kg |
|---|---|---|---|---|
| CD8+ | mean | 6.66 | 10.11 | 8.65 |
| CD45+ | STD | 2.09 | 2.69 | 1.39 |
| | p | | 0.005 | 0.02 |
| NK+ | mean | 6.01 | 5.90 | 8.14 |
| CD3− | STD | 0.98 | 1.39 | 1.35 |
| | p | | 0.5 | 0.005 |
| NK+ | mean | 3.43 | 5.84 | 3.25 |
| CD3+ | STD | 0.76 | 2.08 | 0.57 |
| | p | | 0.02 | 0.289 |
| CD11b+ | mean | 9.60 | 13.71 | 9.68 |
| | STD | 2.79 | 2.68 | 3.59 |
| | p | | 0.015 | 0.4 |

TABLE 3b

Immunophenotyping On Spleen Cells of Compound #1 Treated-Mice (N = 10)

| Cell marker | | Control | 25 mg/kg | 50 mg/kg |
|---|---|---|---|---|
| TCR+ | mean | 38.93 | 39.78 | 45.09 |
| | STD | 3.83 | 7.61 | 7.34 |
| | p | | 0.421 | 0.035 |
| Ly5 | mean | 55.49 | 54.08 | 50.35 |
| | STD | 3.44 | 7.30 | 6.72 |
| | p | | 0.37 | 0.034 |

TABLE 4

Immunophenotyping On Blood Cells Of Mice Treated With Compound 190 1 In Combination With Cyclophosphamide (N = 4)

| Cell marker | | cyclo-phosphamide 100 mg/kg | CY + cpd #1 25 mg/kg | CY + cpd #1 50 mg/kg |
|---|---|---|---|---|
| CP8+ | mean | 15.05 | 13.25 | 20.8 |
| | STD | 3.89 | 0.07 | 0.85 |
| CD45+ | p | | 0.33 | 0.05 |

Spleen: no effect

TABLE 5a

Immunophenotyping On Blood Cells Of Mice Treated With Compound #1 In Combination With 5 Fluorouracil (N = 4)

| Cell marker | | 5 FU (80 mg/kg) | 5 FU + cpd #1 25 mg/kg | 5 FU + cpd #1 50 mg/kg |
|---|---|---|---|---|
| CD8+ | mean | 6.66 | 10.11 | 8.65 |
| | STD | 2.09 | 2.69 | 1.39 |
| CD45+ | p | | 0.005 | 0.022 |
| NK+ | mean | 3.24 | 3.58 | 4.12 |
| | STD | 0.66 | 1.01 | 0.74 |
| | p | | 0.38 | 0.01 |

TABLE 5b

Immunophenotyping On Spleen Cells Of Mice Treated With Compound #1 In Combination With 5 Fluorouracil (N = 4)

| Cell marker | | 5 FU (80 mg/kg) | 5 FU + cpd #1 25 mg/kg | 5 FU + cpd #1 50 mg/kg |
|---|---|---|---|---|
| CD4+ | mean | 10.0 | 13.19 | 12.06 |
| CD45− | STD | 1.98 | 3.19 | 2.27 |
| | p | | 0.015 | 0.04 |
| NK+ | mean | 4.22 | 3.32 | 3.17 |
| | STD | 0.5 | 0.45 | 0.36 |
| | p | | 0.0005 | 0.0001 |

ANTITUMOR ASSESSMENT PROTOCOL

The compounds were tested for tumor growth control using the following procedures.

Example 92

Effect of compound #1 on growth of breast carcinoma in combination with cyclophosphamide.

Balb/C Mice (n-5/Gr) were used along with DA-3 mammary carcinoma cell line. The mice were treated from −2 to 13 days. Animals were monitored for tumor takes/tumor size and body weights for three weeks from Day 0 until Day 21. D0 was the day of tumor cell inoculation and D21 was the day of experiment termination.

Parameters of effect were measured by inhibition of tumor outgrowth and growth rate [tumors measured along the longest axis (length) and the perpendicular shortest axis (width) and the tumor volumes (T.V.±S.E.) was calculated by the formula T.V.=length (cm)×(width cm)$^2$/2.] assessment of body weight loss.

The statistical significance of difference between tumor takes and tumor sizes of control-untreated and drug-treated groups is estimated using the Chi-square and Student's t tests respectively with significance determined at n<0.05.

The mice were divided into the following 5 groups:
Gr.1—Normal Saline (0.2 ml/mouse i.p. starting at D2)
Gr.2—CY (100 mg/kg single bolus i.v. at D0)
Gr.3—Compound #1 (25 mg/kg i.p. starting at D2)
Gr.4—Compound #1 (50 mg/kg i.p. starting at D2)
Gr.5—CY (100 mg/kg i.v. at D0+compound #1 50 mg/kg i.p. starting at D2)

Figure 2:
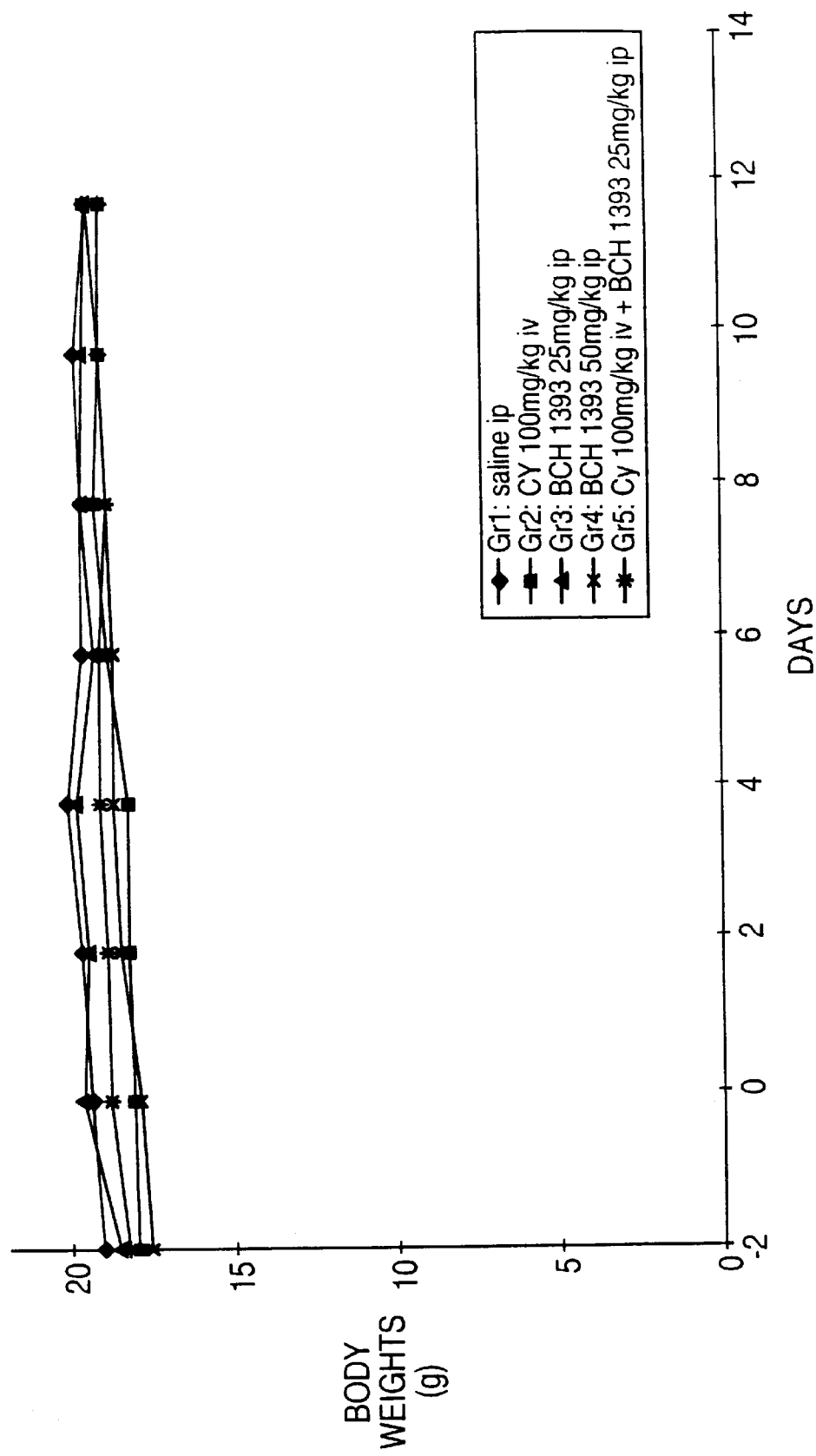
FIG. 2 illustrates the body weight variations for mice treated with the same regimen as in FIG. 1

Results are presented in Table 6 and FIGS. 1 and 2.

TABLE 6

Effect of compound #1 treatment on Tumor Outgrowth

| Group/Day | 4 | 6 | 8 | 10 |
|---|---|---|---|---|
| Gr. 1: saline | 5/5* | 5/5 | 5/5 | 5/5 |
| Gr. 2: CY @ 100 mg/kg | 5/5 | 5/5 | 5/5 | 5/5 |
| Gr. 3: #1 @ 25 mg/kg | 2/5† | 2/5† | 3/5 | 4/5 |
| Gr. 4: #1 @ 50 mg/kg | 3/5 | 3/5 | 3/5 | 3/5 |
| Gr. 5: CY @ 100 mg/kg + #1 @ 50 mg/kg | 4/5 | 5/5 | 5/5 | 5/5 |

*Tumor takes = # tumor-bearing mice/total # of mice
†p < 0.05 by Chi-square test

Example 93

Evaluation of Compound #1 in combination with Cytoxan (CTX, 20 mg/kg) against DA-3 mammary carcinoma.

Combination of compound #1 (25 and 50 mg/kg i.p. daily) plus CTX (20 mg/kg i.v. single bolus) was evaluated against day 4 established DA-3 tumors.

Figure 3:
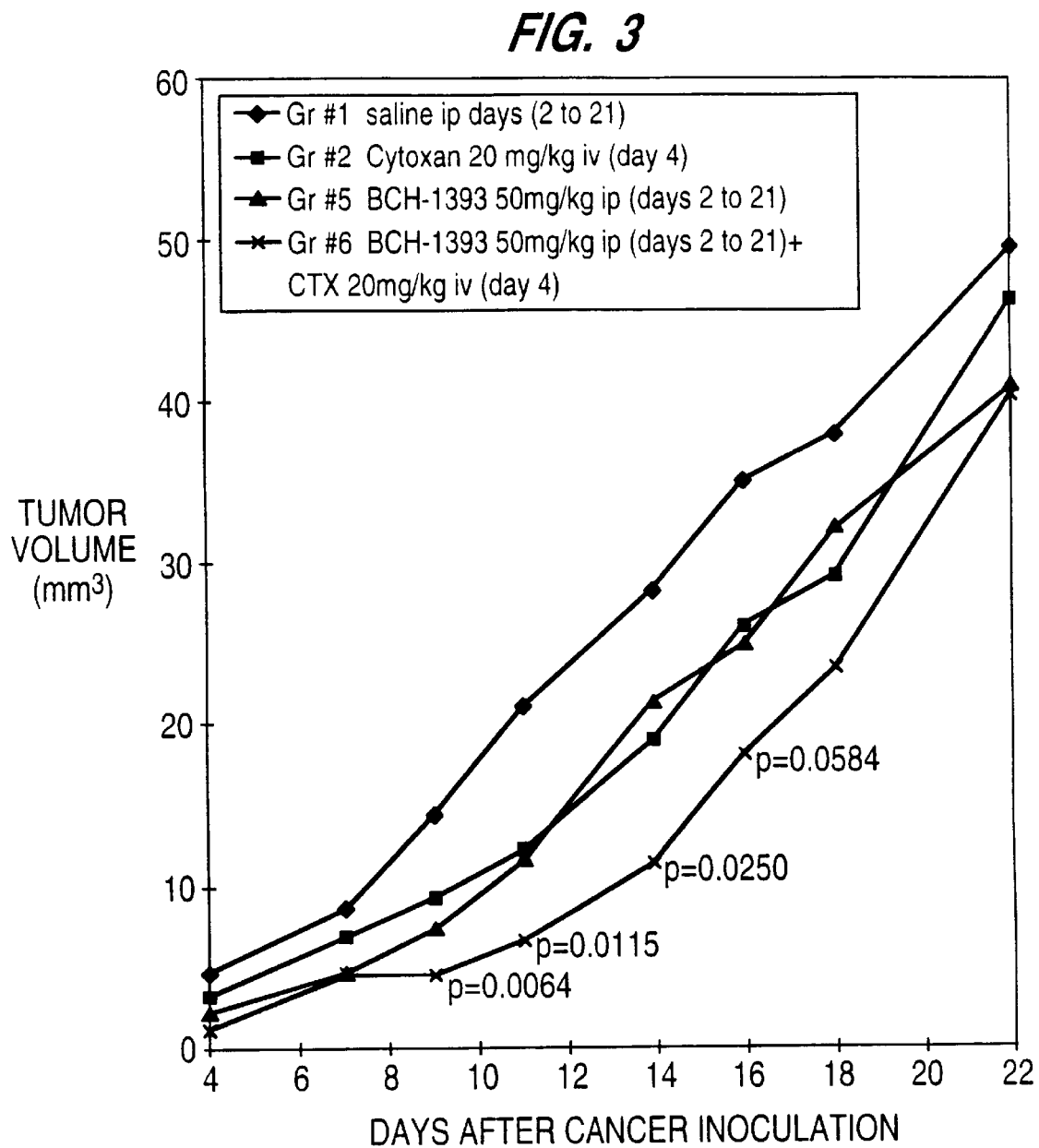
FIG. 3 illustrates the variations in tumor volume for mice treated with Cytoxan, or compound #1, or both.
Figure 4:
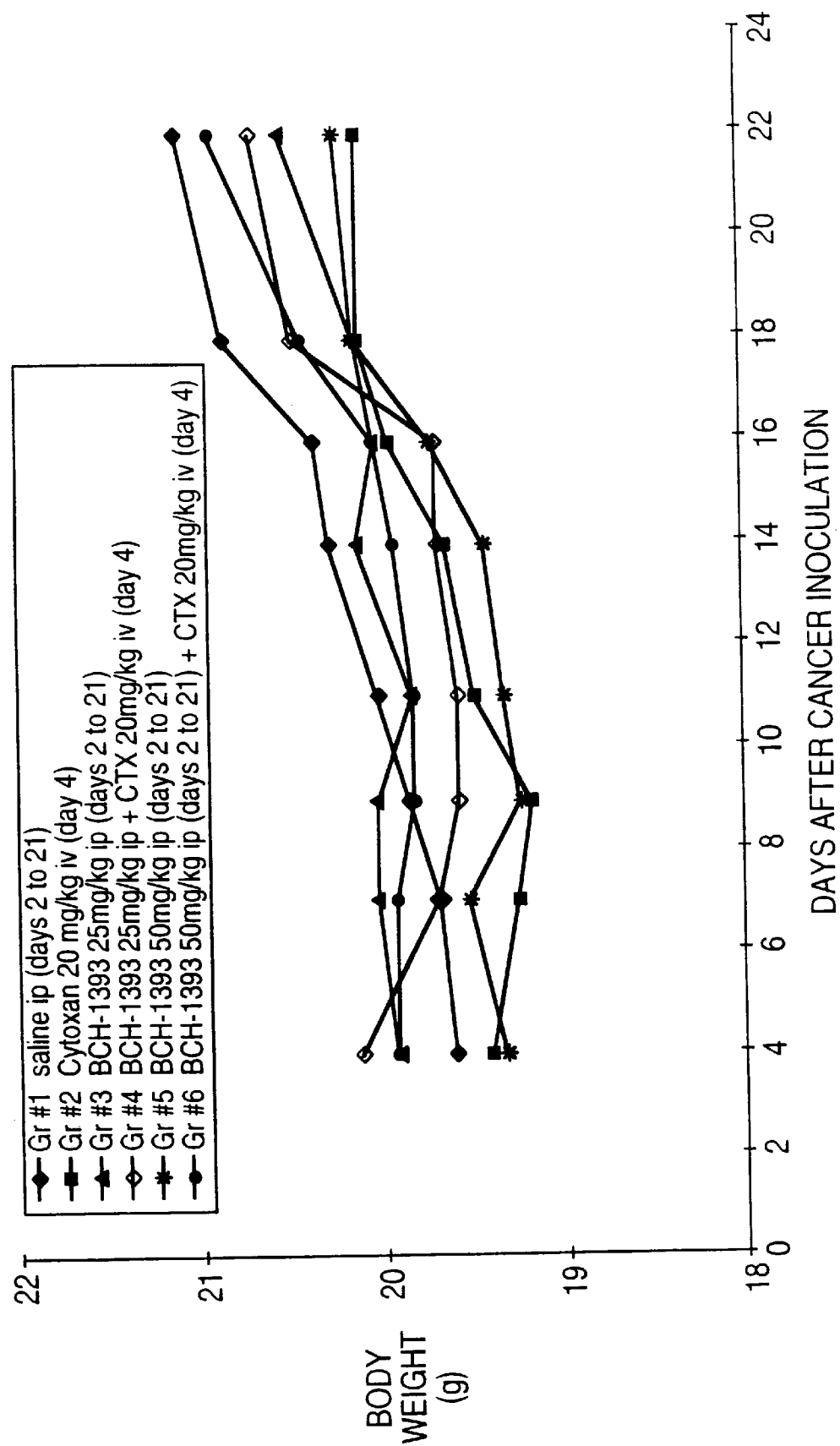
FIG. 4 illustrates the body weight variations for mice treated with the same regimen as in FIG. 3.

Results showed no significant effect of combination treatment of compound #1 (at 25 mg/kg) plus CTX. However, a significant but transient effect was observed with CTX plus compound #1 at 50 mg/kg from day 9 until day 18 (FIG. 3). The decay of the positive anti-tumor effect is possibly due to the generation of T-supressor cells at the later stage of tumor growth. No significant body weight loss was observed (FIG. 4).

Example 94

Evaluation of Compound #1 in combination with Cytoxan (CTX, 28 mg/kg) against DA-3 mammary carcinoma.

In another experiment, the CTX treatment was prolonged. Balb/c mice were injected s.c. with 5×10$^5$ DA-3 tumor cells at day 0. At day 4 when established tumors appeared, tumor-bearing animals were randomized (n=11/gr.) and injected with CTX (at 28 mg/kg) i.v. bolus injections at days 4, 11, and 18. Treatment with compound #1 was initiated using standard treatment regimen of daily i.p. injections at 50 mg/kg starting from day 2 until day 28.

Results of this experiment (Table 7) show a highly statistically significant (p,0.001-p<0.005) anti-tumor effect of the compound #1 (BCH-1393)+CTX combination treatment from day 11 until day 30 of tumor growth. No significant body weight loss was observed (Table 8).

Example 95
Evaluation of compound #1 in combination with 5FU against colon adenocarcinoma.

C57/BL mice 6–8 weeks old (n=7–9/gr) were injected with 3×10⁵ MC38 colon adenocarcinoma cells s.c. on day 0. On day 7, tumor-bearing mice were randomized and injected with 5FU at 20 mg/kg either alone or in combination with levamisole at 20 mg/kg i.p. or with compound #1 at 25 and 50 mg/kg i.p. over a four week period. During this period, animals were treated for 5 consecutive days, untreated for 2 days, and treated again for 5 consecutive days per week for 4 weeks.

Figure 5:
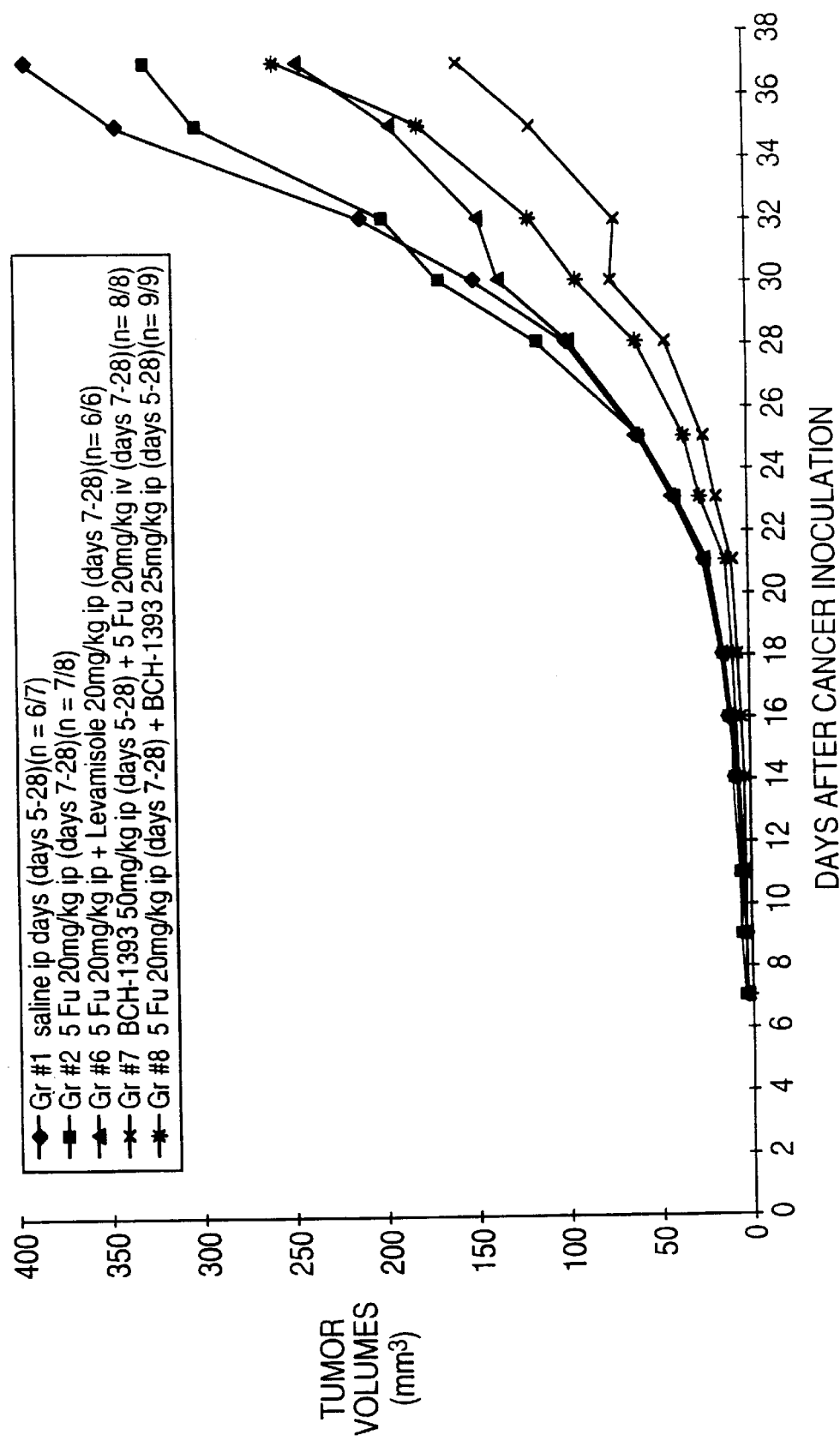
FIG. 5 illustrates the variations in tumor volume for mice treated with 5FU, 5FU with levamisole, and 5FU with compound #1.

Results of this experiment show a significant dose-dependent anti-tumor effect following compound #1 (at 50 and 25 mg/kg)+5FU (20 mg/kg) compared to control untreated group (FIG. 5). The anti-tumor effect of 5FU+Compound #1 (at 50 mg/kg) was markedly better than that of 5FU+Levamisole. A moderate anti-tumor response was observed following treatment with 5FU (20 mg/kg) alone or with 5FU (20 mg/kg) plus Levamisole (20 mg/kg). This may be due to the fact that 20 mg/kg represents a suboptimal dose of 5FU for MC38 colon adenocarcinoma.

Example 96
In vivo toxicity of Compound #1

The objective of this study was to find the toxic dose of compound #1 after repeated intravenous injections in Fisher male and female rats.

Groups of 3 male rats, and 3 female rats were injected daily i.v. for 5 consecutive days. A first group received 500 mg/kg, a second group 250 mg/kg, and a third group 125 mg/kg. In addition, one male and one female were injected with 1000 mg/kg. An untreated group (male and female) was included in the experiment. For all doses a constant volume of 0.1 mg/100 g was used. Injections were started on day 0 and continued until day 4 (5 days). During treatment, weight changes were recorded daily and the rats were observed for at least 1 hour post-injection for signs of drug effect. On day 8, the rats were euthanatized and a macroscopic examination of the internal organs was performed.

Figure 6:
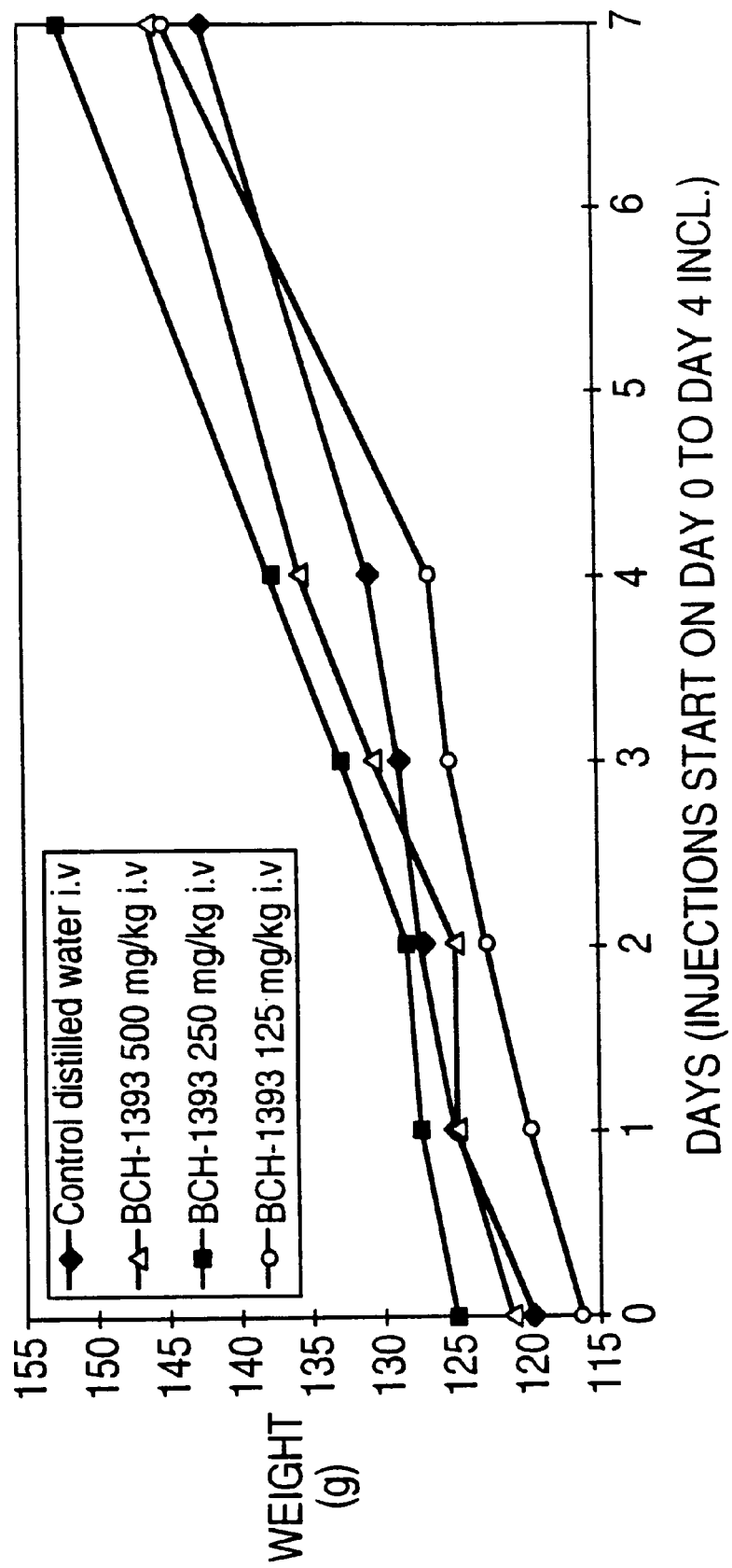
FIG. 6 illustrates the growth curves of male Fisher rats treated with compound #1 at high doses.
Figure 7:
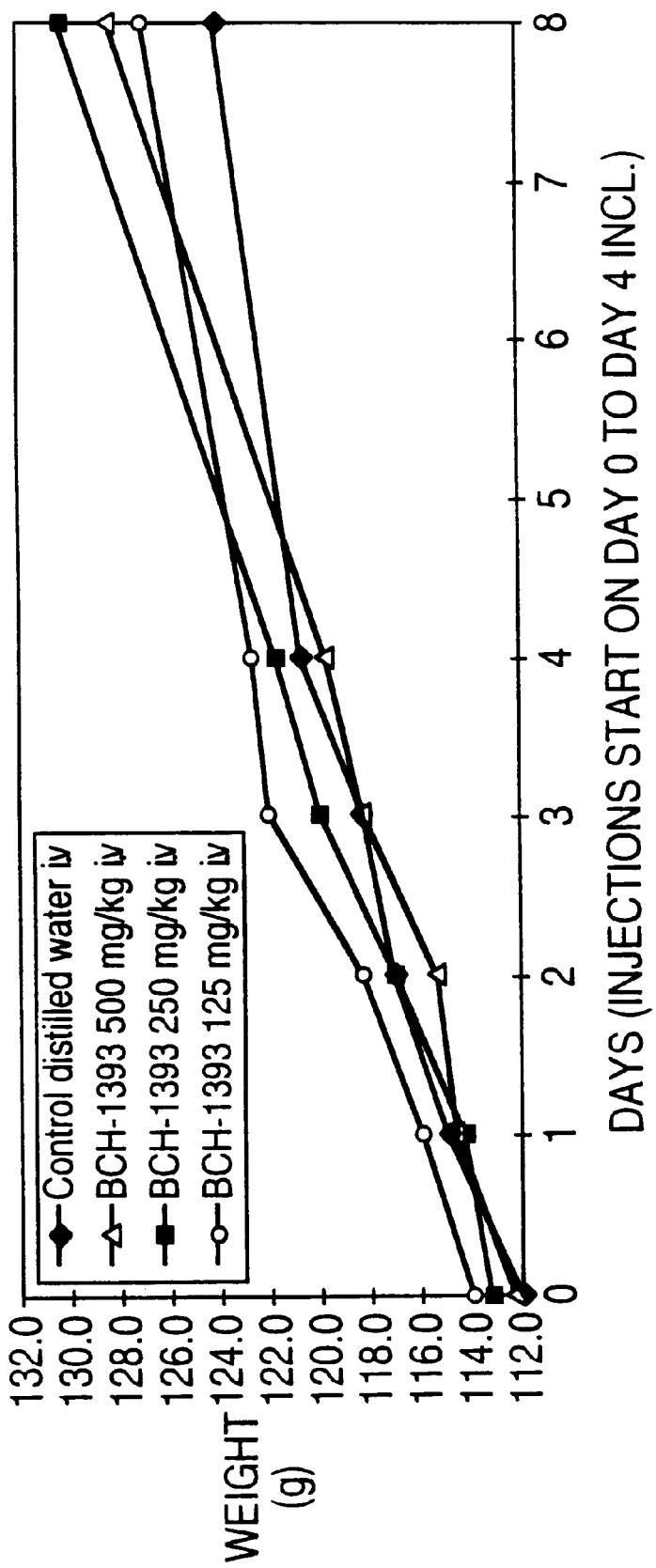
FIG. 7 illustrates the growth curves of female Fisher rats treated with compound #1 at high doses.

Both rats (1 male and 1 female) injected with 1000 mg/kg i.v. showed severe colonic convulsions and died within 10 minutes. With 500 mg/kg, all rats were observed to have twitches of the torso area, tremors of the forepaws and jumping episods. These signs lasted less than 1 hour and were comparable after each of the five injections. The growth curves of the animal were not affected when compared to controls. With the two lower doses (250 mg/kg and 125 mg/kg), no abnormal signs were observed at any time during dosing and the growth curves were normal (FIGS. 6 and 7). No drug induced changes were noted on necropsy of these animals.

Compound #1 is well tolerated when injected i.v. in Fisher rats. A dose of 250 mg/kg injected for 5 consecutive days produced no signs of toxicity. The compound caused colonic convulsions and was lethal at the dose of 1000 mg/kg. A dose of 500 mg/kg produced some short lasting abnormal signs but no lethality of effects on the growth of the animals.

CONCLUSIONS

From the data, in vitro, the compounds of the invention, in particular compound #1, appears to activate T cells (including CTL's) and B cells.

In vivo, the compound of the invention, in particular compound #1, increases the number of CTL's.

The compounds of the present invention, in particular compound #1, appear to be well tolerated.

Compound #1 appears to inhibit tumor outgrowth in combination with cyclophosphamide against mouse mammary carcinoma in vivo.

Compound #1 appears to inhibit tumor outgrowth in combination with 5FU against mouse colon adenocarcinoma in vivo.

TABLE 7 balb-c mice, 5.0 × 10⁵ sc DA-3 cells p #28, testing compound #1 with Cytoxan
injections of cells April 17th, treatment with compound #1 started on April 20th
measurement and treatment with Cytoxan started on April 21th, 1995,
Data of tumor sizes including mice with tumor only

| DAY | 4 | 7 | 9 | 11 | 14 | 16 |
|---|---|---|---|---|---|---|
| Gr #1 saline Ip (Days 3–28) | 3.5 | 11.0 | 20.3 | 34.4 | 61.9 | 69.5 |
| sem | 1.37 | 2.11 | 3.22 | 3.76 | 7.39 | 6.00 |
| mice number | n = 11/11 | n = 11/11 | n = 11/11 | n = 11/11 | n = 11/11 | n = 11/11 |
| Gr #2 CTX 28 mg/kg Ip (Days 4, 11, 18) | 4.2 | 10.5 | 18.6 | 30.7 | 50.6 | 54.5 |
| sem | 1.45 | 2.37 | 3.81 | 4.83 | 7.93 | 5.98 |
| p value | 0.7017 | 0.7422 | 0.7392 | 0.5506 | 0.3110 | 0.1182 |
| mice number | n = 11/11 | n = 11/11 | n = 11/11 | n = 11/11 | n = 11/11 | n = 11/11 |
| Gr #3 BCH-1393 50 mg/kg Iv (days 3–28) | 2.7 | 10.2 | 18.1 | 29.2 | 50.1 | 58.5 |
| sem | 1.01 | 2.87 | 4.46 | 6.82 | 10.21 | 12.90 |
| p value | 0.6460 | 0.7141 | 0.6927 | 0.5064 | 0.3588 | 0.4499 |
| mice number | n = 11/11 | n = 11/11 | n = 11/11 | n = 11/11 | n = 11/11 | n = 11/11 |
| Gr #4 BCH-1393 50 mg/kg Ip (Days 3–28) + CTX 28 mg/kg Iv (days 4, 11, 18) | 3.6 | 6.5 | 12.6 | 20.2 | 29.5 | 41.7 |
| sem | 1.40 | 1.85 | 3.44 | 3.77 | 5.58 | 6.46 |
| p value | 0.9625 | 0.0883 | 0.1186 | 0.0085 | 0.0014 | 0.0031 |
| mice number | n = 11/11 | n = 11/11 | n = 11/11 | n = 10/11 | n = 10/11 | n = 10/11 |
| DAY | 18 | 21 | 23 | 25 | 28 | 30 |
| Gr #1 saline Ip (Days 3–28) | 77.3 | 99.9 | 127.3 | 160.7 | 182.9 | 206.9 |
| sem | 7.51 | 10.39 | 13.92 | 22.70 | 21.9 | 21.8 |
| mice number | n = 11/11 | n = 11/11 | n = 11/11 | n = 11/11 | n = 11/11 | n = 11/11 |
| Gr #2 CTX 28 mg/kg Ip (Days 4, 11, 18) | 63.4 | 88.5 | 93.4 | 106.3 | 130.9 | 151.6 |
| sem | 8.43 | 8.99 | 8.49 | 8.91 | 12.42 | 13.99 |
| p value | 0.2337 | 0.4225 | 0.0503 | 0.0372 | 0.0519 | 0.0453 |

TABLE 7-continued

| | | | | | | |
|---|---|---|---|---|---|---|
| mice number | n = 11/11 | n = 11/11 | n = 11/11 | n = 11/11 | n = 11/11 | n = 11/11 |
| Gr #3 BCH-1393 50 mg/kg Iv (days 3–28) | 66.3 | 94.2 | 131.4 | 130.9 | 152.5 | 187.2 |
| sem | 15.45 | 18.63 | 36.55 | 29.51 | 28.68 | 35.09 |
| p value | 0.5316 | 0.7936 | 0.9174 | 0.4335 | 0.4087 | 0.6383 |
| mice number | n = 11/11 | n = 11/11 | n = 11/11 | n = 11/11 | n = 11/11 | n = 11/11 |
| Gr #4 BCH-1393 50 mg/kg Ip (Days 3–28) + CTX 28 mg/kg Iv (days 4, 11, 18) | 44.9 | 63.4 | 69.6 | 95.4 | 104.2 | 115.8 |
| sem | 6.52 | 9.50 | 9.90 | 12.57 | 13.38 | 15.05 |
| p value | 0.0025 | 0.0102 | 0.0019 | 0.0056 | 0.0039 | 0.0017 |
| mice number | n = 10/11 | n = 10/11 | n = 10/11 | n = 10/11 | n = 10/11 | n = 10/11 |

TABLE 8 balb-c mice, $5.0 \times 10^5$ sc DA-3 cells p #28, testing compound #1 with Cytoxan injections of cells April 17th, treatment with compound #1 started on April 20th, measurement and treatment with Cytoxan started on April 21th, 1995, Data of body weight (including every mice in the group)

| DAY | 4 | 7 | 9 | 11 | 14 | 16 |
|---|---|---|---|---|---|---|
| Gr #1 saline Ip (Days 3–28) | 19.2 | 19.7 | 19.5 | 19.6 | 19.2 | 19.8 |
| sem | 0.25 | 0.34 | 0.32 | 0.30 | 0.31 | 0.31 |
| mice number | n = 11/11 | n = 11/11 | n = 11/11 | n = 11/11 | n = 11/11 | n = 11/11 |
| Gr #2 CTX 28 mg/kg Ip (Days 4, 11, 18) | 19.2 | 19.8 | 19.8 | 19.9 | 19.2 | 19.7 |
| sem | 0.22 | 0.28 | 0.31 | 0.40 | 0.31 | 0.29 |
| p value | 1.0000 | 0.8471 | 0.4488 | 0.6040 | 1.0000 | 0.8403 |
| mice number | n = 11/11 | n = 11/11 | n = 11/11 | n = 11/11 | n = 11/11 | n = 11/11 |
| Gr #3 BCH-1393 50 mg/kg Iv (days 3–28) | 18.6 | 19.1 | 19.3 | 18.9 | 18.9 | 19.5 |
| sem | 0.27 | 0.33 | 0.39 | 0.33 | 0.33 | 0.35 |
| p value | 0.1704 | 0.2144 | 0.7352 | 0.1309 | 0.5701 | 0.5836 |
| mice number | n = 11/11 | n = 11/11 | n = 11/11 | n = 11/11 | n = 11/11 | n = 11/11 |
| Gr #4 BCH-1393 50 mg/kg Ip (Days 3–28) + CTX 28 mg/kg Iv (days 4, 11, 18) | 18.7 | 18.2 | 19.1 | 19.0 | 18.6 | 19.5 |
| sem | 0.29 | 0.17 | 0.16 | 0.18 | 0.23 | 0.15 |
| p value | 0.2721 | 0.1904 | 0.3463 | 0.0954 | 0.1947 | 0.3263 |
| mice number | n = 11/11 | n = 11/11 | n = 11/11 | n = 10/11 | n = 10/11 | n = 10/11 |

| DAY | 18 | 21 | 23 | 25 | 28 | 30 |
|---|---|---|---|---|---|---|
| Gr #1 saline Ip (Days 3–28) | 19.5 | 19.6 | 19.7 | 19.8 | 19.8 | 20.0 |
| sem | 0.27 | 0.27 | 0.26 | 0.28 | 0.25 | 0.31 |
| mice number | n = 11/11 | n = 11/11 | n = 11/11 | n = 11/11 | n = 11/11 | n = 11/11 |
| Gr #2 CTX 28 mg/kg Ip (Days 4, 11, 18) | 19.6 | 19.8 | 19.7 | 20.1 | 20.3 | 20.4 |
| sem | 0.27 | 0.25 | 0.26 | 0.27 | 0.29 | 0.30 |
| p value | 0.8209 | 0.6405 | 1.0000 | 0.5141 | 0.2721 | 0.431291 |
| mice number | n = 11/11 | n = 11/11 | n = 11/11 | n = 11/11 | n = 11/11 | n = 11/11 |
| Gr #3 BCH-1393 50 mg/kg Iv (days 3–28) | 18.9 | 19.3 | 19.3 | 19.5 | 19.7 | 20.0 |
| sem | 0.37 | 0.32 | 0.34 | 0.35 | 0.39 | 0.41 |
| p value | 0.2023 | 0.4121 | 0.3254 | 0.5687 | 0.8530 | 1.000 |
| mice number | n = 11/11 | n = 11/11 | n = 11/11 | n = 11/11 | n = 11/11 | n = 11/11 |
| Gr #4 BCH-1393 50 mg/kg Ip (Days 3–28) + CTX 28 mg/kg Iv (days 4, 11, 18) | 19.3 | 18.9 | 18.8 | 19.5 | 19.4 | 19.3 |
| sem | 0.19 | 0.20 | 0.17 | 0.20 | 0.23 | 0.26 |
| p value | 0.4353 | 0.0506 | 0.0117 | 0.4592 | 0.2201 | 0.1050 |
| mice number | n = 10/11 | n = 10/11 | n = 10/11 | n = 10/11 | n = 10/11 | n = 10/11 |

We claim:

1. A compound of formula I:

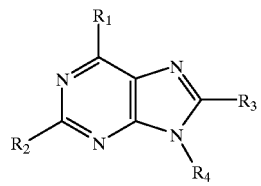

wherein $R_1$ is substituted amino represented by formula $NR^5R^6$ wherein $R^5$ and $R^6$ are independently selected from the group consisting of hydrogen, $C_{1-4}$ alkyl, and unsubstituted amino with the proviso that $R^5$ and $R^6$ are not both hydrogen, and further that $R^5$ and $R^6$ are not both amino;

$R_2$ and $R_3$ are independently selected from the group consisting of hydrogen; $C_{1-4}$ alkyl; amino; substituted or unsubstituted thiol; and halogen; and $R_4$ is represented by the formula $R^{12}$-$X^{12}$ wherein $R^{12}$ is a saturated or unsaturated linear hydrocarbon chain of 5–20 carbons optionally containing one or more interruptions within the chain by a heteroatom, and optionally substituted with one or more =O, or =S, and $X^{12}$ is selected from the group consisting of, an aminoalkyl group, and a known amino acid bound by its α-amino group.

2. A compound selected from the group consisting of:

| | |
|---|---|
| Compound #III | 5-(6-Chloropurin-9-yl)-pentanol |
| Compound #V | 5-(6-Dimethylaminopurin-9-yl)-pentanol |
| Compound #1 | N-5-(6-Dimethylaminopurin-9-yl)-pentoxycarbonyl-D-Arginine |
| Compound #2 | N-5-(6-Dimethylaminopurin-9-yl)-petnoxycarbonyl-L-Arginine |
| Compound #3 | N-5-(6-Methylaminopurin-9-yl)-pentoxycarbonyl-D-Arginine |
| Compound #3a | 5-(6-Methylaminopurin-9-yl)-pentanol |
| Compound #4 | N-5-(6-Methylaminopurin-9-yl)-pentoxycarbonyl-L-Arginine |
| Compound #5 | N-5-(6-Aminopurin-9-yl)-pentoxycarbonyl-D-Arginine |
| Compound #5a | 5-(6-Aminopurin-9-yl)-pentanol |
| Compound #6 | N-5-(6-Aminopurin-9-yl)-pentoxycarbonyl-L-Arginine |
| Compound #7 | N-5-(6-Hydrazinopurin-9-yl)-pentoxycarbonyl-D-Arginine |
| Compound #7a | 5-(6-Hydrazinopurin-9-yl)-pentanol |
| Compound #8 | N-5-(6-Hydrazinopurin-9-yl)-pentoxycarbonyl-L-Arginine; |
| Compound #9 | N-5-(6-Chloropurin-9-yl)-pentoxycarbonyl-D-Arginine; |
| Compound #10 | N-5-(6-Chloropurin-9-yl)-pentoxycarbonyl-L-Arginine; |
| Compound #11 | N-5-(6-Hydroxypurin-9-yl)-petnoxycarbonyl-D-Arginine; |
| Compound #12 | N-5-(6-Mercaptopurin-9-yl)-pentoxycarbonyl-D-Arginine; |
| Compound #13 | N-5-(6-Mercatopurin-9-yl)-petnoxycarbonyl-L-Arginine; |
| Compound #14 | N-5-(6-Dimethylaminopurin-9-yl)-petnoxycarbonyl-Glycine; |
| Compound #15 | N-5-(6-Dimethylaminopurin-9-yl)-7'-ethoxy-ethoxycarbonyl-D-Arginine; |
| Compound #16 | (2S,4S)-2-(6-Dimethylaminopurin-9-yl)-4-(methyloxycarbonyl-D-Arginine)-1,3-dioxlane; |
| Compound #17 | N-5-(6-Dimethylamino-8-bromopurin-9-yl)-pentoxycarbonyl-L-Arginine; |
| Compound #18 | N-5-(6-Dimethylamino-8-bromopurin-9-yl)-pentoxycarbonyl-D-Arginine; |
| Compound #19 | 5-(Purin-9-yl)-pentanol; |
| Compound #20 | N-5-(Purin-9-yl)-pentoxycarbonyl-D-Arginine; |
| Compound #21 | N-5-(Purin-9-yl)-pentoxycarbonyl-L-Arginine; |
| Compound #22 | N-5-(6-Dimethylaminopurin-9-yl)-pentoxycarbonyl-L-Valyl-L-Prolyl-L-Leucine; |
| Compound #23 | N-5-(6-N',N'-Dimethylaminopurin-9-yl)-pentoxycarbonyl-L-Isoleucyl-L-Prolyl-L-Isoleucine; |
| Compound #24 | 5-(6-Cyclopropylaminopurin-9-yl)-pentanol; |
| Compound #25 | N-5-(6-Cyclopropylaminopurin-9-yl)-pentoxycarbonyl-D-Arginine; |
| Compound #26 | N-5-(6-Cyclopropylaminopurin-9-yl)-pentoxycarbonyl-L-Arginine; |
| Compound #27 | 5-(6-Azetidinepurin-9-yl)-pentanol; |
| Compound #28 | N-5-(6-Azetidinepurin-9-yl)-pentoxycarbonyl-D-Arginine; |
| Compound #29 | N-5-(6-Azetidinepurin-9-yl)-pentoxycarbonyl-L-Arginine; |
| Compound #30 | trans-(6-Chloropurin-9-yl)-4-methyl-cyclohexyl-methanol; |
| Compound #31 | trans-(6-Dimethylaminopurin-9-yl)-4-methyl-cyclohexyl-methanol; |
| Compound #32 | trans-(6-Dimethylaminopurin-9-yl)-4-methyl-cyclohexyl-methyloxycarbonyl-D-Arginine; |
| Compound #33 | trans-(6-Hydroxypurin-9-yl)-4-methyl-cyclohexyl-methanol; |
| Compound #34 | trans-(6-Methoxypurin-9-yl)-4-methyl-cyclohexyl-methanol; |
| Compound #35 | cis-(6-Dimethylaminopurin-9-yl)-4-methyl-cyclohexyl-methanol; |
| Compound #36 | cis-(6-Dimethylaminopurin-9-yl)-4-methyl-cyclohexyl-methyloxycarbonyl-D-arginine; |
| Compound #37 | N-5-(6-Dimethylaminopurin-9-yl)-pentoxycarbonyl-D-Citrulline; |
| Compound #38 | 5-(6-Methylaziridinepurin-9-yl)-pentanol; |
| Compound #39 | N-5-(6-Methylaziridinepurin-9-yl)-pentoxycarbonyl-D-Arginine; |
| Compound #40 | N-5-(6-Dimethylaminopurin-9-yl)-7-thioethoxy-ethoxycarbonyl-D-Arginine; |
| Compound #41 | Meta-(6-Dimethylaminopurin-9-yl)-methyl-benzyloxycarbonyl-D-Arginine; |
| Compound #42 | N-5-(6-Dimethylaminopurin-9-yl)-3-pentnyl-1-oxycarbonyl-D-Arginine; |
| Compound #43 | 5-]6-(1-methyl-2-acetoxy)-ethylaminopurin-9-yl]-pentanol; |
| Compound #44 | N-5-[6-(1-methyl-2-acetoxy)-ethylaminopurin-9-yl]-pentyloxycarbonyl-D-Arginine; |
| Compound #45 | 5-(2,6-Dichloropurin-9-yl)-pentanol; |
| Compound #46 | N-5-(2,6-Dichloropurin-9-yl)-petnoxycarbonyl-D-Arginine; |
| Compound #47 | N-5-(2,6-Dichloropurin-9-yl)-pentoxycarbonyl-L-Arginine; |
| Compound #48 | 5-(2-Amino-6-Dimethylaminopurin-9-yl)-pentanol; |
| Compound #49 | 5-(6-Dimethylamino-8-methylthiopurin-9-yl)-pentanol; |
| Compound #50 | N-5-(6-Dimethylamino-8-methylthiopurin-9-yl)-pentoxycarbonyl-D-Arginine; |
| Compound #51 | 5-(6-Methoxypurin-9-yl)-pentanol; |
| Compound #52 | N-5-(6-Methoxypurin-9-yl)-pentoxycarbonyl-D-Arginine; |
| Compound #53 | N-5-(2-chloro-6-methoxypurin-9-yl)-pentoxycarbonyl-D-Arginine; |
| Compound #54 | N-5-(6-Dimethylaminopurin-9-yl)-pentoxycarbonyl-D-Ornithine; |
| Compound #55 | N-5-(6-Dimethylaminopurin-9-yl)-pentoxycarbonyl-L-Ornithine; |
| Compound #56 | N-5-(6-Dimethylaminopurin-9-yl)-pentoxycarbonyl-L-Valine; |
| Compound #57 | N-5-(6-Dimethylaminopurin-9-yl)-petnoxycarbonyl-D-Valine; |
| Compound #58 | N-5-(6-Dimethylaminopurin-9-yl)-petnoxycarbonyl-ethylaminehydrochloride; |
| Compound #59 | 5-(6-Mercaptopurin-9-yl)-pentanol; |
| Compound #60 | 5-(6-Methylthiopurin-9-yl)-pentanol; |
| Compound #61 | 4-(6-Chloropurin-9-yl)-butanol; |
| Compound #62 | 4-(6-Dimethylaminopurin-9-yl)-butanol; |
| Compound #63 | N-4-(6-Dimethylaminopurin-9-yl)-butoxycarbonyl-D-Arginine; |
| Compound #64 | N-4-(6-Dimethylaminopurin-9-yl)-butoxycarbonyl-L-Arginine; |
| Compound #65 | 6-(6-Chloropurin-9-yl)-hexanol; |
| Compound #66 | 6-(6-Dimethylaminopurin-9-yl)-hexanol; |
| Compound #67 | N-6-(6-Dimethylaminopurin-9-yl)-hexylcarbonyl-D-Arginine; |
| Compound #68 | N-6-(6-N',N'-Dimethylaminopurin-9-yl)-hexyloxycarbonyl-L-Arginine; |
| Compound #69 | cis-(6-Hydroxypurin-9-yl)-4-methyl-cyclohexyl-methanol; |
| Compound #70 | cis-(6-Hydroxypurin-9-yl)-4-methyl-cyclohexyl-methyloxycarbonyl-D-Arginine; |
| Compound #71 | trans-(6-Hydroxypurin-9-yl)-4-methyl-cyclohexyl-methyloxycarbonyl-D-Arginine; |
| Compound #72 | 5-(6-Dimethylaminopurin-9-yl)-pentylamine hydrochloride salt; |
| Compound #73 | N-5-(6-Methylaziridinepurin-9-yl)-pentyloxycarbonyl-L-Arginine; |
| Compound #74 | (2S,4S)-2-(6-Dimethylaminopurin-9-yl)-4-hydroxymethyl-1,3-dioxolane; |
| Compound #75 | (1S,3R) and (1R,3S)-1-(6-Dimethylaminopurin-9-yl)-methyl-3-cyclopentane methanol; |
| Compound #76 | (1S,3R) and (1R,3S)-1-(6-Dimethylaminopurin-9-yl)-methyl-3-(methyloxy-carbonyl-D-Arginine)-cyclopentane; |
| Compound #77 | (6-Dimethylaminopurin-9-yl)-7-ethylaminoethanol; |
| Compound #78 | (6-Dimethylaminopurin-9-yl)-7-ethylaminoethoxy-carbonyl-D-Arginine; |
| Compound #79 | (6-Dimethylaminopurin-9-yl)-7-ethylamino-ethoxycarbonyl-L-Arginine; |
| Compound #80 | 5-(6-Dimethylaminopurin-9-yl)-3-pentyn-1-ol; |
| Compound #81 | N-5-(6-Dimethylaminopurin-9-yl)-3-pentyl-1-oxycarbonyl-L-Arginine; |
| Compound #82 | (6-Dimethylaminopurin-9-yl)-7-thioethoxy-ethanol; |
| Compound #83 | (6-Dimethylaminopurin-9-yl)-7-thioethoxy-ethoxycarbonyl-L-Arginine; |
| Compound #84 | (2S,4S) and (2R,4R)-2-(6-Dimethylaminopurin-9-yl)-4-(methoxycarbonyl-D-Arginine)-1,3-oxathiolane; |
| Compound #85 | (6-Dimethylaminopurin-9-yl)-7-ethoxy-ethoxyethanol; |
| Compound #86 | (6-Dimethylaminopurin-9-yl)-7-ethoxy-ethoxycarbonyl-D-Arginine; |

-continued

Compound #87  (6-Dimethylaminopurin-9-yl)-7-ethoxy-ethoxycarbonyl-L-Arginine; and
Compound #88  5-(6-Dimethylamino-8-bromopurin-9-yl)-pentanol.

3. The compound according to claim 1, wherein $R_4$ is $(CH_2)$—L—O—CO—$X^{12}$, wherein L is selected from the group consisting of $(CH_2)_n$, $(CH_2)_m$—Q—$(CH_2)_m$, and $(CH_2)_m$—C≡C—$(CH_2)_m$; Q is O, S, or NH; n is an integer between 3 and 6; and m is an integer between 1 and 3.

4. The compound according to claim 1, wherein $X^{12}$ is $(CH_2)_mNH_2$ wherein m is an integer between 1 and 6.

5. The compound according to claim 4, wherein m is 2.

6. The compound according to claim 1, wherein $X^{12}$ is a naturally occurring L- alpha amino acid or its D- stereoisomer.

7. The compound according to claim 6, wherein said amino acid is selected from the group consisting of: arginine, glycine, alanine, glutamic acid, valine, ornithine, or citrulline.

8. The compound according to claim 7, wherein said amino acid is D-arginine.

9. The compound according to claim 7, wherein said amino acid is L-arginine.

10. The compound according to claim 2 selected from the group consisting of:

Compound #III  5-(6-Chloropurin-9-yl)-pentanol
Compound #V    5-(6-Dimethylaminopurin-9-yl)-pentanol
Compound #1    N-5-(6-Dimethylaminopurin-9-yl)-pentoxycarbonyl-D-Arginine
Compound #2    N-5-(6-Dimethylaminopurin-9-yl)-pentoxycarbonyl-L-Arginine
Compound #3    N-5-(6-Methylaminopurin-9-yl)-pentoxycarbonyl-D-Arginine
Compound #3a   5-(6-Methylaminopurin-9-yl)-pentanol
Compound #5    N-5-(6-Aminopurin-9-yl)-pentoxycarbonyl-D-Arginine
Compound #5a   5-(6-Aminopurin-9-yl)-pentanol
Compound #6    N-5-(6-Aminopurin-9-yl)-pentoxycarbonyl-L-Arginine
Compound #7    N-5-(6-Hydrazinopurin-9-yl)-pentoxycarbonyl-D-Arginine
Compound #7a   5-(6-Hydrazinopurin-9-yl)-pentanol
Compound #8    N-5-(6-Hydrazinopurin-9-yl)-pentoxycarbonyl-L-Arginine;
Compound #11   N-5-(6-Hydroxypurin-9-yl)-pentoxycarbonyl-D-Arginine;
Compound #19   5-(Purin-9-yl)-pentanol;
Compound #20   N-5-(Purin-9-yl)-pentoxycarbonyl-D-Arginine;
Compound #51   5-(6-Methoxypurin-9-yl)-pentanol;
Compound #59   5-(6-Mercaptopurin-9-yl)-pentanol; and
Compound #60   5-(6-Methylthiopurin-9-yl)-pentanol.

11. The compound according to claim 10 being Compound #1 N-5-(6-Dimethylaminopurin-9-yl)-pentoxycarbonyl-D-Arginine.

12. A method for the treatment of mammary carcinoma comprising the step of administering to a mammal a pharmaceutically acceptable amount of a compound according to claim 1, 2, or 11.

13. A method for the inhibition of tumor growth in a mammal, including human, comprising the step of administering to a mammal a pharmaceutically acceptable amount of a compound according to claim 11.

14. A method for the treatment of mammary carcinoma comprising the step of administering to a mammal a pharmaceutically acceptable amount of a compound of Formula I:

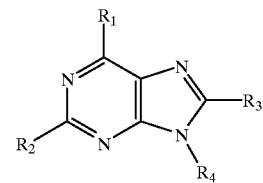

wherein $R_1$ is substituted amino represented by formula $NR^5R^6$ wherein $R^5$ and $R^6$ are independently selected from the group consisting of hydrogen, $C_{1-4}$ alkyl, and unsubstituted amino with the proviso that $R^5$ and $R^6$ are not both hydrogen, and further that $R^5$ and $R^6$ are not both amino;

$R_2$ and $R_3$ are independently selected from the group consisting of hydrogen; $C_{1-4}$ alkyl; amino; substituted or unsubstituted thiol; and halogen; and $R_4$ is represented by the formula $R^{12}$-$X^{12}$ wherein $R^{12}$ is a saturated or unsaturated linear hydrocarbon chain of 5–20 carbons optionally containing one or more interruptions within the chain by a heteroatom, and optionally substituted with one or more =O, or =S, and $X^{12}$ is selected from the group consisting of an aminoalkyl group and a known amino acid bound by its α-amino group.

15. A pharmaceutical composition containing a compound according to claim 1, 2, or 11, wherein said compound is present in admixture with a pharmaceutically acceptable carrier.

16. The compound according to claim 1, wherein $R_2$ is $NH_2$.

17. The compound according to claim 1, wherein $R_3$ is SH, or $SCH_3$.

18. The compound according to claim 1, wherein $R_1$ is selected from the group consisting of:

—$N(CH_3)_2$,

—$NHNH_2$,

—$NHCH_3$, or

—$N(NH_2)CH_3$

—NH—$CH(CH_3)CH_2$—O—$(CO)CH_3$,

19. The compound according to claim 1, wherein $R_2$ and $R_3$ are independently selected from the group consisting of: Cl, Br, I, and F.

20. The compound according to claim 19, wherein $R_2$ and $R_3$ are independently Cl, or Br.

21. The compound according to claim 20, wherein $R_3$ is Br.

22. The compound according to claim 20, wherein $R_2$ is Cl.

23. A method for increasing the number of cytotoxic T lymphocytes in a mammal, including a human, comprising the step of administering a pharmaceutically acceptable amount of a compound according to claim 1, 2, or 11.

* * * * *